(12) United States Patent
Pollack et al.

(10) Patent No.: US 8,845,872 B2
(45) Date of Patent: Sep. 30, 2014

(54) SAMPLE PROCESSING DROPLET ACTUATOR, SYSTEM AND METHOD

(75) Inventors: Michael G. Pollack, Durham, NC (US); Vamsee K. Pamula, Durham, NC (US); Vijay Srinivasan, Durham, NC (US)

(73) Assignees: Advanced Liquid Logic, Inc., Research Triangle Park, NC (US); Duke University, Durham, NC (US)

( * ) Notice: Subject to any disclaimer, the term of this patent is extended or adjusted under 35 U.S.C. 154(b) by 156 days.

(21) Appl. No.: 13/249,425

(22) Filed: Sep. 30, 2011

(65) Prior Publication Data

US 2012/0018306 A1   Jan. 26, 2012

Related U.S. Application Data

(63) Continuation of application No. 11/839,786, filed on Aug. 16, 2007, now abandoned, which is a continuation of application No. PCT/US2007/009379, filed on Apr. 18, 2007.

(60) Provisional application No. 60/745,049, filed on Apr. 18, 2006, provisional application No. 60/745,054, filed on Apr. 18, 2006, provisional application No. 60/806,400, filed on Jun. 30, 2006.

(51) Int. Cl.
  *G05D 7/06*   (2006.01)
  *C07K 1/113*   (2006.01)
  *C30B 7/00*   (2006.01)
  *C30B 29/58*   (2006.01)

(52) U.S. Cl.
  CPC .............. *C07K 1/1136* (2013.01); *C30B 7/00* (2013.01); *C30B 29/58* (2013.01)
  USPC ........................ 204/450; 204/600; 436/150

(58) Field of Classification Search
  USPC .......... 204/600, 660, 663; 436/150; 422/504, 422/82, 52, 53
  See application file for complete search history.

(56) References Cited

U.S. PATENT DOCUMENTS

| 4,390,403 A | 6/1983 | Batchelder |
| 4,636,785 A | 1/1987 | Le Pesant |

(Continued)

FOREIGN PATENT DOCUMENTS

| EP | WO03069380 A1 | 8/2003 |
| EP | WO2004027490 A1 | 4/2004 |

(Continued)

OTHER PUBLICATIONS

Wheeler et al. Anal.Chem., 2004, 76, 4833-4838.*

(Continued)

*Primary Examiner* — Jennifer Dieterle
*Assistant Examiner* — Gurpreet Kaur
(74) *Attorney, Agent, or Firm* — William A. Barrett; Ward & Smith, P.A.

(57) ABSTRACT

Sample processing droplet actuators, systems and methods are provided. According to one embodiment, a stamping device including a droplet microactuator is provided and includes: (a) a first plate including a path or network of control electrodes for transporting droplets on a surface thereof; (b) a second plate mounted in a substantially parallel orientation with respect to the first plate providing an interior volume between the plates, the second plate including one or more stamping ports for transporting some portion or all of a droplet from the interior volume to an exterior location; (c) a port for introducing fluid into the interior volume between the plates; and (d) a path or network of reference electrodes corresponding to the path or network of control electrodes. Associated systems and methods including the stamping device are also provided.

23 Claims, 17 Drawing Sheets

(56) References Cited

U.S. PATENT DOCUMENTS

| | | | |
|---|---|---|---|
| 4,863,849 A | 9/1989 | Melamede |
| 4,911,782 A | 3/1990 | Brown |
| 5,038,852 A | 8/1991 | Johnson et al. |
| 5,176,203 A | 1/1993 | Larzul |
| 5,181,016 A | 1/1993 | Lee et al. |
| 5,240,994 A | 8/1993 | Brink et al. |
| 5,486,337 A | 1/1996 | Ohkawa et al. |
| 5,498,392 A | 3/1996 | Wilding et al. |
| 5,503,803 A | 4/1996 | Brown |
| 5,641,681 A | 6/1997 | Carter |
| 5,644,239 A | 7/1997 | Huang et al. |
| 5,719,060 A | 2/1998 | Hutchens et al. |
| 5,720,923 A | 2/1998 | Haff et al. |
| 5,770,391 A | 6/1998 | Foote et al. |
| 5,770,457 A | 6/1998 | Stocker et al. |
| 5,779,977 A | 7/1998 | Haff et al. |
| 5,827,480 A | 10/1998 | Haff et al. |
| 5,846,396 A | 12/1998 | Zanzucchi et al. |
| 5,851,769 A | 12/1998 | Gray et al. |
| 5,980,719 A | 11/1999 | Cherukuri et al. |
| 6,033,880 A | 3/2000 | Haff et al. |
| 6,063,339 A | 5/2000 | Tisone et al. |
| 6,106,685 A | 8/2000 | McBride et al. |
| 6,130,098 A | 10/2000 | Handique et al. |
| 6,180,372 B1 | 1/2001 | Franzen |
| 6,210,891 B1 | 4/2001 | Nyren et al. |
| 6,258,568 B1 | 7/2001 | Nyren et al. |
| 6,294,063 B1 | 9/2001 | Becker et al. |
| 6,296,673 B1 | 10/2001 | Santarsiero et al. |
| 6,319,668 B1 | 11/2001 | Nova et al. |
| 6,379,929 B1 | 4/2002 | Burns et al. |
| 6,432,290 B1 | 8/2002 | Harrison et al. |
| 6,454,924 B2 | 9/2002 | Jedrzejewski et al. |
| 6,473,492 B2 | 10/2002 | Prins |
| 6,485,913 B1 | 11/2002 | Becker et al. |
| 6,538,823 B2 | 3/2003 | Kroupenkine et al. |
| 6,545,815 B2 | 4/2003 | Kroupenkine et al. |
| 6,565,727 B1 | 5/2003 | Shenderov |
| 6,596,238 B1 | 7/2003 | Belder et al. |
| 6,613,560 B1 | 9/2003 | Tso et al. |
| 6,629,826 B2 | 10/2003 | Yoon et al. |
| 6,630,006 B2 | 10/2003 | Santarsiero et al. |
| 6,665,127 B2 | 12/2003 | Bao et al. |
| 6,730,516 B2 | 5/2004 | Jedrzejewski et al. |
| 6,761,962 B2 | 7/2004 | Bentsen et al. |
| 6,773,566 B2 | 8/2004 | Shenderov |
| 6,790,011 B1 | 9/2004 | Le Pesant et al. |
| 6,808,934 B2 | 10/2004 | Mutz et al. |
| 6,828,100 B1 | 12/2004 | Ronaghi |
| 6,841,128 B2 | 1/2005 | Kambara et al. |
| 6,849,459 B2 | 2/2005 | Gilbert et al. |
| 6,855,881 B2 | 2/2005 | Khoshnood |
| 6,896,855 B1 | 5/2005 | Kohler et al. |
| 6,911,056 B2 | 6/2005 | Santarsiero et al. |
| 6,911,132 B2 | 6/2005 | Pamula et al. |
| 6,924,792 B1 | 8/2005 | Jessop |
| 6,932,845 B2 | 8/2005 | Santarsiero et al. |
| 6,949,176 B2 | 9/2005 | Vacca et al. |
| 6,951,575 B2 | 10/2005 | Santarsiero et al. |
| 6,958,132 B2 | 10/2005 | Chiou et al. |
| 6,960,437 B2 | 11/2005 | Enzelberger et al. |
| 6,977,033 B2 | 12/2005 | Becker et al. |
| 6,989,234 B2 | 1/2006 | Kolar et al. |
| 7,052,244 B2 | 5/2006 | Fouillet et al. |
| 7,078,168 B2 | 7/2006 | Sylvan |
| 7,163,612 B2 | 1/2007 | Sterling et al. |
| 7,189,359 B2 | 3/2007 | Yuan et al. |
| 7,189,560 B2 | 3/2007 | Kim et al. |
| 7,211,223 B2 | 5/2007 | Fouillet et al. |
| 7,251,392 B2 | 7/2007 | Kuiper et al. |
| 7,255,780 B2 | 8/2007 | Shenderov |
| 7,267,752 B2 | 9/2007 | King et al. |
| 7,310,080 B2 | 12/2007 | Jessop |
| 7,316,001 B2 | 1/2008 | Gold et al. |
| 7,328,979 B2 | 2/2008 | Decre et al. |
| 7,329,545 B2 | 2/2008 | Pamula et al. |
| 7,338,760 B2 | 3/2008 | Gong et al. |
| 7,438,856 B2 | 10/2008 | Jedrzejewski et al. |
| 7,439,014 B2 | 10/2008 | Pamula et al. |
| 7,454,988 B2 | 11/2008 | Tan |
| 7,458,661 B2 | 12/2008 | Kim et al. |
| 7,531,072 B2 | 5/2009 | Roux et al. |
| 7,547,380 B2 | 6/2009 | Velev |
| 7,556,776 B2 | 7/2009 | Fraden et al. |
| 7,569,129 B2 | 8/2009 | Pamula et al. |
| 7,579,172 B2 | 8/2009 | Cho et al. |
| 7,641,779 B2 | 1/2010 | Becker et al. |
| 7,727,466 B2 | 6/2010 | Meathrel et al. |
| 7,727,723 B2 | 6/2010 | Pollack et al. |
| 7,745,207 B2 | 6/2010 | Jovanovich et al. |
| 7,759,132 B2 | 7/2010 | Pollack et al. |
| 7,763,471 B2 | 7/2010 | Pamula et al. |
| 7,815,871 B2 | 10/2010 | Pamula et al. |
| 7,816,121 B2 | 10/2010 | Pollack et al. |
| 7,821,699 B1 | 10/2010 | Lo et al. |
| 7,822,510 B2 | 10/2010 | Paik et al. |
| 7,833,804 B2 | 11/2010 | Kawabata et al. |
| 7,851,184 B2 | 12/2010 | Pollack et al. |
| 7,901,947 B2 | 3/2011 | Pollack et al. |
| 7,919,330 B2 | 4/2011 | De Guzman et al. |
| 7,922,886 B2 | 4/2011 | Fouillet et al. |
| 7,939,021 B2 | 5/2011 | Smith et al. |
| 7,943,030 B2 | 5/2011 | Shenderov |
| 7,989,056 B2 | 8/2011 | Plissonnier et al. |
| 7,998,436 B2 | 8/2011 | Pollack |
| 8,007,739 B2 | 8/2011 | Pollack et al. |
| 8,041,463 B2 | 10/2011 | Pollack et al. |
| 8,048,628 B2 | 11/2011 | Pollack et al. |
| 8,075,754 B2 | 12/2011 | Sauter-Starace et al. |
| 8,137,917 B2 | 3/2012 | Pollack et al. |
| 8,147,668 B2 | 4/2012 | Pollack et al. |
| 8,221,605 B2 | 7/2012 | Pollack et al. |
| 8,236,156 B2 | 8/2012 | Sarrut et al. |
| 8,287,711 B2 | 10/2012 | Pollack et al. |
| 8,304,253 B2 | 11/2012 | Yi et al. |
| 8,313,698 B2 | 11/2012 | Pollack et al. |
| 8,342,207 B2 | 1/2013 | Raccurt et al. |
| 8,349,276 B2 | 1/2013 | Pamula et al. |
| 8,388,909 B2 | 3/2013 | Pollack et al. |
| 8,389,297 B2 | 3/2013 | Pamula et al. |
| 8,394,249 B2 | 3/2013 | Pollack et al. |
| 2001/0036669 A1 | 11/2001 | Jedrzejewski et al. |
| 2002/0005354 A1 | 1/2002 | Spence et al. |
| 2002/0036139 A1 | 3/2002 | Becker et al. |
| 2002/0043463 A1 | 4/2002 | Shenderov |
| 2002/0058332 A1 | 5/2002 | Quake et al. |
| 2002/0093651 A1 | 7/2002 | Roe |
| 2002/0125135 A1 | 9/2002 | Derand et al. |
| 2002/0128546 A1 | 9/2002 | Silver |
| 2002/0143437 A1 | 10/2002 | Handique et al. |
| 2002/0164812 A1 | 11/2002 | DeLucas |
| 2002/0168180 A1 | 11/2002 | Tol et al. |
| 2002/0168671 A1 | 11/2002 | Burns et al. |
| 2002/0172969 A1 | 11/2002 | Burns et al. |
| 2003/0006140 A1 | 1/2003 | Vacca et al. |
| 2003/0012483 A1 | 1/2003 | Ticknor et al. |
| 2003/0012699 A1 | 1/2003 | Moore et al. |
| 2003/0013203 A1 | 1/2003 | Jedrzejewski et al. |
| 2003/0036206 A1 | 2/2003 | Chien et al. |
| 2003/0049632 A1 | 3/2003 | Edman et al. |
| 2003/0082081 A1 | 5/2003 | Fouillet et al. |
| 2003/0103021 A1 | 6/2003 | Young et al. |
| 2003/0119057 A1 | 6/2003 | Gascoyne et al. |
| 2003/0138819 A1 | 7/2003 | Gong et al. |
| 2003/0164295 A1 | 9/2003 | Sterling |
| 2003/0183525 A1 | 10/2003 | Elrod et al. |
| 2003/0205632 A1 | 11/2003 | Kim et al. |
| 2003/0206351 A1 | 11/2003 | Kroupenkine |
| 2003/0224528 A1 | 12/2003 | Chiou et al. |
| 2003/0227100 A1 | 12/2003 | Chandross et al. |
| 2004/0007377 A1 | 1/2004 | Fouillet et al. |
| 2004/0014239 A1 | 1/2004 | Wolk et al. |
| 2004/0031688 A1 | 2/2004 | Shenderov |
| 2004/0042721 A1 | 3/2004 | Kroupenkine et al. |

| | | | |
|---|---|---|---|
| 2004/0055536 A1 | 3/2004 | Kolar et al. | |
| 2004/0055891 A1 | 3/2004 | Pamula et al. | |
| 2004/0058450 A1 | 3/2004 | Pamula | |
| 2004/0086870 A1 | 5/2004 | Tyvoll et al. | |
| 2004/0091392 A1 | 5/2004 | McBridge et al. | |
| 2004/0136876 A1 | 7/2004 | Fouillet et al. | |
| 2004/0141884 A1 | 7/2004 | Unno et al. | |
| 2004/0180346 A1 | 9/2004 | Anderson et al. | |
| 2004/0231987 A1 | 11/2004 | Sterling et al. | |
| 2004/0265171 A1 | 12/2004 | Pugia et al. | |
| 2005/0037507 A1 | 2/2005 | Gauer | |
| 2005/0048581 A1 | 3/2005 | Chiu et al. | |
| 2005/0056569 A1 | 3/2005 | Yuan et al. | |
| 2005/0064423 A1 | 3/2005 | Higuchi et al. | |
| 2005/0087122 A1 | 4/2005 | Ismagliov et al. | |
| 2005/0100675 A1 | 5/2005 | Mao et al. | |
| 2005/0106742 A1 | 5/2005 | Wahl | |
| 2005/0142563 A1 | 6/2005 | Haddad et al. | |
| 2005/0148042 A1 | 7/2005 | Prestwich et al. | |
| 2005/0158755 A1 | 7/2005 | Lee et al. | |
| 2005/0179746 A1 | 8/2005 | Roux et al. | |
| 2005/0227264 A1 | 10/2005 | Nobile et al. | |
| 2005/0282224 A1 | 12/2005 | Fouillet et al. | |
| 2005/0287572 A1 | 12/2005 | Mathies et al. | |
| 2006/0021875 A1 | 2/2006 | Griffith et al. | |
| 2006/0039823 A1 | 2/2006 | Yamakawa et al. | |
| 2006/0054503 A1 | 3/2006 | Pamula et al. | |
| 2006/0068450 A1 | 3/2006 | Combette et al. | |
| 2006/0132927 A1 | 6/2006 | Yoon | |
| 2006/0164490 A1 | 7/2006 | Kim et al. | |
| 2006/0166261 A1 | 7/2006 | Higuchi et al. | |
| 2006/0166262 A1 | 7/2006 | Higuchi et al. | |
| 2006/0172336 A1 | 8/2006 | Higuchi et al. | |
| 2006/0186048 A1 | 8/2006 | Tan | |
| 2006/0194331 A1 | 8/2006 | Pamula et al. | |
| 2006/0231398 A1 | 10/2006 | Sarrut et al. | |
| 2006/0254933 A1 | 11/2006 | Adachi et al. | |
| 2007/0023292 A1 | 2/2007 | Kim et al. | |
| 2007/0037294 A1 | 2/2007 | Pamula et al. | |
| 2007/0045117 A1 | 3/2007 | Pamula et al. | |
| 2007/0052781 A1 | 3/2007 | Fraden et al. | |
| 2007/0062583 A1 | 3/2007 | Cox et al. | |
| 2007/0064990 A1 | 3/2007 | Roth | |
| 2007/0086927 A1 | 4/2007 | Natarajan et al. | |
| 2007/0141593 A1 | 6/2007 | Lee et al. | |
| 2007/0207513 A1 | 9/2007 | Sorensen et al. | |
| 2007/0217956 A1 | 9/2007 | Pamula et al. | |
| 2007/0241068 A1 | 10/2007 | Pamula et al. | |
| 2007/0242105 A1 | 10/2007 | Srinivasan et al. | |
| 2007/0242111 A1 | 10/2007 | Pamula et al. | |
| 2007/0243634 A1 | 10/2007 | Pamula et al. | |
| 2007/0267294 A1 | 11/2007 | Shenderov | |
| 2007/0275415 A1 | 11/2007 | Srinivasan et al. | |
| 2008/0003142 A1 | 1/2008 | Link et al. | |
| 2008/0006535 A1 | 1/2008 | Paik et al. | |
| 2008/0023330 A1* | 1/2008 | Viovy et al. | 204/450 |
| 2008/0038810 A1 | 2/2008 | Pollack et al. | |
| 2008/0044893 A1 | 2/2008 | Pollack et al. | |
| 2008/0044914 A1 | 2/2008 | Pamula et al. | |
| 2008/0050834 A1 | 2/2008 | Pamula et al. | |
| 2008/0053205 A1 | 3/2008 | Pollack et al. | |
| 2008/0105549 A1 | 5/2008 | Pamela et al. | |
| 2008/0124252 A1 | 5/2008 | Marchand et al. | |
| 2008/0138815 A1 | 6/2008 | Brown et al. | |
| 2008/0142376 A1 | 6/2008 | Fouillet et al. | |
| 2008/0151240 A1 | 6/2008 | Roth | |
| 2008/0153091 A1 | 6/2008 | Brown et al. | |
| 2008/0160525 A1 | 7/2008 | Brown et al. | |
| 2008/0169184 A1 | 7/2008 | Brown et al. | |
| 2008/0171324 A1 | 7/2008 | Brown et al. | |
| 2008/0171325 A1 | 7/2008 | Brown et al. | |
| 2008/0171326 A1 | 7/2008 | Brown et al. | |
| 2008/0171327 A1 | 7/2008 | Brown et al. | |
| 2008/0171382 A1 | 7/2008 | Brown et al. | |
| 2008/0210558 A1 | 9/2008 | Sauter-Starace et al. | |
| 2008/0213766 A1 | 9/2008 | Brown et al. | |
| 2008/0247920 A1 | 10/2008 | Pollack et al. | |
| 2008/0264797 A1 | 10/2008 | Pamula et al. | |
| 2008/0274513 A1 | 11/2008 | Shenderov et al. | |
| 2008/0302431 A1 | 12/2008 | Marchand et al. | |
| 2008/0305481 A1 | 12/2008 | Whitman et al. | |
| 2009/0014394 A1 | 1/2009 | Yi et al. | |
| 2009/0042319 A1 | 2/2009 | De Guzman et al. | |
| 2009/0053726 A1 | 2/2009 | Owen et al. | |
| 2009/0127123 A1 | 5/2009 | Raccurt et al. | |
| 2009/0134027 A1 | 5/2009 | Jary | |
| 2009/0142564 A1 | 6/2009 | Plissonnier et al. | |
| 2009/0155902 A1 | 6/2009 | Pollack et al. | |
| 2009/0192044 A1 | 7/2009 | Fouillet | |
| 2009/0260988 A1 | 10/2009 | Pamula et al. | |
| 2009/0263834 A1 | 10/2009 | Sista et al. | |
| 2009/0280251 A1 | 11/2009 | De Guzman et al. | |
| 2009/0280475 A1 | 11/2009 | Pollack et al. | |
| 2009/0280476 A1 | 11/2009 | Srinivasan et al. | |
| 2009/0288710 A1 | 11/2009 | Viovy et al. | |
| 2009/0291433 A1 | 11/2009 | Pollack et al. | |
| 2010/0025242 A1 | 2/2010 | Pamula et al. | |
| 2010/0096266 A1 | 4/2010 | Kim | |
| 2010/0116640 A1 | 5/2010 | Pamula et al. | |
| 2010/0140093 A1 | 6/2010 | Pamula et al. | |
| 2010/0143963 A1 | 6/2010 | Pollack | |
| 2010/0258441 A1 | 10/2010 | Sista et al. | |
| 2010/0279374 A1 | 11/2010 | Sista et al. | |
| 2011/0100823 A1 | 5/2011 | Pollack et al. | |
| 2011/0114490 A1 | 5/2011 | Pamula et al. | |
| 2011/0147215 A1 | 6/2011 | Fuchs et al. | |
| 2011/0180571 A1 | 7/2011 | Srinivasan et al. | |
| 2011/0186433 A1 | 8/2011 | Pollack et al. | |
| 2011/0203930 A1 | 8/2011 | Pamula et al. | |
| 2011/0209998 A1 | 9/2011 | Shenderov | |
| 2012/0018306 A1 | 1/2012 | Srinivasan et al. | |
| 2012/0132528 A1 | 5/2012 | Shenderov et al. | |
| 2012/0165238 A1 | 6/2012 | Pamula et al. | |

FOREIGN PATENT DOCUMENTS

| | | | |
|---|---|---|---|
| FR | WO2006003292 A1 | 1/2006 | |
| WO | WO9822625 A1 | 5/1998 | |
| WO | WO9915876 A1 | 4/1999 | |
| WO | WO9917093 A1 | 4/1999 | |
| WO | WO9954730 A1 | 10/1999 | |
| WO | 2000069565 A1 | 11/2000 | |
| WO | 0073655 A1 | 12/2000 | |
| WO | 03051517 A2 | 6/2003 | |
| WO | WO03045556 A2 | 6/2003 | |
| WO | 2004029585 A1 | 4/2004 | |
| WO | 2004030820 | 4/2004 | |
| WO | 2004073863 A2 | 9/2004 | |
| WO | 2005047696 A1 | 5/2005 | |
| WO | 2006013303 A1 | 2/2006 | |
| WO | WO2006026351 A1 | 3/2006 | |
| WO | 2006070162 A1 | 7/2006 | |
| WO | 2006081558 | 8/2006 | |
| WO | 2006124458 A2 | 11/2006 | |
| WO | 2006127451 A2 | 11/2006 | |
| WO | 2006134307 A1 | 12/2006 | |
| WO | 2006138543 | 12/2006 | |
| WO | 2007003720 A1 | 1/2007 | |
| WO | 2007012638 A1 | 2/2007 | |
| WO | 2007033990 A1 | 3/2007 | |
| WO | 2007048111 | 4/2007 | |
| WO | 2007120240 A2 | 10/2007 | |
| WO | 2007120241 A2 | 10/2007 | |
| WO | 2007123908 A2 | 11/2007 | |
| WO | WO2007133710 A2 | 11/2007 | |
| WO | 2008051310 A2 | 5/2008 | |
| WO | 2008055256 A3 | 5/2008 | |
| WO | 2008068229 A1 | 6/2008 | |

OTHER PUBLICATIONS

U.S. Appl. No. 10/522,175, filed Jan. 24, 2005, entitled "Method and device for screening molecules in cells", which was based on International Application No. PCT/FR2003/002298.
""Chip juggles droplets"", Technology Research News, Sep. 4-11, 2002. Retrieved on Apr. 18, 2008 from: http://www.trnmag.com/Stories/2002/090402/Chip_juggles_droplets_090402.html.

(56) References Cited

OTHER PUBLICATIONS

""Laboratory on a Chip"", Popular Mechanics—Tech Watch, p. 25, Mar. 2002. Retrieved on Apr. 18, 2008 from: http://www.ee.duke.edu/research/microfluidics/images/PopMechArticle.JPG.

"Making materials fit the future: accommodating relentless technological requirements means researchers must recreate and reconfigure materials, frequently challenging established laws of physics, while keeping an eye on Moore's law", R&D Magazine Conference Handout, Dec. 2001.

Aldrich et al., "PathoFinder: Microscale PCR Based Virus Detection," Yale Department of Engineering Design Course Report, Dec. 2003.

Atencia, J. and D. Beebe, "Controlled microfluidic interfaces," Nature, vol. 437, pp. 648-655, Sep. 2005.

Chatterjee, Debalina. "Lab on a Chip Applications with a Digital Microfluidic Platform," UCLA Dissertation 2008, UMI Microform No. 3342975.

Chang, Yi-Hsien et al., "Integrated polymerase chain reaction chips utilizing digital microfluidics", Biomed Microdevices, vol. 8, pp. 215-225, 2006.

Cho et al., "Towards Digital Microfluidic Circuits: Creating, Transporting, Cutting and Merging Liquid Droplets by Electrowetting-Based Actuation," Proc. IEEE/Micro Electro Mechanical Systems Conference, pp. 32-35, 2002.

Colgate E, Matsumoto H, "An Investigation of Electrowetting-based Microactuation," Journal of Vacuum Science & Technology A—Vacuume Surfaces and Films, V. 8 (4): pp. 3625-3633, Jul.-Aug. 1990.

Jie Ding, "System level architectural optimization of semi-reconfigurable microfluidic system," M.S. Thesis, Duke University Dept of Electrical Engineering, 2000.

Shite-Kang Fan, "Digital Microfluidics by Cross-Reference EWOD Actuation: Principle, Device, and System," PhD Dissertation, University of California Dept. of Mechanical Engineering, 2003.

Kim, Chang-Jin et al., "U.S. Appl. No. 10/343,261 Electrowetting-Driven Micropumping," UCLA Invention Report, Amendment, Declaration including Invention Report, Petition for Extension of Time, and Authorization to Charge Deposit, submitted to USPTO on Feb. 4, 2005.

Kolar, P. and R.B. Fair, "Non contact electrostatic stamping for DNA microarray synthesis," smallTalk2001 Conference Program Abstract (Aug. 2001), p. 139.

Moon, Hyejin, Ph.D., "Electrowetting-on-dielectric microfluidics: Modeling, physics, and MALDI application," Ph.D. Dissertation, University of California, Dept. of Mechanical Engineering, Los Angeles, 2006.

Juergen Pipper et al., "Clockwork PCR Including Sample Preparation," Angew. Chem. Int. Ed., vol. 47, pp. 3900-3904, 2008.

Pollack et al., "Electrowetting-Based Actuation of Droplets for Integrated Microfluidics," Lab on a Chip (LOC), vol. 2, pp. 96-101, 2002.

Olivier Raccurt et al., "On the influence of surfactants in electrowetting systems," J. Micromech. Microeng., vol. 17, pp. 2217-2223 (2007).

Jean-Maxime Roux and Yves Fouillet, "3D droplet displacement in microfluidic systems by electrostatic actuation," Sensors and Actuators A, vol. 134, Issue 2, pp. 486-493, Mar. 15, 2007.

Seyrat E, Hayes RA, "Amorphous fluoropolymers as insulators for reversible low-voltage electrowetting," Journal of Applied Physics, vol. 90 (3): pp. 1383-1386, Aug. 1, 2001.

Vijay Srinivasan, Anand Jog and Richard B. Fair, "Scalable Macromodels for Microelectromechanical Systems," Technical Proc. 2001 Int. Conf. on Modeling and Simulation of Microsystems, pp. 72-75, 2001.

T. Taniguchi et al., "Chemical reactions in microdroplets by electrostatic manipulation of droplets in liquid media," Lab on a Chip, vol. 2, No. 2, pp. 19-23 (2002).

Torkkeli, Altti, "Droplet microfluidics on a planar surface," Doctoral Dissertation, Department of Electrical Engineering, Helsinki University of Technology (Oct. 3, 2003).

Tsuchiya, Hiroyoshi et al., "On-chip polymerase chain reaction microdevice employing a magnetic droplet-manipulation system", Sensors and Actuators B 130 pp. 583-588, 2007.

Vinet, F., et al., "Microarrays and microfluidic devices; miniaturized systems for biological analysis," Microelectronic Engineering 61-62 (2002) 41-47.

Masao Washizu, "Electrostatic Actuation of Liquid Droplets for Micro-Reactor Applications", IEEE Industry Applications Society Annual Meeting, pp. 1867-1873, Oct. 5-9, 1997.

""Chip mixes droplets faster"", MIT Technology Review, Oct. 2003. Retrieved on Apr. 18, 2008 from:http://www.trnmag.com/Stories/2003/102203/Chip_mixes_droplets_faster_Brief_102203.html.

Ali Agah, "DNA Analysis Chip by Electrowetting Actuation," Stanford Nanofabrication Facility, p. 9, 2002.

Bhansali et al., "Resolving chemical/bio-compatibility issues in microfluidic MEMS systems," SPIE Conference on Microfluidic Devices and Systems II, vol. 3877, Santa Clara, CA, pp. 101-109 (1999).

Cho et al., "Concentration and binary separation of micro particles for droplet-based digital microfluidics," Lab Chip, vol. 7, pp. 490-498, 2007.

Lehmann et al., "Droplet-Based DNA Purification in a Magnetic Lab-on-a-Chip," Angewandte Chemie, vol. 45, pp. 3062-3067, 2006.

N. Pamme, "Magnetism and microfluidics," Lab on a Chip (LOC), vol. 6, pp. 24-38, 2006.

Pollack et al., "Electrowetting-Based Microfluidics for High-Throughput Screening," smallTalk2001 Conference Program Abstract (Aug. 2001), p. 149, San Diego.

R. Sista, "Development of a Digital Microfluidic Lab-on-a-Chip for Automated Immunoassay with Magnetically Responsive Beads", PhD Thesis, Department of Chemical Engineering, Florida State University, 2007.

E. Verpoorte, "Beads and chips: new recipes for analysis," Lab on a Chip (LOC), vol. 3, pp. 60N-68N, 2003.

Wang et al., "Droplet-based micro oscillating-flow PCR chip," J. Micromechanics and Microengineering, vol. 15, pp. 1369-1377, 2005.

Weber, et al., "Specific Blood Purification by Means of Antibody-Conjugated Magnetic Microspheres", Centre for Biomedical Technology, Austria, Scientific and Clinical Applications of Magnetic Carriers, 1997.

Yi et al., "Geometric surface modification of nozzles for complete transfer of liquid drops," Solid-State Sensor, Actuator and Microsystems Workshop, pp. 164-167, Jun. 6-10, 2004.

Yoon et al., "Preventing Biomolecular Adsorption in Electrowetting-Based Biofluidic Chips", Analytical Chem. 75, 5097-5102 (2003).

Moon H, Cho SK, Garrell RL, et al., "Low voltage electrowetting-on-dielectric," Journal of Applied Physics, vol. 92 (7): pp. 4080-4087, Oct. 1, 2002.

U.S. Appl. No. 12/465,935 Rule 1.132 Declaration Gaurav Jitendra Shah, Jun. 30, 2011.

Al-Rubeai, et al., "The effect of Pluronic F-68 on hybridoma cells in continuous culture", Applied Microbiology and Biology 1992, pp. 44-45.

Furdui et al., "Immunomagnetic T cell capture from blood for PCR analysis using microfluidic systems", Miniaturisation for Chemistry, Biology & Bioengineering, Lab Chip 2004, 4, 614-618.

Liu et al., "Effect of Non-Ionic Surfactants on the Formation of DNA/Emulsion Complexes and Emulsion-Medicated Gene Transfer", Pharmaceutical Research, pp. 1642-1646, vol. 13, No. 11, 1996.

Yi, U.-C. and C.-J. Kim, "Characterization of electrowetting actuation on addressable single-side coplanar electrodes," Journal of Micromechanics and Microengineering, vol. 16, Oct. 2006, pp. 2053-2059.

Dubois, P., G. Marchand, Y. Fouillet, J. Berthier, T. Douki, F. Hassine, S. Gmouh, and M. Vaultier, "Ionic Liquid Droplet as e-Microreactor," Analytical Chemistry, vol. 78, 2006, pp. 4909-4917.

Whitesides, G.M., "The origins and the future of microfluidics," Nature, vol. 442, 2006, pp. 368-373.

Chin, C.D., V. Linder, and S.K. Sia, "Lab-on-a-chip devices for global health: past studies and future opportunities." Lab on a Chip, vol. 7, Jan. 2007, pp. 41-57.

(56) References Cited

OTHER PUBLICATIONS

Baviere, R., J. Boutet, and Y. Fouillet, "Dynamics of droplet transport induced by electrowetting actuation," Microfluidics and Nanofluidics, vol. 4, May. 2007, pp. 287-294.
Dewey A, Srinivasan V, Icoz E, "Visual modeling and design of microelectromechanical system transducers", Microelectronics Journal, vol. 32, pp. 373-381, Apr. 2001.
Dewey a, Srinivasan V, Icoz E, "Towards a visual modeling approach to designing micro electromechanical system transducers," Journal of Micromechanics and Microengineering, vol. 9, pp. 332-340, Dec. 1999.
R.B. Fair, A. Khlystov, T. Tailor, V. Ivanov, R.D. Evans, V. Srinivasan, V. Pamula, M.G. Pollack, P.B. Griffin, and J. Zhoud, "Chemical and Biological Applications of Digital Microfluidic Devices", IEEE Design and Test of Computers, vol. 24(1): pp. 10-24 Jan.-Feb. 2007.
R.B. Fair, A. Khlystov, V. Srinivasan, V. K. Pamula, K.N. Weaver, "Integrated chemical/biochemical sample collection, pre-concentration, and analysis on a digital microfluidic lab-on-a-chip platform," Lab-on-a-Chip: Platforms, Devices, and Applications, Conf. 5591, SPIE Optics East, Philadelphia, Oct. 25-28, 2004.
R.B. Fair, V. Srinivasan, H. Ren, P. Paik, V.K. Pamula, M.G. Pollack, "Electrowetting-based On-Chip Sample Processing for Integrated Microfluidics," IEEE Inter. Electron Devices Meeting (IEDM), pp. 32.5.1-32.5.4, 2003.
Phil Paik, Vamsee K. Pamula, and K. Chakrabarty, "Thermal effects on Droplet Transport in Digital Microfluidics with Applications to Chip Cooling Processing for Integrated Microfluidics," International Conference on Thermal, Mechanics, and Thermomechanical Phenomena in Electronic Systems (ITherm), pp. 649-654, 2004.
Phil Paik, Vamsee K. Pamula, and Richard B. Fair, "Rapid droplet mixers for digital microfluidic systems," Lab on a Chip, vol. 3, pp. 253-259, 2003.
Phil Paik, Vamsee K. Pamula, Michael G. Pollack and Richard B. Fair, "Electrowetting-based droplet mixers for microfluidic systems", Lab on a Chip (LOC), vol. 3, pp. 28-33, 2003.
Vamsee K. Pamula and Krishnendu Chakrabarty, "Cooling of integrated circuits using droplet-based microfluidics," Proc. ACM Great Lakes Symposium on VLSI, pp. 84-87, Apr. 2003.
V.K. Pamula, V. Srinivasan, H. Chakrapani, R.B. Fair, E.J. Toone, "A droplet-based lab-on-a-chip for colorimetric detection of nitroaromatic explosives," Proceedings of Micro Electro Mechanical Systems, pp. 722-725, 2005.
M. G. Pollack, P. Y. Paik, A. D. Shenderov, V. K. Pamula, F. S. Dietrich, and R. B. Fair, "Investigation of electrowetting-based microfluidics for real-time PCR applications," µTAS 2003.
Hong Ren, Vijay Srinivasan, Michael G. Pollack, and Richard B. Fair, "Automated electrowetting-based droplet dispensing with good reproducibility," Proc. Micro Total Analysis Systems (mTAS), pp. 993-996, 2003.
Hong Ren, Vijay Srinivasan, and Richard B. Fair, "Design and testing of an interpolating mixing architecture for electrowetting-based droplet-on-chip chemical dilution", Transducers 2003, pp. 619-622, 2003.
Vijay Srinivasan, Vamsee K. Pamula, Richard B. Fair, "An integrated digital microfluidic lab-on-a-chip for clinical diagnostics on human physiological fluids," Lab on a Chip, vol. 4, pp. 310-315, 2004.
Vijay Srinivasan, Vamsee K. Pamula, Richard B. Fair, "Droplet-based microfluidic lab-on-a-chip for glucose detection," Analytica Chimica Acta, vol. 507, No. 1, pp. 145-150, 2004.
V. Srinivasan, V.K. Pamula, P. Paik, and R.B. Fair, "Protein Stamping for MALDI Mass Spectrometry Using an Electrowetting-based Microfluidic Platform," Lab-on-a-Chip: Platforms, Devices, and Applications, Conf. 5591, SPIE Optics East, Philadelphia, Oct. 25-28, 2004.
Vijay Srinivasan, Vamsee K. Pamula, Michael G. Pollack, and Richard B. Fair, "Clinical diagnostics on human whole blood, plasma, serum, urine, saliva, sweat, and tears on a digital microfluidic platform," Proc. Micro Total Analysis Systems (mTAS), pp. 1287-1290, 2003.
Vijay Srinivasan, Vamsee K. Pamula, Michael G. Pollack, and Richard B. Fair, "A digital microfluidic biosensor for multianalyte detection", Proc. IEEE 16th Micro Electro Mechanical Systems Conference, pp. 327-330, 2003.
Vijay Srinivasan, Vamsee K. Pamula, K. Divakar Rao, Michael G. Pollack, Joseph A. Izatt, and Richard B. Fair, "3-D imaging of moving droplets for microfluidics using optical coherence tomography," Proc. Micro Total Analysis Systems (mTAS), pp. 1303-1306, 2003.
F. Su, S. Ozev and K. Chakrabarty, "Testing of droplet-based microelectrofluidic systems", Proc. IEEE International Test Conference, pp. 1192-1200, 2003.
Nicole Weaver, "Application of Magnetic Microspheres for Pyrosequencing on a Digital Microfluidic Platform", Aug. 2005.
Wheeler et al., "Electrowetting-on-dielectric for analysis of peptides and proteins by matrix assisted laser desorption/ionization mass spectrometry," Solid-State Sensor, Actuator and Microsystems Workshop publication, pp. 402-403, Jun. 6-10, 2004.
Aaron R. Wheeler, "Putting Electrowetting to Work," Science, vol. 322, No. 5901, pp. 539-540, Oct. 24, 2008.
Wheeler et al., Analytical Chemistry 2005, 76, pp. 4833-4838.
T.H. Zhang, K. Chakrabarty, R.B. Fair, "Behavioral modeling and performance evaluation of microelectrofluidics-based PCR systems using SystemC", IEEE Transactions on Computer-Aided Design of Integrated Circuits & Systems, vol. 23 (6): pp. 843-858, Jun. 2004.
Terry, S.C., J.H. Jerman, and J.B. Angell, "A Gas Chromatographic Air Analyzer Fabricated on a Silicon Wafer," IEEE Transactions on Electron Devices, vol. ED-26, 1979, pp. 1880-1886.
Tuckerman, D.B. And R.F.W. Pease, "High-Performance Heat Sinking for VLSI,"IEEE Electron Device Letters, 1981, pp. 126-129.
Batchelder, J.S., "Dielectrophoretic manipulator," Review of Scientific Instruments, vol. 54, 1983, pp. 300-302.
Manz, A., N. Graber, and H.M. Widmer, "Miniaturized Total Chemical Analysis Systems: a Novel Concept for Chemical Sensing," Sensors and Actuators B: Chemical, 1990, pp. 244-248.
Welters, W.J.J. and L.G.J. Fokkink, "Fast Electrically Switchable Capillary Effects," Langmuir, vol. 14, Mar. 1998, pp. 1535-1538.
McDonald, J.C., D.C. Duffy, J.R. Anderson, D.T. Chiu, H. Wu, O.J.A. Schuueller, and G.M. Whitesides, "Fabrication of Microfluidic systems in poly (dimethylsiloxane)," Electrophoresis, vol. 21, 2000, pp. 27-40.
A. Wego, S. Richter, L. Pagel, "Fluidic microsystems based on printed circuit board technology," Journal of Micromechanics and Microengineering, vol. 11, No. 5, pp. 528-531 (Sep. 2001).
Locascio, L.E., et al. "Polymer microfluidic devices," Talanta, vol. 56, Feb. 2002, pp. 267-287.
Garrell, R.L. et al., "Preventing Biomolecular Adsorption in Electrowetting-Based Biofluidic Chips," Analytical Chemistry, vol. 75, Oct. 2003, pp. 5097-5102.
P.Y. Chiou, H. Moon, H. Toshiyoshi, C.-J. Kim, and M.C. Wu, "Light actuation of liquid by optoelectrowetting," Sensors and Actuators A: Physical, vol. 104, May. 2003, pp. 222-228.
Squires, T.M. and S.R. Quake, "Microfluidics: Fluid physics at the nanoliter scale," Reviews of Modern Physics, vol. 77, Oct. 2005, pp. 977-1-26.
Fouillet, Y., D. Jary, A.G. Brachet, C. Chabrol, J. Boutet, P. Clementz, R. Charles, and C. Peponnet, "Design and Validation of a Complex Generic Fluidic Microprocessor Based on EWOD Droplet for Biological Applications," 9th International Conference on Miniaturized Systems for Chemistry and Life Sciences (MicroTAS), Boston, MA: 2005, pp. 58-60.
Z. Guttenberg, H. Muller, H. Habermuller, A. Geisbauer, J. Pipper, J. Felbel, M. Kielpinski, J. Scriba, and A. Wixforth, "Planar chip devices for PCR and hybridization with surface acoustic wave pump.," Lab on a chip, vol. 5, Mar. 2005, pp. 12617-22.
Yager, P., T. Edwards, E. Fu, K. Helton, K. Nelson, M.R. Tam, and B.H. Weigl, "Microfluidic diagnostic technologies for global public health," Nature, vol. 442, 2006, pp. 412-418.
Cooney, C.G., C-Y. Chen, M.R. Emerling, A Nadim, and J.D. Sterling, Microfluidics and Nanofluidics, vol. 2 Mar. 2006, pp. 435-446.
Chatterjee, D., B. Hetayothin, A.R. Wheeler, D.J. King, and R.L. Garrell, "Droplet-based microfluidics with nonaqueous solvents and solutions.," Lab on a Chip, vol. 6, Feb. 2006, pp. 199-206.

(56) References Cited

OTHER PUBLICATIONS

M. Madou, J. Zoval, G. Jia, H. Kido, J. Kim, "Lab on a CD," Annual Review of Biomedical Engineering, vol. 8, pp. 601-28, 2006.
Chakrabarty, "Automated Design of Microfluidics-Based Biochips: connecting Biochemistry of Electronics CAD", IEEE International Conference on Computer Design, San Jose, CA, Oct 1-4, 2006, 93-100.
Chakrabarty et al., "Design Automation Challenges for Microfluidics-Based Biochips", DTIP of MEMS & MOEMS, Montreux, Switzerland, Jun. 1-3, 2005.
Chakrabarty et al., "Design Automation for Microfluidics-Based Biochips", ACM Journal on Engineering Technologies in Computing Systems, 1(3), Oct. 2005, 186-223.
Chakrabarty, "Design, Testing, and Applications of Digital Microfluidics-Based Biochips", Proceedings of the 18th International Conf. on VLSI held jointly with 4th International Conf. on Embedded Systems Design (VLSID'05), IEEE, Jan. 3-7, 2005.
Chen et al., "Development of Mesoscale Actuator Device with Micro Interlocking Mechanism", J. Intelligent Material Systems and Structures, vol. 9, No. 4, Jun. 1998, pp. 449-457.
Chen et al., "Mesoscale Actuator Device with Micro Interlocking Mechanism", Proc. IEEE Micro Electro Mechanical Systems Workshop, Heidelberg, Germany, Jan. 1998, pp. 384-389.
Chen et al., "Mesoscale Actuator Device: Micro Interlocking Mechanism to Transfer Macro Load", Sensors and Actuators, vol. 73, Issues 1-2, Mar. 1999, pp. 30-36.
Fair et al., "A Micro-Watt Metal-Insulator-Solution-Transport (MIST) Device for Scalable Digital Bio-Microfluidic Systems", IEEE IEDM Technical Digest, 2001, 16.4.1-4.
Fair et al., "Advances in droplet-based bio lab-on-a-chip", BioChips 2003, Boston, 2003.
Fair et al., "Bead-Based and Solution-Based Assays Performed on a Digital Microfluidic Platform", Biomedical Engineering Society (BMES) Fall Meeting, Baltimore, MD, Oct. 1, 2005.
Fair, "Biomedical Applications of Electrowetting Systems", 5th International Electrowetting Workshop, Rochester, NY, May 31, 2006.
Fair et al., "Chemical and biological pathogen detection in a digital microfluidic platform", DARPA Workshop on Microfluidic Analyzers for DoD and National Security Applications, Keystone, CO, 2006.
Fair, "Droplet-based microfluidic Genome sequencing", NHGRI PI's meeting, Boston, 2005.
Jun et al., "Valveless Pumping using Traversing Vapor Bubbles in Microchannels", J. Applied Physics, vol. 83, No. 11, Jun. 1998, pp. 5658-5664.
Kim et al., "MEMS Devices Based on the Use of Surface Tension", Proc. Int. Semiconductor Device Research Symposium (ISDRS'99), Charlottesville, VA, Dec. 1999, pp. 481-484.
Kim, "Microelectromechanical Systems (MEMS) at the UCLA Micromanufacturing Lab", Dig. Papers, Int. Microprocesses and Nanotechnology Conf. (MNC'98), Kyungju, Korea, Jul. 1998, pp. 54-55.
Kim et al., "Micromachines Driven by Surface Tension", AIAA 99-3800, 30th AIAA Fluid Dynamics Conference, Norfolk, VA, (Invited lecture), Jun. 1999, pp. 1-6.
Lee et al., "Microactuation by Continuous Electrowetting Phenomenon and Silicon Deep Rie Process", Proc. MEMS (DSC—vol. 66) ASME Int. Mechanical Engineering Congress and Exposition, Anaheim, CA, Nov. 1998, 475-480.
Lee et al., "Liquid Micromotor Driven by Continuous Electrowetting", Proc. IEEE Micro Electro Mechanical Systems Workshop, Heidelberg, Germany, Jan. 1998, pp. 538-543.
Paik, "Adaptive Hot-Spot Cooling of Integrated Circuits Using Digital Microfluidics", Dissertation, Dept. of Electrical and Computer Engineering, Duke University, Apr. 25, 2006, 1-188.
Paik et al., "Adaptive hot-spot cooling of integrated circuits using digital microfluidics", Proceedings ASME International Mechanical Engineering Congress and Exposition, Orlando, Florida, USA. IMECE2005-81081, Nov. 5-11, 2005, 1-6.

Paik et al., "Coplanar Digital Microfluidics Using Standard Printed Circuit Board Processes", 9th International Conference on Miniaturized Systems for Chemistry and Life Sciences (MicroTAS), Boston, MA; POSTER, 2005.
Paik et al., "Coplanar Digital Microfluidics Using Standard Printed Circuit Board Processes", 9th Intl Conf. on Miniaturized Systems for Chemistry and Life Sciences, Boston, MA, Oct. 9-13, 2005, 566-68.
Paik et al., "Droplet-Based Hot Spot Cooling Using Topless Digital Microfluidics on a Printed Circuit Board", Int'l Workshops on Thermal Investigations of ICs and Systems (THERMINIC), 2005, 278-83.
Paik et al., "Electrowetting-based droplet mixers for microfluidic systems", Lab on a Chip (LOC), vol. 3. (more mixing videos available, along with the article, at LOC's website), 2003, 28-33.
Paik et al., "Rapid Droplet Mixers for Digital Microfluidic Systems", Masters Thesis, Duke Graduate School, 2002, 1-82.
Paik et al., "Rapid droplet mixers for digital microfluidic systems", Lab on a Chip, vol. 3. (More mixing videos available, along with the article, at LOC's website.), 2003, 253-259.
Paik et al., "Thermal effects on Droplet Transport in Digital Microfluids with Application to Chip Cooling Processing for Integrated Microfluidics", International Conference on Thermal, Mechanics, and Thermomechanical Phenomena in Electronic Systems (ITherm), 2004, 649-654.
Pamula, "A digital microfluidic platform for multiplexed explosive detection", Chapter 18, Electronics Noses and Sensors for the Detection of Explosives, Eds., J.W. Gardner and J. Yinon, Kluwer Academic Publishers, 2004.
Pamula et al., "Digital microfluidic lab-on-a-chip for protein crystallization", 5th Protein Structure Initiative "Bottlenecks" Workshop, NIH, Bethesda, MD, Apr. 13-14, 2006, 1-16.
Pamula et al., "Digital Microfluidics Platform for Lab-on-a-chip applications", Duke University Annual Post Doctoral Research Day, 2002.
Pamula et al., "Microfluidic electrowetting-based droplet mixing", IEEE, 2002, 8-10.
Pamula et al., "Digital Microfluidics for Lab-on-a-Chip Applications", "Emerging CAD Challenges for Biochip Design" Workshop, Conference on Design, Automation, and Test in Europe, Munich, Germany, Advance Programme, 2006, pp. 85-87.
Pollack et al., "Electrowetting-based actuation of liquid droplets for microfluidic applications", Appl. Phys. Letters, vol. 77, No. 11, Sep. 11, 2000, 1725-1726.
Pollack, "Electrowetting-based Microactuation of Droplets for Digital Microfluidics", PhD Thesis, Department of Electrical and Computer Engineering, Duke University, 2001.
Ren et al., "Automated on-chip droplet dispensing with volume control by electro-wetting actuation and capacitance metering", Sensors and Actuators B: Chemical, vol. 98, Mar. 2004, 319-327.
Ren et al., "Dynamics of electro-wetting droplet transport", Sensors and Actuators B (Chemical), vol. B87, No. 1, Nov. 15, 2002, 201-206.
Ren et al., "Micro/Nano Liter Droplet Formation and Dispensing by Capacitance Metering and Electrowetting Actuation", IEEE-NANO, 2002, 369-372.
Sherman et al., "Flow Control by Using High-Aspect-Ratio, In-Plane Microactuators", Sensors and Actuators, vol. 73, 1999, pp. 169-175.
Sherman et al., "In-Plane Microactuator for Fluid Control Application", Proc. IEEE Micro Electro Mechanical Systems Workshop, Heidelberg, Germany, Jan. 1998, pp. 454-459.
Srinivasan, "A Digital Microfluidic Lab-on-a-Chip for Clinical Diagnostic Applications", Ph.D. thesis, Dept of Electrical and Computer Engineering, Duke University, 2005.
Su et al., "Yield Enhancement of Digital Microfluidics-Based Biochips Using Space Redundancy and Local Reconfiguration", Proc. Design, Automation and Test in Europe (DATE) Conf., IEEE, 2005, 1196-1201.
Sudarsan et al., "Printed circuit technology for fabrication of plastic based microfluidic devices", Analytical Chemistry vol. 76, No. 11, Jun. 1, 2004, Previously published on-line, May 2004, 3229-3235.
Yao et al., "Spot Cooling Using Thermoelectric Microcooler", Proc. 18th Int. Thermoelectric Conf, Baltimore, VA, pp. 256-259, Aug. 1999.

(56) References Cited

OTHER PUBLICATIONS

Yi et al., "EWOD Actuation with Electrode-Free Cover Plate", Digest of Tech. papers, 13th International Conference on Solid-State Sensors, Actuators and Microsystems (Transducers '05), Seoul, Korea, Jun. 5-9, 2005, 89-92.

Yi, "Soft Printing of Biological Liquids for Micro-arrays: Concept, Principle, Fabrication, and Demonstration", Ph.D. dissertation, UCLA, 2004.

Yi et al., "Soft Printing of Droplets Digitized by Electrowetting", Transducers 12th Int'l Conf. on Solid State Sensors, Actuators and Microsystems, Boston, Jun. 8-12, 2003, 1804-1807.

Yi et al., "Soft Printing of Droplets Pre-Metered by Electrowetting", Sensors and Actuators A: Physical, vol. 114, Jan. 2004, 347-354.

Zeng et al., "Actuation and Control of Droplets by Using Electrowetting-on-Dielectric", Chin. Phys. Lett., vol. 21(9), 2004, 1851-1854.

Zhao et al., "In-droplet particle separation by travelling wave dielectrophoresis (twDEP) and EWOD", Solid-State Sensor, Actuators and Microsystems Workshop (Hilton Head '06), Hilton Head Island, SC, Jun. 2006, 181-184.

Zhao et al., "Micro air bubble manipulation by electrowetting on dielectric (EWOD): transporting, splitting, merging and eliminating of bubbles", Lab on a chip, vol. 7, 2007, First published as an Advance Article on the web, Dec. 4, 2006, 273-280.

PCT International Preliminary Report on Patentability for PCT/US2005/030247 dated Feb. 28, 2007.

PCT International Search Report and Written Opinion for PCT/US2006/047486 dated May 2, 2008.

PCT International Search Report and Written Opinion for PCT/US2006/047481 dated May 5, 2008.

PCT International Search Report and Written Opinion for PCT/US2007/011298 dated Jun. 25, 2008.

PCT International Search Report and Written Opinion for PCT/US2007/009379 dated Aug. 18, 2008.

Fowler, "Lab-on-a-Chip Technology May Present New ESD Challenges", Electrostatic Discharge Journal, Mar. 2002.

Chayen et al., "An automated system for micro-batch protein crystallization and screening," Journal of Applied Crystallography, 23, 297-302, 1990.

Krupka et al., "The high-speed Hydra-Plus-One system for automated high-throughput protein crystallography," Acta Crystallographica, D58, 1523-1526, 2002.

Saridakis et al., "Phase Diagram and Dilution Experiments in the Crystallization of Carboxypeptidase G2," Acta Crystallographica, D50, 293-297, 1994.

Jancarik et al., "Sparse matrix sampling: a screening method for the crystallization of macromolecules," Journal of Applied Crystallography, 24, 409, 1991.

Minkel. 2004. Microfluidics Goes Mainstream. Drug Discovery and Development. Jun. 2004.

Tulsi. 2004. Liquid Handling Systems Get Smaller, Smarter, Speedier. Drug Discovery and Development, Jan. 2004.

McPherson, "Crystallization of macromolecules—General principles," Methods in Enzymology A, 114, pp. 112-120, 1985.

Auroux et al., "Micro Total Analysis Systems. 2 Analytical Standard Operations and Applications," Analytical Chemistry, 74(12), 2637-2652, 2002.

Bodenstaff et al., "The prospects of nanocrystallography," Acta Crystallographica Section D, Biological Crystallography, D58, 1901-1906, 2002.

Chayen, "Protein crystallization for genomics: throughput vs. output," Journal of Structural and Functional Genomics 4: 115-120 (2003).

Chayen, "Recent advances in methodology for the crystallization of biological macromolecules," Journal of Crystal Growth, 198/199, 649-655, 1999.

Cudney et al., Screening and optimization strategies for macromolecular crystal growth, Acta Cryst. (1994) D50, 414-423.

Luft et al., "Macromolecular crystallization in a high throughput laboratory—the search phase," Journal of Crystal Growth, 232, 591-595, 2001.

Luft et al., "Microbatch macromolecular crystallization in micropipettes," Journal of Crystal Growth, 196, 450-455, 1999.

Reyes et al., "Micro Total Analysis Systems. 1. Introduction, Theory, and Technology," Analytical Chemistry, 74(12), 2623-2636, 2002.

Roach et al., "Controlling Nonspecific Protein Adsorption in a Plug-Based Microfluidic System by Controlling Interfacial Chemistry Using Fluorous-Phase Surfactants," Analytical Chemistry, vol. 77, No. 3, pp. 785-796, Feb. 1, 2005.

Sanjoh et al., "Spatiotemporal protein crystal growth studies using microfluidic silicon devices," Journal of Crystal Growth, 196, 691-702, 1999.

Schulte et al., "Interaction of Radicicol with Members of the Heat Shock Protein 90 Family of Molecular Chaperones," Molecular Endocrinology 13 (9): 1435-1448, 1999.

Yamada et al., "Microfluidic reactor array for high-throughput screenings of protein crystallization conditions," Proc. of micro Total Analysis Systems 2003, 449-452, 2003.

Hirano et al. "Protein Crystallization Device Using Electrostatic Micromanipulation," Proc. Of Micro Total Analysis Systems, Oct. 5-9, 2003, 473-476).

Hirano et al. "A Droplet-based Protein Crystallization Device Using Electrostatic Micromanipulation," Proc. Of Micro Total Analysis Systems, Sep. 26-30, 2004, 148-150).

Zheng et al. "A Droplet-Based, Composite PDMS/Glass Capillary Microfluic System for Evaluating Protein Crystallization Conditions by Microbatch and Vapor-Diffusion Methods with On-Chip X-Ray Diffraction," Angew. Chem. Int. Ed. 2004, 43, 2508-2511).

Zheng et al. "Screening of Protein Crystallization Conditions on a Microfluidic Chip Using Nanoliter-Size Droplets," J. Am. Chem. Soc. 2003, 125, 11170-11171).

\* cited by examiner

SAMPLE PROCESSING DROPLET ACTUATOR, SYSTEM AND METHOD

1 RELATED APPLICATIONS

This application is a continuation of U.S. patent application Ser. No. 11/839,786, entitled "Sample Processing Droplet Actuator, System and Method" filed Aug. 16, 2007, which is a continuation of International Patent Application No. PCT/US2007/09379, entitled "Droplet-Based Multiwell Operations," filed Apr. 18, 2007, which claims the benefit of, is related to, and incorporates by reference related provisional U.S. Patent Application No. 60/745,049, entitled "Apparatus and Methods for Droplet-Based Protein Crystallization," filed on Apr. 18, 2006; 60/745,054, entitled "Droplet-Based Multi-Well Plate," filed on Apr. 18, 2006; and 60/806,400, entitled "Droplet-Microactuator Stamping Platform," filed on Jun. 30, 2006.

2 FIELD OF THE INVENTION

The present invention broadly relates to a sample processing droplet actuator, system and method. Embodiments of the present invention relate to devices, systems and methods for stamping samples on a substrate, e.g., for MALDI-TOF analysis.

3 BACKGROUND OF THE INVENTION

3.1 Protein Crystallization Approaches

Protein expression and purification is an expensive process, and it is sometimes difficult to express proteins in large quantities. A large amount of expensive protein is required to establish conditions for crystallization. Consequently, there is a need to reduce the amount of protein required for crystallization screening and to do it more efficiently and at lower cost.

3.1.1 Protein Crystal Synthesis

Proteins play a key role in all biological processes. The specific biological function of a protein is determined by the three-dimensional (3D) arrangement of the constituent amino acids. Understanding a protein's 3D structure plays an important role in protein engineering, bioseparations, rational drug design, controlled drug delivery, and the design of novel enzyme substrates, activators, and inhibitors. Protein crystallization is a multi-parametric process that involves the steps of nucleation and growth, during which molecules are brought into a thermodynamically unstable and a supersaturated state.

3.1.2 Miniaturization and Automation of Protein Crystallization Setup

Many proteins of interest are unfortunately available only in limited supply. Efforts are ongoing to reduce the consumption of proteins by miniaturizing the crystallization setup. Despite efforts to reduce the protein volumes, these processes still consume significant amount of protein and are still labor-intensive.

Existing semi-automatic systems do not encompass ideal high-throughput configurations. They require user intervention for multiple tray processing and have other material processing issues. As most of the work performed with these systems is not on a large scale, automation of storage and handling of plates was not addressed in these systems. Even though these industrial systems are capable of setting up thousands of crystallization screens a day, they are prohibitively expensive for academic research labs. There remains a need in the art for a system that provides the high-throughput automation functionality of an industrial system at an affordable cost for small laboratories or individual investigators.

3.1.3 Lab-on-a-Chip Technologies

Microfluidic systems can be broadly categorized into continuous-flow and discrete-flow based systems. As the name suggests, continuous-flow systems rely on continuous flow of liquids in channels whereas discrete-flow systems utilize droplets of liquid within channels or in an architecture without channels. A common limitation that continuous flow systems face is that liquid transport is physically confined to fixed channels. The transport mechanisms used are usually pressure-driven by external pumps or electrokinetically-driven by high-voltages. These approaches involve complex channeling and require large supporting instruments in the form of external valves or power supplies. These restrictions make it difficult to achieve high degrees of functional integration and control in conventional continuous-flow systems.

3.2 Multi-Well Plates

Microfluidic technologies are attracting attention in pharmaceutical research, as miniaturization of assay volume and improvement of automation, throughput and precision become more critical in drug discovery research. Examples of recent microfluidic technologies and products include the Topaz™ system for protein crystallization from Fluidigm Corporation (San Francisco, Calif.), the LabChip® system from Caliper Life Sciences (Hopkinton, Mass.), and the LabCD™ system from Tecan Systems Inc. (San Jose, Calif.), both for ADME. These systems perform certain assays using small volumes of liquid. However, none of them even remotely approaches the flexibility of conventional robotic systems. This inadequacy results from inherent technical limitations associated with the way in which fluid handling is implemented in these devices.

Most existing technologies are based on a continuous-flow approach. Liquid is pumped (generally unidirectionally) through a network of microchannels using external pumps, valves, high-voltage supplies or centrifugal force. The primary disadvantage of all of these continuous-flow microfluidic devices is their architectural and operational rigidity. Most are optimized for a particular assay, providing little or no flexibility to make changes in reaction protocols. The required continuity of fluid in these devices also makes independent operation of different areas of the chip an inherently difficult proposition. Consequently, these technologies are non-modular and difficult to scale.

There is a need in the art for a microfluidic platform that avoids the use of a continuous-flow approach. There is a need for a system that affords flexibility and programmability that is comparable to robotic systems. Further, there is a need for a system that is capable of working with droplets as small as a few nanoliters in volume and avoids the requirements for a network of microchannels, external pumps, valves, high-voltage supplies and/or centrifugal force. Further, there is a need for a system that is scalable, permitting hundreds or even hundreds of thousands of droplets of liquid to be processed in parallel. Finally, there is a need for a system that is both compact and inexpensive to manufacture.

3.3 Protein Stamping Platforms

Mass spectroscopy (MS) is increasingly becoming the method of choice for protein analysis in biological samples. Among the various MS methods, MALDI-TOF (Matrix Assisted Laser Desorption-Ionization Time of Flight) is the most commonly used due to its simplicity, high sensitivity and resolution. A typical MALDI-MS protocol for protein identification involves sample preparation, stamping onto a MALDI target and analysis on a MALDI-TOF mass spectrometer. Sample preparation steps (such as digestion and concentration) are usually done in the well-plate format and last for several hours at the least. The stamping is accomplished using complex robotic systems which are huge, expensive and immobile. Required sample volumes are also very high, which is a concern for proteins available in very small quantities. Existing microfluidic devices are based on continuous flow in fixed microchannels, offering very little flexibility in terms of scalability and reconfigurability. As such, a need exists for a droplet microactuation stamping platform designed to solve the deficiencies found in the prior art.

4 BRIEF DESCRIPTION OF THE INVENTION

Embodiments of the present invention relate to a sample processing droplet actuator, system and method.

According to one embodiment, a stamping device comprising a droplet microactuator is provided and comprises: (a) a first plate comprising a path or network of control electrodes for transporting droplets on a surface thereof; (b) a second plate mounted in a substantially parallel orientation with respect to the first plate providing an interior volume between the plates, the second plate comprising one or more stamping ports for transporting some portion or all of a droplet from the interior volume to an exterior location; (c) a port for introducing fluid into the interior volume between the plates; and (d) a path or network of reference electrodes corresponding to the path or network of control electrodes.

According to another embodiment, a system is provided and comprises: (a) the stamping device as described above; (b) a computer processor electronically coupled to the stamping device and programmed to effect control of droplet operations on the stamping device; (c) one or more input devices electronically coupled to the computer processor; and (d) one or more output devices electronically coupled to the computer processor.

According to yet another embodiment, a method is provided and comprises employing the system as described above to deliver one or more MALDI-ready droplets to a MALDI substrate.

5 DEFINITIONS

As used herein, the following terms have the meanings indicated.

"Activate" with reference to one or more electrodes means effecting a change in the electrical state of the one or more electrodes which results in a droplet operation.

"Analyte," means a target substance for detection which may be present in a sample. Illustrative examples include antigenic substances, haptens, antibodies, proteins, peptides, amino acids, nucleotides, nucleic acids, drugs, ions, salts, small molecules, and cells.

"Bead," with respect to beads on a droplet microactuator, means any bead or particle capable of interacting with a droplet on or in proximity with a droplet microactuator. Beads may be any of a wide variety of shapes, such as spherical, generally spherical, egg shaped, disc shaped, cubical and other three dimensional shapes. The bead may, for example, be capable of being transported in a droplet on a droplet microactuator; configured with respect to a droplet microactuator in a manner which permits a droplet on the droplet microactuator to be brought into contact with the bead, on the droplet microactuator and/or off the droplet microactuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or only one component of a bead. The remainder of the bead may include, among other things, polymeric material, coatings, and moieties which permit attachment of an assay reagent. Examples of suitable magnetically responsive beads are described in U.S. Patent Publication No. 2005-0260686, "Multiplex flow assays preferably with magnetic particles as solid phase," published on Nov. 24, 2005, the entire disclosure of which is incorporated herein by reference for its teaching concerning magnetically responsive materials and beads.

"Communicate" (e.g., a first component "communicates with" or "is in communication with" a second component) is used herein to indicate a structural, functional, mechanical, optical, electrical, or fluidic relationship, or any combination thereof, between two or more components or elements. As such, the fact that one component is said to communicate with a second component is not intended to exclude the possibility that additional components may be present between and/or operatively associated or engaged with, the first and second components.

"Chip" refers to any substrate including not only silicon or semiconductors but glass, printed circuit boards, plastics or any other substrate on which the droplets are manipulated.

"Droplet" means a volume of liquid on a droplet microactuator which is at least partially bounded by filler fluid. For example, a droplet may be completely surrounded by filler fluid or may be bounded by filler fluid and one or more surfaces of the droplet microactuator. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet microactuator.

"Droplet operation" means any manipulation of a droplet on a droplet microactuator. A droplet operation may, for example, include: loading a droplet into the droplet microactuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet microactuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to size of the resulting droplets (i.e., the size of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading.

"Electronically coupled" is used herein to indicate an electrical or data relationship between two or more components or elements. As such, the fact that a first component is said to be electronically coupled to a second component is not intended to exclude the possibility that additional components may be present between, and/or operatively associated or engaged with, the first and second components. Further, electrically coupled components may in some embodiments include wireless intervening components.

"Input device" is used broadly to include all possible types of devices and ways to input information into a computer system or onto a network. Examples include stylus-based devices, pen-based devices, keyboard devices, keypad devices, touchpad devices, touch screen devices, joystick devices, trackball devices, mouse devices, bar-code reader devices, magnetic strip reader devices, infrared devices, speech recognition technologies.

"Output device" is used broadly to include all possible types of devices and ways to output information or data from a computer system to a user or to another system. Examples include visual displays, LEDs, printers, speakers, modems and wireless transceivers.

"Protocol" means a series of steps that includes, but is not limited to, droplet operations on one or more droplet micro actuators.

"Surface" with reference to immobilization of a molecule, such as an antibody or in analyte, on the surface, means any surface on which the molecule can be immobilized while retaining the capability to interact with droplets on a droplet microactuator. For example, the surface may be a surface on the droplet microactuator, such as a surface on the top plate or bottom plate of the droplet microactuator; a surface extending from the top plate or bottom plate of the droplet microactuator; a surface on a physical object positioned on the droplet microactuator in a manner which permits it to interact with droplets on the droplet microactuator; and/or a bead positioned on the droplet microactuator, e.g., in a droplet and/or in a droplet microactuator but exterior to the droplet.

The terms "top" and "bottom" are used throughout the description with reference to the top and bottom substrates of the droplet microactuator for convenience only, since the droplet microactuator is functional regardless of its position in space.

When a given component such as a layer, region or substrate is referred to herein as being disposed or formed "on" another component, that given component can be directly on the other component or, alternatively, intervening components (for example, one or more coatings, layers, interlayers, electrodes or contacts) can also be present. It will be further understood that the terms "disposed on" and "formed on" are used interchangeably to describe how a given component is positioned or situated in relation to another component. Hence, the terms "disposed on" and "formed on" are not intended to introduce any limitations relating to particular methods of material transport, deposition, or fabrication.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet microactuator, it should be understood that the droplet is arranged on the droplet microactuator in a manner which facilitates using the droplet microactuator to conduct droplet operations on the droplet, the droplet is arranged on the droplet microactuator in a manner which facilitates sensing of a property of or a signal from the droplet, and/or the droplet has been subjected to a droplet operation on the droplet microactuator.

6 BRIEF DESCRIPTION OF THE DRAWINGS

7 DETAILED DESCRIPTION OF THE INVENTION

The present invention relates to droplet-based protein crystallization involving a screening chip for varying protein crystallization conditions and an optimization chip which can be used to set up multiple conditions around a screening condition to identify optimal conditions for crystallization. The present invention also relates to a droplet-based multiwell plate involving integrated fluid handling capability, such as in a planar multiwell plate format. The present invention further relates to a droplet-microactuator stamping platform involving devices, systems and methods for stamping samples on a substrate. Further details of these aspects, as well as droplet microactuator architecture and operations, systems, kits, and other aspects of the present invention follows hereinbelow.

7.1 Droplet-Based Protein Crystallization Overview

One aspect of the present invention provides a chip for identification of crystallization conditions for target molecules, such as proteins and peptides (for convenience, both are referred to herein as "proteins"). The chip is also useful for determining crystallization conditions for small molecules, such as small drug molecules. The chips of the invention dramatically reduce the precious protein sample requirements for crystallization screening. Small sample volumes enable rapid synthesis due to shortened crystallization times and also exploration of a larger crystallization parameter space. Miniaturization, automation, and integration provide for simpler and more reproducible experiments, while eliminating tedious tasks and errors. Time spent by researchers in setting up screening conditions is dramatically reduced, enabling much higher throughput as compared to conventional methods.

Figure 1:
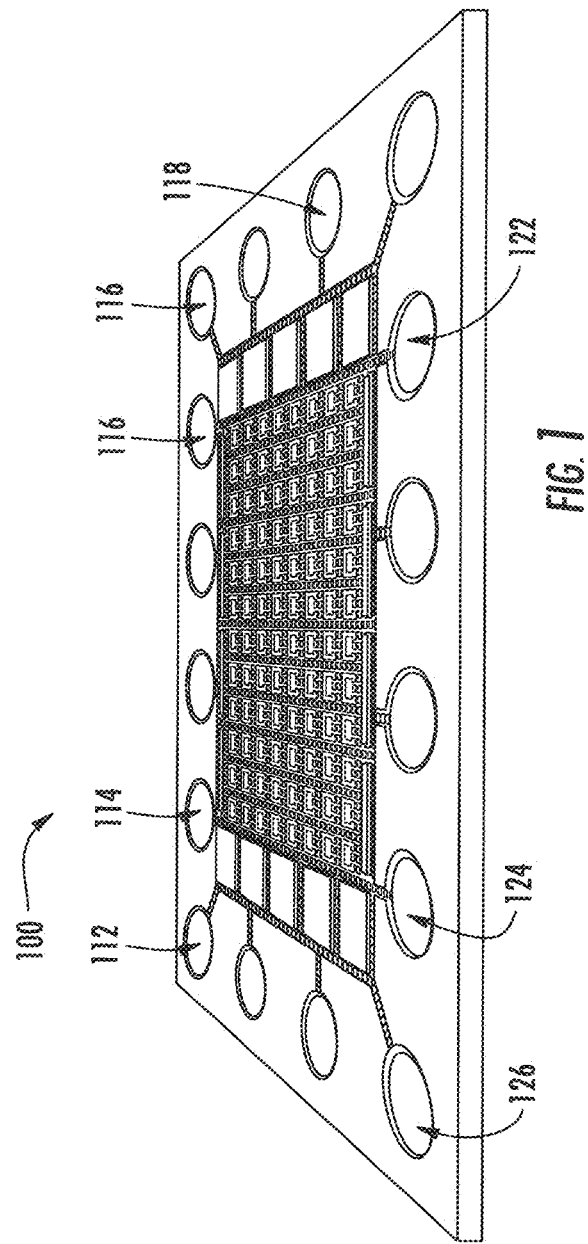
FIG. 1 is a perspective view of a 96-well optimization chip in accordance with an embodiment of the present invention.

In some embodiments, the system provides separate screening and optimization chips or separate screening and optimization regions on a single chip. The screening chip or region may, for example, be used to provide a loading and packaging scheme to pre-fill coarse grid reagents in all the on-chip wells or reservoirs. The optimization chip or region may, for example, be used to provide a loading and packaging scheme which automatically constitutes a fine grid of conditions around a user-defined screening "lead." The chips can provide on-chip dilutions from stock solutions of the reagent constituents (e.g., salt, pH buffer, precipitant, and water). FIG. 1 provides a schematic view of a 96-well optimization chip 100 that automatically sets up 96 fine grids from user-filled reservoirs. Multiple fluid ports and/or reservoirs may be provided, such as for salt 112, precipitant 114, pH buffer 116, water 118, protein 122, additive 124, and waste 126.

In one embodiment, the chip is provided as a component of a system generally including a microprocessor, one or more data output components and one or more data input components. In the operation of such a system, one or more dispensing reservoirs or wells of the chip may be loaded with one or more protein solutions. Dispensing wells may also be loaded with crystallization reagents, preferably 2, 3, 4, 5 or more crystallization reagents, which can be combined in the mixing wells to provide an array of crystallization conditions. The system is programmed to execute droplet operations, such as dispensing one or more sample droplets from the protein solution; transporting one or more of such sample droplets to a mixing well; dispensing one or more reagent droplets from the crystallization reagents; transporting one or more of such reagent droplets to at least a portion of the mixing wells to yield an array of wells comprising crystallization droplets, said array representing multiple crystallization conditions; and combining one or more sample droplets with each crystallization condition to potentially yield one or more crystallization droplets comprising one or more protein crystals. It is understood in alternative embodiments that the mixing may take place on a chip but not necessarily in a well.

Similarly, the chip may include one or more dispensing wells with protein solution loaded therein and one or more mixing wells comprising crystallization droplets loaded therein, said crystallization droplets representing multiple crystallization conditions. The system may be programmed to execute steps, such as dispensing one or more sample droplets from the protein solution and transporting at least a portion of the dispensed sample droplets to the mixing wells. Typically, at least a portion of the mixing wells each receives one or more of the sample droplets, thereby yielding an array of crystallization reagents comprising protein sample and having the capacity to one or more protein crystals.

A technique was surprisingly discovered which permits droplets with high concentrations of protein to be manipulated. In one embodiment, the protein solution has a concentration which exceeds about 1 mg/mL, about 10 mg/mL, about 50 mg/mL, or about 100 mg/mL. Further, the system of the invention can operate using exceptionally low volumes of protein solution. For example, in some embodiments, the amount of protein solution required for each crystallization condition tested does not exceed about 100, 90, 80, 70, 60, 50, 40, 30, 20, or 10 nL.

Importantly, small protein droplet volumes mean faster equilibration or crystal formation. Crystals formed in small drops may perform better than larger ones in diffraction studies because they have the advantage of uniform and rapid freezing when transferred into liquid nitrogen. Liquids can be dispensed, transported, and mixed on-chip without the need for robotics. The system can be self-contained, which results in higher quality of data due to consistency of the setup. Instrument manufacturing is much less costly than conventional robotic approaches, and disposable chips can be provided which are relatively inexpensive. Cost per screening condition is extremely low compared to conventional methods. Moreover, as the number of wells on the same chip goes up, cost per condition is decreased. For direct translation of crystallization hits to larger scale, droplet volumes should be accurate and precise and in the current invention, the dispensed droplet volume is much more precise as compared to conventional methods, e.g., <2%. Droplet operations and pathways are selected through a software control panel to empower users to readily create any combination of optimization conditions. The flat geometry provides better visualization of crystals and enables image analysis of droplets due to uniform illumination. The invention is compatible with Society for Biomolecular Screening (SBS) multiwell plate footprint and well-to-well pitch for any further automation steps.

The chips of the invention are fabricated using a scalable architecture, which permits a large number of on-chip crystallization conditions. For example, the number of conditions can be greater than 50, 100, 500, 1000, 5000, 10,000, 50,000, 100,000, 500,000, or 1,000,000. The invention also provides a programmable droplet-based microfluidic well platform, e.g., a platform having greater than 50, 100, 500, 1000, 5000, 10,000, 50,000, 100,000, 500,000, or 1,000,000. The system of the invention can also include droplet control software and instrumentation.

In some embodiments, the chips can accomplish all steps of synthesis (e.g., making use of a variety of droplet operations) and analysis, including for example, sampling, sample preparation, sample-processing, mixing, incubation, detection, and/or waste handling. These steps can be handled on-chip without requiring a significant off-chip support system.

In some embodiments, the invention can specifically exclude continuous-flow or droplet-based flow in fixed-channel-based microfluidics.

The invention is preferably provided as a bench-top instrument or as a handheld instrument. In one embodiment, discrete nanoliter-sized or sub-microliter-sized droplets are directly transported or manipulated using a microactuator structure described hereinbelow with reference to Section 7.8. In addition to transport, other microfluidic operations suitable for use in the invention include merging, splitting, mixing and dispensing of nanodroplets by varying the patterns of voltage activation. Large numbers of droplets can be simultaneously and independently manipulated allowing complex protocols to be flexibly implemented directly through software control. There is no joule heating or electrophoresis within the droplets and near 100% utilization of sample or reagent is possible because no priming is performed.

Further, the invention enables the splitting, dispensing, and/or transport of protein solutions having unprecedented high concentrations. For example, the invention includes chips, systems and methods of splitting, dispensing, and/or transporting protein solutions having concentrations that exceed than about 1, 10, 20, 30, 40, 50, 60, 70, 80, 90, or 100 mg/mL. Further, in a preferred embodiment, the splitting is facilitated by doping the silicone oil with a surfactant. For example, the surfactant may be a lipophilic surfactant, such as Triton X-15. Other suitable filler fluids and surfactants are described hereinbelow with reference to Section 7.8.4.

Nucleation and growth phases can be separated by performing on-chip dilutions after nucleation is observed to favor growth and stop further nucleation, as such a dilution method was reported to yield 6× the number of crystals suitable for X-ray diffraction compared to conventional methods. Crystal harvesting can be automated by transport of crystal-laden droplets for automatic loading into capillaries for X-ray diffraction studies. The crystals can, for example, be loaded by capillary action. Alternatively, crystals can be loaded by active vertical axis actuation through electrostatics.

In one embodiment, the screening chip includes a multi-well plate (also referred to as a microtiter plate). The multi-well plate may be pre-loaded with crystallization reagents. The plate can also include a port for introduction of protein solution, and microfluidics for moving droplets of protein solution into and between wells of the plate. The chip can be provided as a component of a system programmed to separate the protein solution sample into multiple droplets, each of which is moved to a preloaded well where it is combined with the preloaded crystallization reagents. The contents of the wells or other regions of the chip can then be analyzed automatically or manually for the presence of crystals. In some embodiments, the dimensions may be set up to conform to the SBS footprint dimensions for comparable microplates, e.g., for a 96, 384 or 1536-well plate.

In another embodiment, the optimization chip includes multiwell plate with one or more access ports for inputting reagents, as well as one or more access ports for inputting protein solution. The multiwell plate may be pre-loaded with reagents. Examples of useful reagents include pH buffers, salts, precipitants and other crystallization reagents. The plate can also include a port for introduction of protein solution. A system including the chip can be programmed to effect droplet operations to separate the protein solution sample into multiple droplets, each of which is moved to a well or processing region, and to separate the reagent solutions into multiple droplets, each of which is moved to a well or processing region. The system can be programmed to permit the user to control mixing and dilution of reagents and protein sample so as to systematically vary conditions in each well according to parameters set by the user. Ideally, these parameters are established based on prior analysis using a screening chip, as described above. Alternatively, results from a screening chip are used by the system to automatically select parameter variables for use in the optimization chip. The contents of the wells can then be analyzed automatically or manually for the presence of crystals. In some embodiments, the chip dimensions may conform to the SBS footprint dimensions for comparable microplates, e.g., for a 96, 384 or 1586-well plate. While there are no standards yet on higher number of wells in a microtiter plate, the technology of the invention enables scaling down to accommodate thousands of wells in the same SBS footprint.

7.2 Droplet-Based Protein Crystallization Examples

The following non-limiting examples are provided only for the purpose of illustrating various aspects of the invention and should not be construed as limiting the scope of the invention.

7.2.1 Microfluidic Platform Development & Material Compatibility

A prototype chip with sample injection elements, reservoirs, droplet formation structures, fluidic pathways and mixing areas, was fabricated to test the various components of the microfluidic platform. Droplets (25 nL) of several model proteins (lysozyme, glucose isomerase, proteinase K, grp94, hsp90, and $\alpha$-haemolysin) were reliably dispensed and manipulated on-chip using electrical fields. The protein concentrations were in range of tens of mg/mL which is typical for protein crystallization experiments. To manipulate this high concentration of proteins, the filler fluid (silicone oil) was modified with an oil-soluble surfactant. Crystallization reagents containing commonly used precipitants, salts, and buffers were also successfully dispensed and transported on-chip.

7.2.1.1 Microfluidic Platform Development

A programmable droplet-based chip was fabricated. The fully assembled chip also included a transparent top-plate containing access holes aligned to the loading ports.

The overall chip size was 25 mm×50 mm with 97 discrete electrodes at a 500 µm pitch. The nominal droplet volume was ~25 nL.

7.2.1.2 Dispensing and Transport of Proteins

Proteins tend to non-specifically adsorb to surfaces they come in contact with, especially hydrophobic ones. In addition to contamination, protein adsorption also renders surfaces permanently hydrophilic. This is detrimental to droplet manipulation since the chip surface cannot be switched back to being a hydrophobic surface by electric fields. Therefore any contact between a liquid droplet containing proteins and the chip surfaces should be avoided to prevent contamination and facilitate transport. The use of a low surface tension oil such as silicone oil helps in the transport of protein solutions on our chips. The oil forms a thin film between the droplet and the surfaces, thereby minimizing adsorption and contamination. However, the stability of the oil film decreases with increasing protein concentration (which lowers the interfacial tension with oil) and consequently droplets having higher protein content are expected to be more difficult to manipulate on-chip.

Crystallization experiments sometimes require high concentrations (tens of mg/mL) of protein to create super-saturation conditions. Means for performing operations, such as transporting, dispensing, and splitting, on high concentration of proteins with electric field-based manipulation on the chip were surprisingly discovered. The droplet formation process (using only electric fields) is more severely affected than transport due to protein adsorption, since the liquid in the reservoir has a much larger surface area to adsorb to than a unit droplet. For example, though 10 mg/mL BSA droplets (manually dispensed) were transportable, droplet formation worked only for solutions with less than 0.01 mg/mL BSA. Though it is possible to use external pressure sources to assist the droplet formation for high protein concentration solutions, it adds to the mechanical complexity of the system. It is therefore preferable to find a solution that would enable dispensing of high concentrations of proteins using only electric fields.

The on-chip compatibility of several model proteins including lysozyme, proteinase K, glucose isomerase, grp94, hsp90, and α-haemolysin were tested. A low viscosity silicone oil (<2 cSt) was used as the filler fluid in all experiments. 0.1% (w/w) Triton X-15, a lipophilic surfactant, was added to the oil so that high concentrations protein droplets could be formed or dispensed from on-chip reservoirs. The surfactant lowered the surface tension of the oil and increased the stability of the oil film between the droplet and the chip surfaces which significantly reduced adsorption.

Using the surfactant modified silicone oil, fully automated droplet formation was possible up to protein concentrations of 10's mg/mL using voltages less than 50V (which is typically used for simpler liquids such as water). This is 3 orders of concentration improvement over the results obtained using unmodified silicone oil. The volume of each unit droplet was ~25 nL. Table 1 lists the proteins with the highest concentration tested and found to be most compatible with the system of the present invention.

TABLE 1

Protein Compatibility Chart

| Protein | Concentration |
| --- | --- |
| Lysozyme | 75 mg/mL |
| Glucose Isomerase | 30 mg/mL |
| Proteinase K | 20 mg/mL |
| Grp94 | 27 mg/mL |
| Hsp90 | 30 mg/mL |
| α-haemolysin | 10 mg/mL |

7.2.1.3 Dispensing and Transport of Crystallization Reagents

Crystallization reagents usually consist of three components—a salt, precipitant and a buffer. Commonly used precipitants include inorganic salts, organic polymers such as polyethylene glycols (PEG), non-volatile organics such as 2-methyl-2,4-pentanediol (MPD) and volatile organics such as isopropanol. The individual components used in crystallization reagents span a wide range of physical and chemical properties, and it is important to evaluate their compatibility with the system. Salt concentrations can be as high as several moles per liter. The pH of buffers spans a large range from acidic (pH 3.0) to basic (pH 8.0). High molecular weight PEGs have viscosities as high as 100 cP for a 50% (w/w) solution in water. Organics such as isopropanol have a low interfacial tension and may also partition into the oil. Surfactants (which lower interfacial tension) are also used in the crystallization of membrane proteins.

To demonstrate dispensing and transport of crystallization reagents on-chip, a representative subset of Hampton Research's sparse-matrix, Crystal Screen™, was chosen and which covered a range of the salts, buffers and precipitants. Table 2 lists the Crystal Screen™ reagents used in the compatibility experiments. Solutions containing 0.001%, 0.01% and 0.1% of Triton X-100 surfactant (v/v) were prepared in phosphate buffer for studying the effect of interfacial tension on transport. The interfacial tension of the surfactant solution with oil varied between 7 mJ/m$^2$ (0.1% Triton X-100) to 33 mJ/m$^2$ (0% Triton X-100).

TABLE 2

Crystal Screen ™ reagents tested on-chip and their components

| Reagent | Salt | Buffer | Precipitant |
| --- | --- | --- | --- |
| 1 | 0.02M Calcium chloride | 0.1M Sodium acetate, pH 4.6 | 30% v/v 2-methyl-2,4-pentanediol |
| 2 | | | 0.4M Potassium sodium tartrate |
| 3 | | | 0.4M Ammonium dihydrogen phosphate |
| 4 | | 0.1M Tris hydrochloride, pH 8.5 | 2M Ammonium sulfate |
| 5 | 0.2M tri-Sodium citrate | 0.1M Sodium HEPES, pH 7.5 | 30% v/v 2-methyl-2,4-pentanediol |
| 6 | 0.2M magnesium chloride | 0.1M Tris hydrochloride, pH 8.5 | 30% w/v polyethylene glycol 4000 |
| 7 | | 0.1M sodium cacodylate, pH 6.5 | 1.4M sodium acetate trihydrate |
| 8 | 0.2M tri-sodium citrate | 0.1M sodium cacodylate, pH 6.5 | 30% v/v isopropanol |
| 9 | 0.2M ammonium acetate | 0.1M tri-sodium citrate, pH 5.6 | 30% w/v polyethylene glycol 4000 |
| 13 | 0.2M tri-Sodium citrate | 0.1M Tris hydrochloride, pH 8.5 | 30% v/v polyethylene glycol 400 |
| 15 | 0.2M ammonium sulfate | 0.1M sodium cacodylate, pH 6.5 | 30% w/v polyethylene glycol 8000 |

Figure 2:
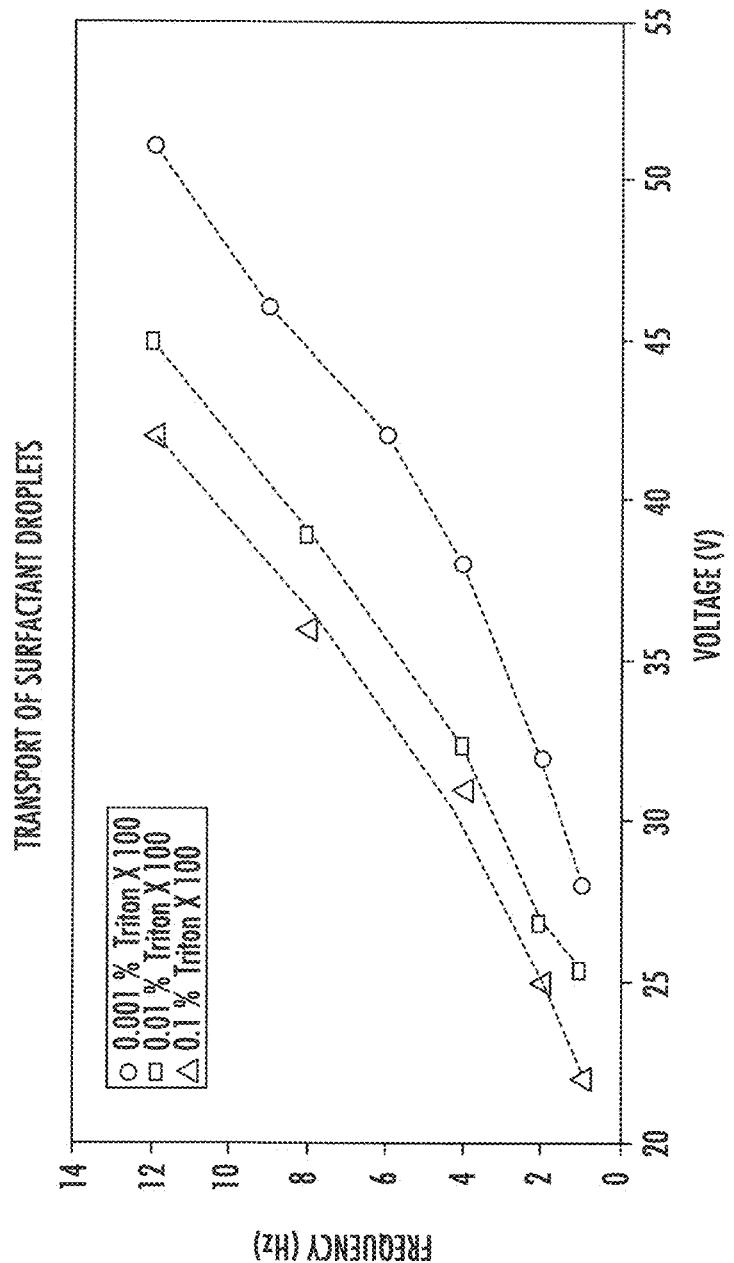
FIG. 2 is graph of transport characteristics of different surfactant solutions depicting the maximum droplet transfer frequency as a function of voltage.

FIG. 2 plots the maximum droplet transfer frequency as a function of voltage for different surfactant solutions. The plot indicates that droplets with lower interfacial tension require less voltage to be transferred at a particular rate. However, the drop in voltage requirement is not significant and is only 10V for transfer at 12 Hz. Droplet dispensing and transport worked for all the crystallization reagents tested. Table 2 above lists the individual salts, buffers and precipitants which constituted the tested reagents. Though 100% isopropanol is completely miscible with silicone oil, mixtures of isopropanol and water up to 80% isopropanol (v/v) were immiscible in silicone oil. Droplet manipulation using electric fields is independent of salt concentration from 1 μM to 2M. The above results indicate that liquids with a wide range of properties are compatible with the system of the present invention.

7.2.2 Microbatch Protein Crystallization on the Bench

The effect of oils with varying viscosities and volatility on crystallization was tested on the bench using a crystal screen for hen egg white lysozyme. The oils tested were 1 cSt, 1.5 cSt and 2 cSt silicone oil, paraffin oil, and fluorosilicone oil. Of all the oils tested, the 2 cSt silicone oil had the right combination of low viscosity preferable for electric field mediated manipulations and low volatility required for long crystallization experiments, and therefore was used for the on-chip crystallization experiments. The addition of surfactants to the oil also did not affect the crystal formation process. Screening experiments were also performed on the bench for glucose isomerase and proteinase K to identify crystallization conditions that were subsequently tested on-chip.

7.2.2.1 Effect of Oils on Crystallization

Silicone oils, paraffin oils, or a mixture of the two are the most commonly used oils in microbatch-in-oil crystallization. A combination of fluorosilicone oil (dense) and paraffin oil (light) has also been used in a specific case of microbatch referred to as the floating-drop method.

1 cSt silicone oil, 1.5 cSt silicone oil, 2 cSt silicone oil, paraffin oil and a fluorosilicone oil were tested as potential candidates for on-chip microbatch-in-oil crystallization. A crystal screen for lysozyme was used to evaluate the oils on the bench. 75 mg/mL lysozyme was prepared in 0.1M sodium acetate buffer, pH 4.6. Twelve different concentrations of NaCl in water (1.2M to 3.0M in steps of 0.2M) were used as the precipitant. The screens were set up in 96-well plates. At first, 100 μL of the oil was dispensed into the wells, followed by 5 μL of the 75 mg/mL lysozyme sample. 5 μL of the different precipitant solutions were then added gently to the sample and allowed to mix without any stifling. A floating-drop microbatch experiment was set up in a similar fashion using fluorosilicone oil as the heavier oil and paraffin oil as the lighter oil. The wells were closed with a lid but not completely sealed. The wells were inspected after 1 day, 2 days, 3 days and 1 week.

Basic droplet manipulation experiments were also performed on-chip using paraffin oil and fluorosilicone oil to evaluate the compatibility of the oil with the platform. Low viscosity silicone oils (<2 cSt) have also already been shown to be compatible with the microfluidic platform of the present invention.

With the exception of 1 cSt silicone oil, all the other experiments gave similar crystals (size, shape and number) in wells with 1.2-2.2M NaCl. A mixture of crystals and precipitate was seen in wells with 2.4-2.6M NaCl. The proteins completely precipitated out in wells with higher NaCl concentration. 1 cSt silicone oil was 100% volatile and evaporated within 1 day of setting up the experiment, causing the protein solution to dry out. 1.5 cSt silicone oil also evaporated over the course of several days. 1 cSt and 1.5 cSt silicone oil can still be used for on-chip crystallization if the system is completely sealed. 2 cSt silicone oil was non-volatile, but the crystals still dried out after 2-3 weeks due to the high water vapor permeability of silicone oils.

The high viscosity of paraffin oil required substantially higher voltages for droplet manipulation on-chip. The fluorosilicone oil dissolved the hydrophobic coating and was therefore not suitable for use on these chips. Of all the oils tested, 2 cSt silicone had the best combination of low viscosity and low volatility for use on-chip. Even though the paraffin oil/silicone oil mixture is compatible with the chips, pure silicone oils are preferred. Table 3 summarizes the various results obtained from the experiments described above.

TABLE 3

Filler fluid suitability for on-chip crystallization

| Oil | Bench experiments | On-chip compatibility | Overall compatibility |
|---|---|---|---|
| 1 cSt silicone oil | 100% volatile. All the oil evaporates in less than a day | Compatible | Compatible (in a sealed system) |
| 1.5 cSt silicone oil | Oil evaporates within a few days. | Compatible | Compatible (in a sealed system) |
| 2 cSt silicone oil | Non-volatile. Fully compatible | Compatible | Fully Compatible |
| Paraffin oil | Non-volatile. Fully compatible | High viscosity required substantially higher voltages for droplet manipulation on-chip | Partially compatible |

7.2.2.2 Protein Crystallization on the Bench

Protein crystallization screens were set up for three model proteins—lysozyme, proteinase K and glucose isomerase. 2 cSt silicone oil with 0.1% Triton X-15 was used as the oil medium to simulate conditions similar to those on chip. The screens were set up in 96-well plates. 100 μL of the oil was first dispensed into the wells followed by 5 μL of the protein sample. 5 μL of the precipitant solutions was then added gently to the sample and allowed to mix without any stirring.

Lysozyme—75 mg/mL lysozyme was prepared in 0.1M sodium acetate buffer, pH 4.5. A concentration gradient of sodium chloride in water (1.2M to 3.0M) was used as the precipitant. Table 4 summarizes the results of the lysozyme screen.

TABLE 4

Lysozyme screen results

| Precipitant (NaCl) | After 2 days |
|---|---|
| 1.2M | Crystals |
| 1.4M | Crystals |
| 1.6M | Crystals |
| 1.8M | Crystals |
| 2.0M | Crystals |
| 2.2M | Crystals |
| 2.4M | Precipitate and crystals |
| 2.6M | Precipitate and crystals |
| 2.8M | Precipitate |
| 3.0M | Precipitate |
| 3.2M | Precipitate |

Proteinase K—20 mg/mL proteinase K was prepared in 25 mM HEPES buffer, pH 7.0. Reagents from Hampton's Crystal Screen™ (indicated in Table 5) were used as the precipitant. Table 5 summarizes the results of the proteinase K screen.

TABLE 5

Proteinase K screen results

| Precipitant (Crystal Screen ™) | After 2 days |
|---|---|
| Reagent 6 | Crystals |
| Reagent 12 | Clear |
| Reagent 17 | Crystals |
| Reagent 19 | Clear |
| Reagent 22 | Crystals |
| Reagent 28 | Crystals |
| Reagent 30 | Crystals |
| Reagent 31 | Crystals |
| Reagent 36 | Crystals |
| Reagent 39 | Crystals |
| Reagent 40 | Crystals |
| Reagent 41 | Crystals |
| Reagent 42 | Crystals |
| Reagent 43 | Clear |
| Reagent 48 | Crystals |

Glucose isomerase—30 mg/mL glucose isomerase was prepared in deionized water. Reagents from Hampton's Crystal Screen™ (indicated in Table 6) were used as the precipitant. Table 6 summarizes the results of the glucose isomerase screen.

TABLE 6

Glucose isomerase screen

| Precipitant (Crystal Screen ™) | After 2 days |
|---|---|
| Reagent 9 | Crystals |
| Reagent 10 | Crystals |
| Reagent 14 | Crystals |
| Reagent 15 | Crystals |
| Reagent 18 | Precipitate |
| Reagent 21 | Clear |
| Reagent 23 | Crystals |
| Reagent 24 | Precipitate |
| Reagent 32 | Precipitate |
| Reagent 35 | Precipitate |
| Reagent 44 | Clear |

The presence of 0.1% Triton X-15 surfactant in the oil did not affect crystallization on the bench.

7.2.3 Protein Crystallization On-Chip & System Integration

Lysozyme, proteinase K and glucose isomerase were crystallized on-chip using the surfactant-modified 2 cSt silicone oil as the filler fluid. Droplets of the protein and precipitant were automatically dispensed, mixed, and incubated on-chip. The precipitant was chosen from the results of the screening experiments on the bench. Crystals typically appeared after 1 day and the shape and size of the crystals were similar to those obtained on the bench. A coarse crystallization screen was also set up on-chip for lysozyme varying the precipitant (NaCl) concentration. Four different precipitant concentrations were automatically generated on-chip by dilution (3:0, 2:1, 1:2, 0:3) and mixed with a 25 nL lysozyme droplet. The results compared favorably with experiments on the bench.

7.2.3.1 Protein Crystallization On-Chip

Three model proteins, lysozyme, proteinase K and glucose isomerase were crystallized on-chip using 2 cSt silicone oil with 0.1% Triton X-15 as the filler fluid. Protein concentrations were identical to those used on the bench. 1.8M sodium chloride in water was used as the precipitant for lysozyme. Crystal Screen™ Reagent 6 (0.2M $MgCl_2$, 0.1M Tris HCl, pH 8.5, 30% w/v PEG 4000) was used as the precipitant for proteinase K, and Crystal Screen™ Reagent 14 (0.2M $CaCl_2$, 0.1M HEPES-Na, pH 7.5, 28% v/v PEG 400) was used as the precipitant for glucose isomerase. 25 nL droplets of the protein and the crystallization reagent were automatically dispensed, mixed, and incubated on-chip.

Figure 3:
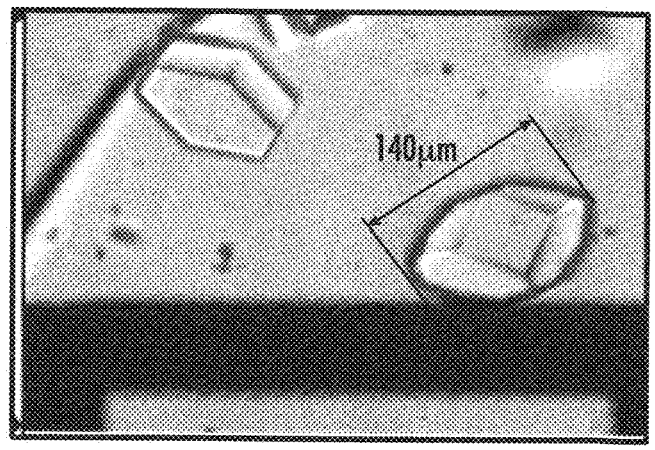
FIG. 3 is an illustration of lysozyme crystals formed on-chip at 20× magnification in accordance with an embodiment of the present invention.
Figure 4:
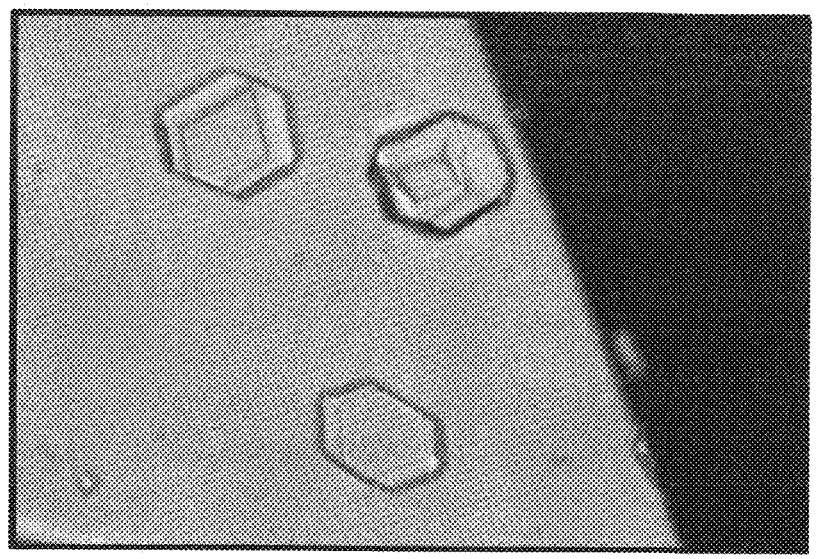
FIG. 4 is an illustration of glucose isomerase crystals formed on-chip at 20× magnification in accordance with an embodiment of the present invention.
Figure 5:
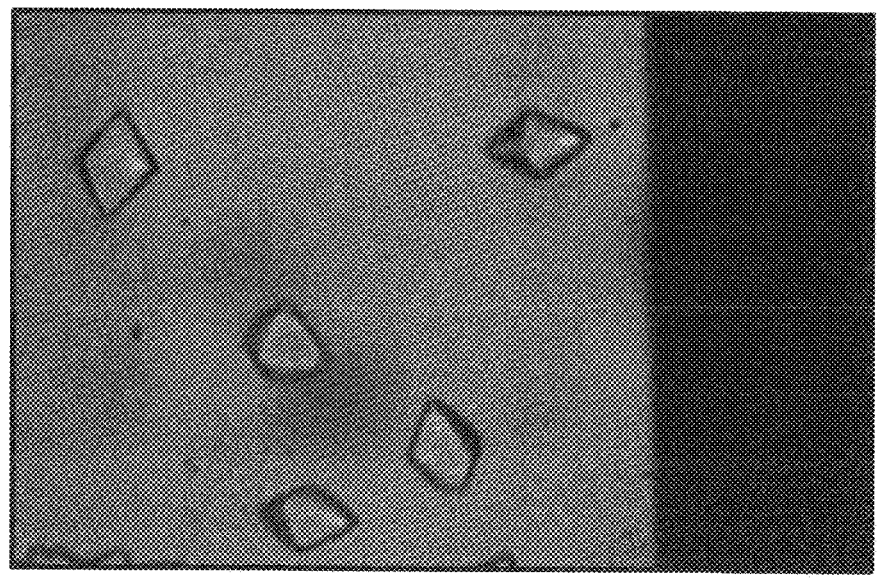
FIG. 5 is an illustration of proteinase K crystals formed on-chip at 40× magnification in accordance with an embodiment of the present invention.
Figure 6:
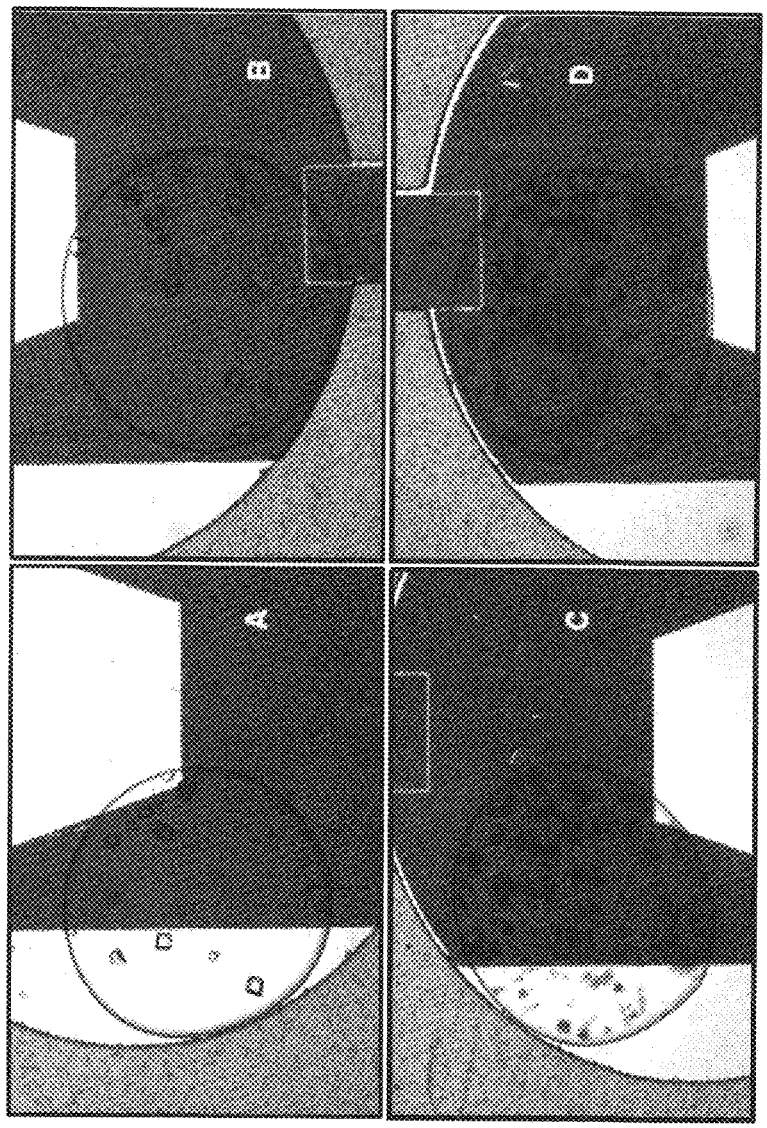
FIGS. 6A-6D are illustrations of lysozyme crystals formed on-chip at various NaCl solutions in accordance with an embodiment of the present invention.

Crystals appeared after 1 day for all the three proteins tested. The crystal size and shapes were similar to those obtained on the bench. FIG. 3 shows lysozyme crystals formed on-chip at 20× magnification. The size of the crystals was ~140 μm. FIG. 4 shows crystals of glucose isomerase on-chip at 20× magnification and FIG. 5 shows crystals of proteinase K at a 40× magnification. The glucose isomerase crystals were ~70 μm and the proteinase K crystals were ~50 μm.

7.2.3.2 Coarse Matrix Screen for Lysozyme

As a demonstration and integration of all the functions, the experiment integrated dispensing, transport, and mixing of a lysozyme droplet with 4 different concentrations of a precipitant (NaCl) to create a screen on the chip. The lysozyme sample (75 mg/mL) and two different concentrations of NaCl (1.2M and 3.0M) were injected into on-chip reservoirs. Intermediate concentrations of 1.8M and 2.4M NaCl were automatically generated on-chip by dispensing and mixing 2 droplets of 1.2M NaCl with 1 droplet of 3.0M NaCl and 1 droplet of 1.2M NaCl and 2 droplets of 3.0M NaCl respectively. One ~25 nL droplet of 75 mg/mL lysozyme was then dispensed and mixed with 3 droplets each of the 1.2M, 1.8M, 2.4M and 3.0M NaCl solutions. A similar experiment was set up on the bench as a control.

Crystals were observed using 1.2M and 1.8M NaCl both on-chip and on the bench after a day. Images of the results obtained for the different precipitant conditions on-chip are shown in FIGS. 6A-6D. This experiment demonstrated two important aspects of the protein crystallization process. The first aspect relates to fluidic operations involved in the setup of coarse screen. Once the samples and reagents are loaded, a comprehensive screening experiment can be set up using a very small quantity of protein without any manual intervention. For example, 4 different conditions were set up using only 100 nL of protein. The second aspect relates to automatic dilutions of precipitants for optimization. It was shown that using two different concentrations of the precipitant, intermediate concentrations can be generated automatically on-chip. This forms the basis of an optimization experiment in which a matrix of conditions is usually set up around a "lead" seen in the coarse screen.

Among other things, the work described herein demonstrates a nanodroplet-handling platform for manipulating a wide variety of proteins and reagents, the compatibility of crystal nucleation and formation with electric field mediated droplet operations, favorable translation between on-chip nano-batch and off-chip micro-batch, and screening of multiple conditions and on-chip setup of dilutions for optimization.

7.3 Droplet-Based Protein Crystallization Further Examples

Further examples relevant to the design, development, fabrication, and validation of a digital microfluidic protein crystallization chip are included hereinbelow and include a screening chip which requires only one drop of protein (4 μL) for screening with 384 pre-filled reagents and an optimization chip which requires 1 μL of protein for fine grid optimization with 96 reagents constituted fully on-chip from the individual components of a screening reagent that yielded a lead.

Separation of Screening and Optimization Chips.

The requirements for screening and optimization are different, so two different chips can be used, even though the digital microfluidic multiwell chip can serve as the basic platform for each. Alternatively, a single chip with two different regions (screening and optimization) can be used. In the screening phase, researchers typically screen a protein with a known set of reagents where the concentrations of the constituents are pre-set in a coarse grid covering a broad range of crystallization space. Therefore, the screening chips and/or cartridges including the screening chips can be pre-loaded with known reagents saving the user from having to load 384 wells. In the optimization phase, however, researchers pick a coarse grid condition that yielded a lead during screening and then prepare a fine grid of reagent concentrations by performing a number of dilutions. Therefore, the optimization chip can set up 96 conditions through on-chip dilutions from a few reservoirs filled with the stock solutions of the constituents. The dimensions of both the chips can conform to the SBS standard multiwell plate footprints (85.48×127.76 $mm^2$) and well-to-well pitch (9/4.5/2.25 mm for 96/384/1536 respectively) so that the chips are readily compatible with robotic plate-handling equipment.

Only about half of all proteins crystallized, using any method, have turned out to be useful in determining the 3D structure. The reason is that the "leads" obtained during screening may not form large crystals in the optimization phase. Vapor diffusion (VD) and free interface diffusion (FID) are particularly challenging to optimize because a large crystallization space is sampled in the process, which is advantageous, but the exact conditions for crystallization are not known.

A microbatch method lends itself readily for translation from low volumes on-chip to larger volumes on the bench if the volume of the reagent and the protein are known accurately. The precision of droplet dispensing on our platform allows for accurate translation of optimized crystallization conditions from nanoliter-level on-chip to microliter-level on the bench.

7.3.1 Digital Microfluidic Multiwell Plate

A scalable architecture can be used to make a chip with 384 on-chip crystallization conditions. A programmable droplet-based microfluidic 384-well platform can also be made, along with relevant droplet control software and instrumentation. The key fluid handling capabilities for protein crystallization was demonstrated and the protein required for each screening condition can further be scaled down from 25 nL to sub-nanoliters.

7.3.1.1 Screening and Optimization on Digital Microfluidic Chips

Screening-Chip Architecture

An important issue in the design of the screening chip is the routing complexity of the electrical signals that control the well-plate electrodes. To reduce the product cost and simplify design, it is useful to minimize the number of electrodes needed to provide droplet pathways from the protein reservoir to the screening wells.

Algorithms for fault tolerance can also be developed to get around the unlikely event of a protein droplet getting stuck on a pathway. Each protein sample loaded into a reservoir is very precious so instead of throwing away the chip because of one fault, the algorithm can adaptively find a path for other droplets that avoids the fault by configuring multiple mutually-disjoint paths from a designated reservoir to the well.

Optimization Chip Architecture

Figure 7:
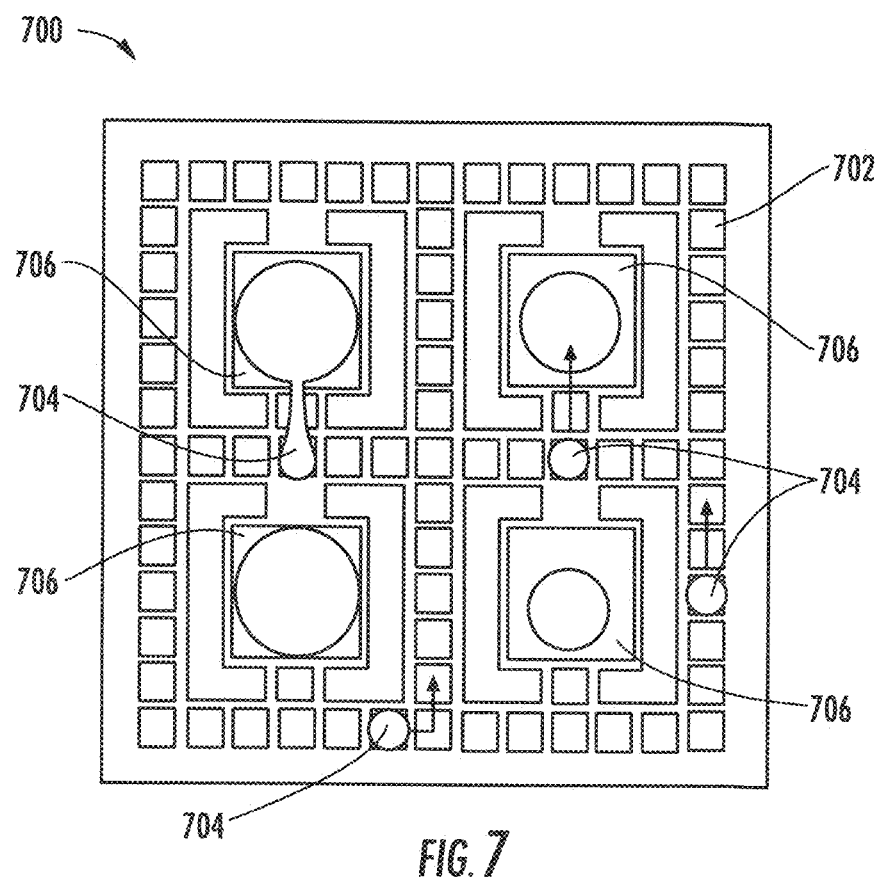
FIG. 7 is a plan view of wells and surrounding electrodes of a microfluidic chip in accordance with an embodiment of the present invention.
Figure 8:
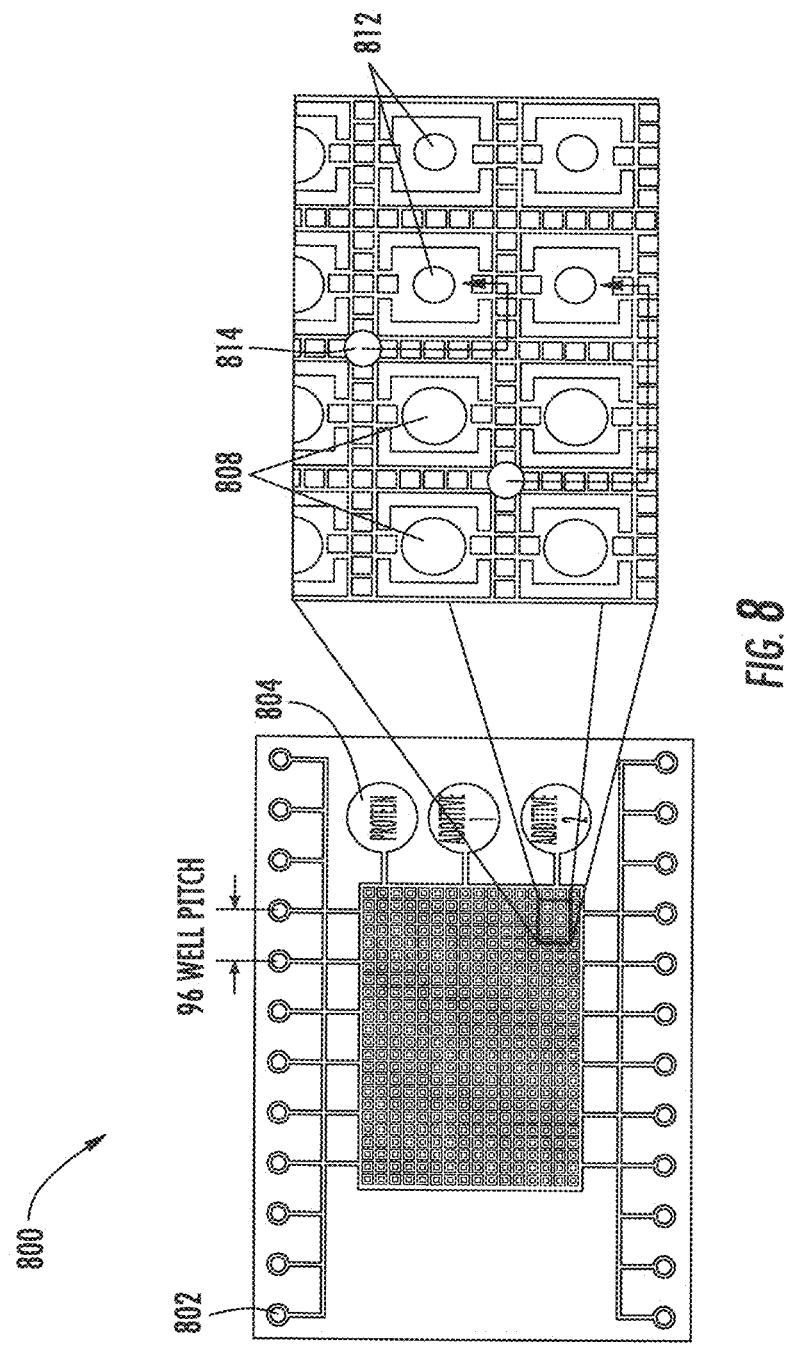
FIG. 8 is a schematic plan view of a screening chip in accordance with an embodiment of the present invention.
Figure 10:
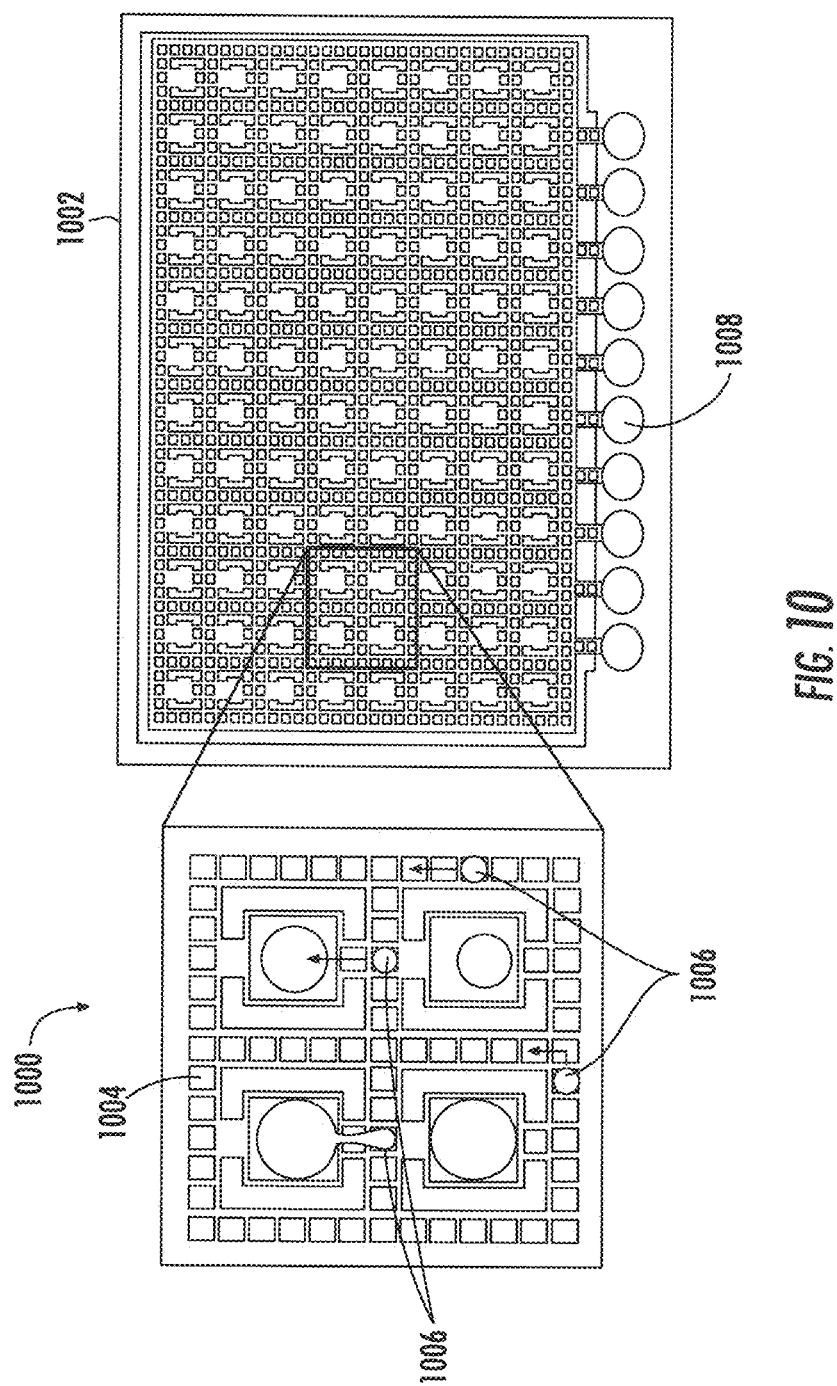
FIG. 10 is a plan view of a microfluidic chip in accordance with an embodiment of the present invention.

From FIG. 7, it can be seen that the microfluidic chip 700 design of this specific embodiment of the invention preferably has 77 electrodes 702 to transfer droplets 704 between four wells 706 (see also FIGS. 8 and 10). To independently control all 384 wells, it would require 1000's of input/output electrical pads which becomes very expensive. As such, a 4-"pin-limited" design was implemented where every fourth electrode is connected together to perform droplet operations between wells.

In pin-limited designs, the simultaneous movement of multiple droplets is restricted where two or more moving droplets might get inadvertently coupled. A method can be developed to analyze interferences between droplets in every clock cycle. In some steps of the fine grid setup process, interference may be inevitable, then one droplet may have to undergo a stall cycle (i.e., stay in its current location). For both 96 and 384 well-plate arrays, the minimum number of independent control pins sufficient to provide full control can be identified (especially desirable for concurrently executing multiple steps during fine grid setup) of a single droplet. For any electrode in the array, the control pins for all its adjacent electrodes are preferably distinct. Pin layouts can be identified, i.e., assignments of control signals to electrodes, such that maximum freedom of movement of groups of droplets in the array can be ensured.

For the optimization chip, droplet routing can be managed between loading reservoirs and wells as well as between intermediate reservoirs and wells. Droplet routes can be identified with minimum lengths, where route length is measured by the number of electrodes in the path from the starting point to the destination. During droplet routing, it is preferable for a minimum spacing between droplets to be maintained to prevent accidental mixing, except when droplet merging is desired. For multiple droplet routes that may intersect or overlap with each other, fluidic constraint rules must be introduced to avoid undesirable behavior.

Algorithms can be used to schedule droplet operations based on optimal utilization of the stock solutions without requiring users to refill the stock solutions. State-of-the-art in computer architecture can be leveraged to build a microfluidic "compiler" for the optimization chip as there are a number of similarities between the fine grid setup problem and the problem of compiling a program written in a high-level programming language (such as C/C++). The compiler typically decomposes user-level code to a series of hardware instructions based on the instruction-set architecture of the underlying microprocessor. Next, the compiler determines parallelism between instructions, maps these instructions to functional units, allocates the hardware registers for instruction execution, and performs instruction scheduling. The microfluidic compiler can view the given stock solutions as the initial values of variables in the user program and fine grid conditions can serve as the final values of another set of variables. The latter set of variables can be controlled by manipulating the initial set of variables as well as additional intermediate variables. Once the compiler determines the set of microfluidic operations required for fine grid setup, a graph model can again be used to describe the fine grid setup protocol, where the vertex set is in one-to-one correspondence with the set of operations and the edge set represents dependencies between the operations. Next, a synthesis tool can be developed to generate detailed implementations from the sequencing graph model.

The proposed synthesis tool can perform both architectural-level synthesis (e.g., scheduling and resource binding) and geometry-level synthesis (e.g., layout of module placement and routing) for a fine grid setup based on user-defined concentrations. The output of the synthesis process can include a mapping of operation to wells, a schedule for the various operations, and the placement of the modules. The synthesis procedure can identify a desirable design point that satisfies the input specifications and also optimizes some figures of merit, such as the volumes of the stock solutions and number of wells for fine grid setup. All these steps can be transparent to the user.

7.3.1.2 Design and Fabrication of Digital Microfluidic Chips

Figure 9:
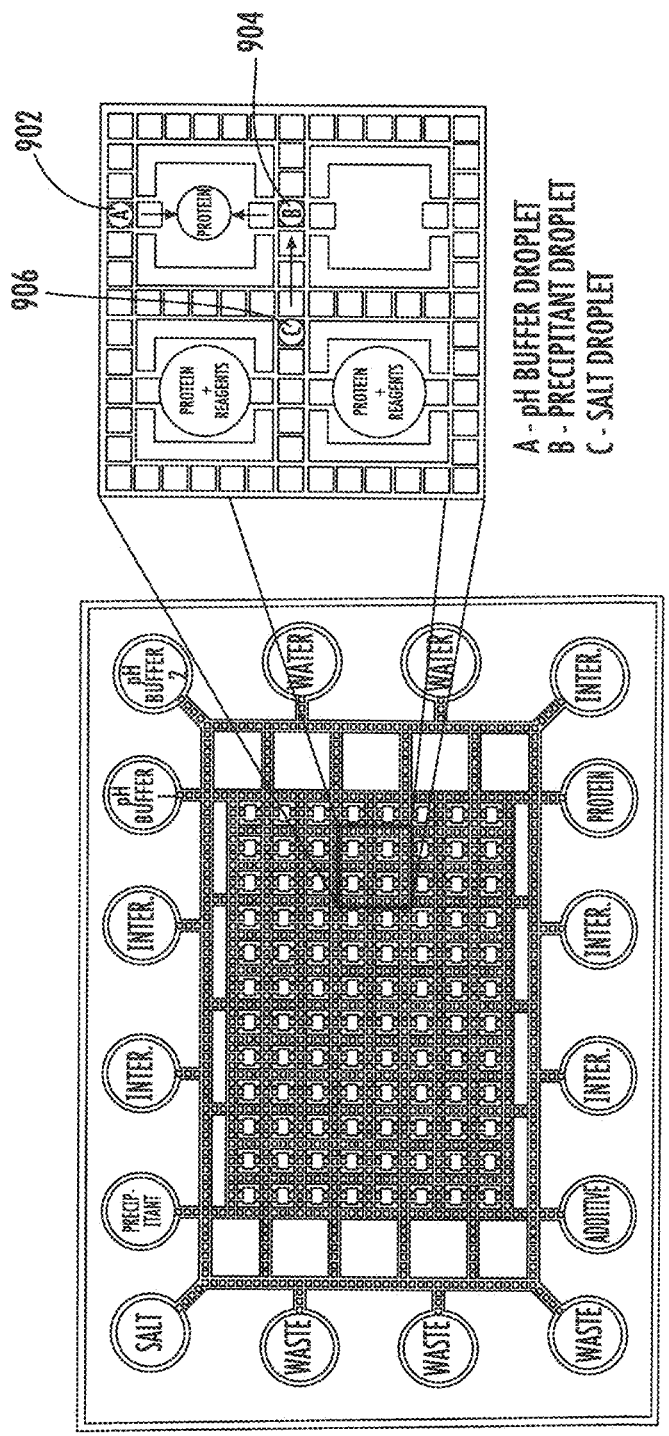
FIG. 9 is a schematic plan view of an optimization chip in accordance with an embodiment of the present invention.

Dispensing reservoirs and transport electrodes can be made so that droplet volume (determined by the electrode area and gap height) can be scaled down from 25 nL (500×500×100 $\mu m^3$) to 10.5 nL (375×375×75 $\mu m^3$), e.g., as shown in FIGS. 8 and 9. The number of wells can, for example, be 24, 96, 384, or even 1536. Referring to FIG. 8, a screening chip pre-filled with 384 reagents for crystallization is shown. Overall dimensions conform to SBS multiwell plate. The 96-well modules 800 can, for example, have input ports 802 and a dispensing reservoir 804 with a sample loading port designed to accept about 1 µL of protein. Other dispensing reservoirs can be provided. The zoom-in view depicts, as an example, protein and reagent sample mixes 808, pre-loaded reagents 812, and a protein droplet 814 en route. A combination of 4 such 96-well modules yields a 384-well plate and a further combination of 16 yields a 1536-well plate. The pitch in each of the 96-well modules is that of a 1536-well plate i.e., 2.25 mm which can accommodate a 6×6 pattern of 375×375 $\mu m^2$ electrodes. The line spacing between the electrodes can be ~1 mil (25.4 µm), the gap height formed by a photopatternable gasket can, for example, can be about 3 mils (76.2 µm), and multiple layers can be used to perform electrical routing. The digital microfluidic chips can be fabricated in printed circuit board (PCB) processes that have been adapted to various fabrication needs. PCB processes allow the manufacture of the chips inexpensively and therefore enable widespread adoption.

FIG. 9 schematically depicts an optimization chip that automatically sets up 96 fine grid conditions. 96 optimization wells in 1536-pitch occupy only ¹⁄₁₆th area. The zoom-in depicts reagents, appropriately diluted on-chip, transported to a well. For example, pH buffer droplet A 902, precipitant droplet B 904, and salt droplet C 906 are shown being transported.

Further description of the architecture and operation of a typical droplet microactuator capable of being used with this aspect can be found hereinbelow with reference to Section 7.8.

7.3.2 Reagent Loading & Pre-Processing On-Chip

Separate screening and optimization chips were developed. For the screening chip, for example, a loading and packaging scheme can be developed to pre-fill coarse grid reagents in all the 384 wells. For the optimization chip, for example, a system of the invention can be programmed to automatically constitute a fine grid of 96 conditions. On-chip dilutions can also be performed from stock solutions of the reagent constituents (e.g., salt, pH buffer, precipitant, and water) for the optimization chip.

7.3.2.1 Screening Chip with 384-Wells Pre-Filled with Reagents

Protein crystallization is an empirical science that has benefited from the development of sparse matrix screens that coarsely sample large regions of crystallization space. Sparse matrix of reagents, described by Jancarik and Kim, has been successfully used as an initial screen for crystallizing more than 1000 proteins. Typical initial screens performed in structural biology labs (for example, the Hampton Research Crystal Screens I and II) consist of 50-100 different reagents and typically consume 200-400 µL of concentrated protein sample. Hampton Research also sells about 900 additional crystal screening reagents many of which are variants of Crystal Screens I and II. 1536 reagents can be used for microbatch screening and the screening chips can be filled with 384 reagents to save the user from having to load all the wells.

7.3.2.2 Choice of Reagents

In one embodiment, the screening chips can have 384 reagent wells on-chip. For example, five (5) different chips can be made with different combinations of pre-filled reagents. One of these chips can contain sparse matrix conditions and a few combinations of salts, PEG/salts, PEG/buffer, and other precipitants totaling 384 conditions. The remaining four (4) chips can be based on HWI's 1536 reagents, which include 46 salts at 10 different concentrations (460), 3 distinct PEGs at 5 different concentrations combined with each of the 46 salts (690), eight different PEGs ranging in molecular weight from 200 to 35,000 Da at 5 concentrations combined with buffers ranging in pH from 4.8 to 10.4 (226), 20-step fine screens of ammonium sulfate, lithium chloride, and potassium thiocyanate (60), and sparse matrix based on Crystal Screens I and II (100) adding up to a total of 1536 conditions. An example of the screening chip is found in Table 7.

TABLE 7

| Digital microfluidic screening chip specifications | |
|---|---|
| Protein Sample Reservoir | 1 |
| Reagents Pre-filled | 384 |
| Screening Wells | 384 |
| Protein Reservoir Capacity | 400 droplets |
| Unit droplet volume | ~10 nL |
| Total Protein Volume Required | 4 µL |
| SBS multi-well plate Footprint | 88.48 × 127.76 mm² |
| Well-to-well pitch | 2.25 mm |

7.3.2.3 Chip Layout

The overall chip size can be that of a standard SBS multiwell plate. Thus, 384 wells can be arranged in 1536-well pitch (2.25 mm) with electrode pathways to connect these wells to reagent and protein input loading ports. Reagent and protein droplets can be transported along these pathways from their input loading ports to the wells and other droplet operations can be conducted. 384 wells in a 1536-well pitch occupy only ¼$^{th}$ area of the digital microfluidic multiwell plate. The rest of the chip real estate can be used for accommodating the reagent and protein input wells. In addition to the protein reservoir that a user loads, two additional reservoirs can be included that the user can load. These additional reservoirs can, for example, be loaded with any user-selected additives such as glycerol or detergents. Additives can stabilize the proteins, e.g., to improve the quality and size of protein crystals. In another embodiment, the number of wells can be increased on-chip, as described in more detail above.

7.3.2.4 Reagent Loading Schemes

In order to not burden the user with filling 384 wells, all the reagents can be pre-filled and packaged in a facility so that the user only needs to introduce a drop of protein to the chip. For effective translation from nanobatch on-chip to microbatch off-chip, it is essential to tightly control the volume of the droplets. The droplets dispensed on the digital microfluidic platform are very precise with a CV<2% in nanoliter range.

This precision can be exploited in various reagent pre-filling schemes in conjunction with other loading methods. Outlined hereinbelow are a variety of suitable loading mechanisms:

1. Electric Field Mediated Dispensing: 384 loading reservoirs around the periphery can be loaded with respective reagents and the chip can be programmed to dispense a 10 nL droplet from all these wells and transport a droplet into each of the 384 screening wells. Each loading reservoir can, for example, hold at least 100 nL. This scheme has been demonstrated for dispensing 25 nL droplets from 4 loading reservoirs.
2. Pressure-Assisted Electric Field Mediated Dispensing: 12 loading ports in 96-well pitch can be placed on either side of the chip. 12 syringe pumps, arranged in 96-well pitch, can be arranged to first sip the reagents from a 96-deep well block of reagents. All the 12 pumps can be interfaced to the 12 loading ports to push the reagents and electric field can be used to create a surface energy well to trap a droplet. These droplets can then be transported away to the screening wells. This method has been successfully used to dispense multiple droplets simultaneously, and it is readily scalable to load 1536 reagents.
3. Multi-well Bulb Droppers: In this scheme, reagents can be prepared in a 384-deepwell plate. An array of droppers can be used to sip the reagents from the deepwell plate and drop the reagents into the loading ports on-chip surrounding 384-wells. 10 nL droplets can be dispensed from these loading ports and transported to the screening wells.

4. Robotic Pipetting: Robotic pipetting can deliver precise volumes into the screening wells.

7.3.2.5 Protein Loading

The chip can be programmed to precisely dispense 10 nL droplets 384 times from a single protein reservoir. This reservoir can be constructed to hold about 4 µL of protein. A polypropylene or polyethylene or polyester or silicone or any tape can be used as a sealing film to prevent evaporation through the loading ports during incubation. Microbatch experiments typically require a higher protein concentration compared to vapor diffusion experiments. In 800 experiments surveyed in the literature, 4 were set up at <2 mg/mL and 4 were set up at >300 mg/mL and a majority of the rest are set up in the 5 to 10 mg/mL range of protein concentration. Dispensing and transport of protein droplets with concentrations of 75 mg/mL has been demonstrated.

7.3.2.6 Optimization Chip Programmed to Set Up 96 Conditions

In this embodiment, an optimization chip is made and the system is programmed to set up 96 conditions from 2 reservoirs of stock solutions, 2 reservoirs of buffer, and 1 reservoir of water. Sparse matrix screening for crystallization requires a relatively predictable amount of protein and can be done in a single experiment. However, it is often the refinement of the initial crystallization hit that takes the longest time and uses the most material. Typically, upon getting a hit from a sparse matrix screen, an investigator will construct a series of grids around the index condition. Microbatch particularly requires fine grids for optimization after screening. This process involves a number of labor-intensive dilutions. It is very difficult to do this with current technologies on small volumes of proteins. In addition, human pipetting is only reliable in the microliter range with about ±10% volume variability and in a very fine grid this level of variability will not provide enough resolution between different conditions. Robotic pipetting is another option, but robots that are precise and accurate in single-digit nanoliter dispensing are costly. Therefore, the chips of the invention, which can dispense with <2% CV in the nanoliter-regime are a very cost-effective alternative to expensive fluid handling robots. A major advantage of digital microfluidics is the software programmability of fluidic operations due to electronic control of liquids. Therefore, this versatile feature can be exploited by fabricating chips that perform all the dilutions and create, initially, 96 fine grid conditions from 3 user-loaded constituent stock solutions of the salts, precipitants, and buffers.

The main difference between the screening and the optimization chip is that for the screening chip the reagents are pre-filled as the constituents of the reagents are discrete and fixed and for the optimization chip the reagents are constituted on-chip because the constituents of the reagents span the entire crystallization space and vary based on the lead condition. Other than robotic pipetting, no other microfluidic technology offers such high levels of programmability as is required for on-chip dilutions.

On-chip optimization is best illustrated by an example. Hsp90 crystallizes at a slightly acidic pH with PEG 4000 as the precipitant and ammonium phosphate as the salt. For example, 96 conditions were set up in a fine grid as follows: pH 4.6 and 5.6 (2 conditions), PEG 4000 in steps of 2% at 8%, 10%, 12%, 14%, 16%, 18%, 20%, 22% (8 conditions), and ammonium phosphate in factors of 2 at 50 mM, 100 mM, 200 mM, 400 mM, 800 mM, and 1600 mM (6 conditions).

From the above screen, Hsp90 crystallized at pH 4.6, 10% PEG, and 0.2M ammonium phosphate. If the user loads 2.5M ammonium phosphate into one of the on-chip stock solution reservoirs, there are a few ways of constituting 0.2M on-chip. In one scheme, 2 droplets of 2.5M solution can be mixed in an intermediate reservoir with 23 droplets of water in one step to get 0.2M solution. In this scheme, a total of 25 droplets are dispensed and used. In another scheme where intermediate dilutions are utilized, 2.5M would be first diluted to 1M in an intermediate reservoir by mixing 2 droplets of 2.5M solution with 3 droplets of water. In another intermediate reservoir, 1 droplet of 1M solution can be mixed with 4 droplets of water to get 0.2M solution. In this scheme, only 10 droplets are dispensed and used. This example serves to illustrate that dilutions can be performed to minimize reagent consumption for fine grid setup on-chip which minimizes the number of dispensing steps, thereby reducing the overall error in volume.

Reservoirs can be included for HCl, NaOH, and/or other reagent buffers to constitute a full range of pH values (e.g., pH 1-7 at various increments) on-chip through dilutions. Among other things, the advantages of using the envisioned chip for setting up the fine grid conditions are: low volume of protein used per condition (10 nL), automatic setup of 96 conditions inexpensively, and precision in droplet volumes (<2% CV). An example of the optimization chip is found in Table 8.

TABLE 8

| Digital microfluidic optimization chip specifications | |
|---|---|
| Protein Sample Reservoir | 1 |
| Reagents filled by user | 5 |
| Optimization Wells | 96 |
| Protein Reservoir Capacity | 100 droplets |
| Unit droplet volume | ~10 nL |
| Total Protein Volume Required | 1 µL |
| SBS multi-well plate Footprint | 88.48 × 127.76 mm$^2$ |
| Well-to-well pitch | 2.25 mm |

The optimization chips can, for example, include 5 loading ports; one each for the stock solutions of salt and precipitant, water, and two for buffers. Each chip can be capable of constituting 96 combinations of reagents from these 5 reservoirs. Two (2) additional loading ports can also be included for the optional inclusion of additives in the optimization phase. 96 optimization wells in a 1536-well foot print occupy $\frac{1}{16}^{th}$ of the chip area and the rest of the area can be used for the stock solution, intermediate, and waste reservoirs.

Fine grids can be set up on-chip in a variety of ways based on the condition that the smallest droplet that could be generated is 10 nL. If the stock solution reservoirs are large enough, large numbers of droplets could be combined directly with water droplets to set up any condition. This method minimizes the number of dilutions but requires many dispensing steps. Another method is to constitute the desired concentrations by using serial dilutions (binary, decade etc). Yet another method, as illustrated in the example, would combine both the above methods where a stock solution would be diluted in one step to within the proximity of required concentration and from that intermediate reservoir fewer droplets would be directly dispensed to set up the fine grid conditions. Based on the design architecture optimizing the layout and electrical connections, an optimum combination of reservoirs can be chosen for direct dispensing and serial dilutions.

The goal in these experiments is to rapidly mix 2-3 droplets within a reservoir. A number of schemes can be developed to perform rapid mixing within the reservoirs. For example, an n-electrodexn-electrode array can be used within the reservoir to rotate a droplet to enhance mixing.

For some user-defined concentrations of stock solution, it may not be easy to set up the required concentration range for the 8×6 conditions with the required intervals between the concentrations. For such cases, as an alternative, the software can be designed to calculate an optimum initial concentration of the stock solutions and prompt the user to load the same. Some of the additives, such as acetone, ethanol, methanol etc., may be miscible with the surrounding oil but it has been found that these additives do not partition into oil at the concentrations at which they are typically used (usually <40% w/v). However, the miscibility of any organic compounds is to be determined by the end user and an appropriate immiscible medium is to be used.

7.3.3 Protein Crystallization Screening and Optimization

In a demo of screening chip operation, 4 µL of protein can be loaded into a screening chip using a pipettor, screen script routine run, 384 protein droplets automatically dispensed and mixed up with 384 pre-filled reagents.

In a demo of an optimization chip operation, the user can load 1 µL of protein and stock solutions of salt and precipitant, buffers, and water using a pipettor, input concentration range and interval for a fine grid, run fine grid script routine, inform the user via software if any modifications to the stock solutions are required, cause the chip to constitute 96 fine grid conditions, dispense 96 protein droplets, and mix them with the reagents. If any reservoirs do not dispense, then the chip can automatically detect and run a reload script or if any droplet gets stuck on a pathway the software can automatically detect the failure and work around the fault. The user can incubate the chip and periodically check for crystals.

7.3.3.1 Crystal Screening in 384-Well Digital Microfluidic Systems

The user can replicate the initial screening step of protein crystallization using a screening chip and compare the results to those obtained by conventional microbatch crystallization. Several proteins can be subjected to this screening in order to assess comparisons with traditional microbatch screening.

The droplets in the chips can be flat and shaped as hockey pucks rather than as spherical droplets. This is advantageous for automated crystal scoring since image distortion due to optical aberrations would not be a concern. An x-y micrometer stage can be adapted to fit on a standard stereo-zoom microscope and the screening chip can be viewed manually or automatically translated to score for crystal hits within the wells by using image processing.

PCB chips are usually opaque but can be made transparent by filling the via-holes with a transparent epoxy if needed for visualization or polarization microscopy. In order to eliminate the possibility of finding salt crystals, the user can run a negative control chip to identify salt crystal formation or add a droplet of coomassie blue or methylene blue which fill the solvent channels in protein crystals. This selectively colors protein crystals blue and leaves salt crystals clear.

7.3.3.2 Optimization of Crystallization Hits Using the Optimization Chip

After obtaining the screening conditions, an optimization grid typically has to be set up. Within these grids, the concentration of one or two of the components of the sparse matrix crystallization reagent is varied. The choice of variable component and the grid size are based on the investigator's experience, and are limited by the amount of protein on hand, the geometry of the crystallization apparatus, and the time allotted to the experiment. Optimization is often an iterative process, as first one grid and then another is tested until the parameters governing crystallization in that particular region of crystallization space are understood. This is, however, a strategy that is limited in its breadth. For example, even in a simple crystallization setup there may be several components to vary, including precipitant and salt concentration, buffer pH, additives, as well as protein concentration, in addition to environmental variables such as temperature. A standard optimization strategy would usually first focus on constructing a grid of precipitant versus salt, wherein the precipitant concentration would be varied linearly and the salt concentration varied by a multiplicative factor (e.g. 2). After several days, the experiment would be evaluated and additional grids set up. A much more efficient strategy for optimization would vary as many components as possible in the same experiment. This becomes an attractive option especially if the sample requirements remain modest and the labor of setting up the multi-dimensional grids can be automated. The optimization chip offers both of these benefits, and the purpose of this experiment is to demonstrate that optimization grids can be constructed around an index sparse matrix condition that reproduces the original crystal and parameterize its growth conditions.

For any protein, a grid of conditions can be set up around the sparse matrix condition that yielded crystals. 96 conditions can be set up, varying at least 3 components: precipitant, salt, and pH. Initially the precipitant can be varied linearly, while the salt is varied by factors of 2, and the pH adjusted in 1 pH unit increments. Reagent droplets can be constituted from concentrated stock components and water on-chip, and then mixed with an equal volume of protein in an optimization well. For protein-ligand co-crystallization, after formation of crystals (for e.g., Hsp90) on-chip, the user can demonstrate soaking drugs (for example, radicicol, an antifungal antibiotic) with existing protein crystals on the optimization chip. If the crystals do not crack or become damaged, then the drug-bound protein crystals can be harvested in a capillary tube for X-ray diffraction. Protein-drug co-crystallization conditions can be similar to the protein-only crystallization conditions. The optimization chip can be also combined with the multiwell bulb dropper dispensing scheme to load 96 drug compounds from a high-throughput screening microplate directly onto this chip. In this case, the chip can be programmed to set up a single condition, which is known to give crystals, in all 96 wells. In this manner, multi-drug-single-crystal soaking studies can be performed. This demonstrates a few additional uses beyond optimization for the technology.

Bodenstaff et al., on the other hand, observed additional crystal forms, not observed in larger volumes, in 200-500 µL of lysozyme droplets. In cases where only tiny crystals are produced on the chips, or even different forms of crystals are observed, then a microfocus synchrotron beamline can be used for the analysis of the crystals. Such beamlines have proven to be useful for small crystal sizes in recent years. This becomes feasible since the chip allows for the movement of the drops containing crystals into a position on-chip where the crystals could be harvested into a capillary tube.

In short, this work demonstrates manipulation and setup of hundreds of droplets, a high throughput 384-well screening chip, and a programmable optimization chip for automated setup of optimization conditions through multiple dilutions programmed on-chip.

7.4 Droplet-Based Multiwell Plate Overview

According to another aspect, the chip of the present invention typically avoids the requirement for a continuous-flow approach, though chips of the invention may in some cases be supplemented by such an approach. Systems including chips of the invention provide flexibility and programmability that is comparable to robotic systems. The chips of the invention can manipulate droplets as small as a few nanoliters in volume. In certain embodiments, the chip of the invention specifically avoids networks of microchannels, external pumps, valves, high-voltage supplies and/or centrifugal force, though such components may be employed to supplement certain aspects of the invention. The system of the invention is scalable and allows multiple liquid droplets to be processed in parallel. The chip of the invention can be manufactured in a highly compact form, and it is inexpensive to manufacture. A schematic example chip 1000 is illustrated in FIG. 10 and includes a 96 well array 1002, a droplet transport network of electrodes 1004 for transporting droplets 1006, and a sample input module 1008.

7.4.1 Well Configurations

In one embodiment, the chips of the invention include a regular array of microliter-volume wells or reservoirs. The chip may also include a fluidic input module for loading bulk sample or reagent. A network of droplet transport pathways interconnects each of the wells and discrete nanoliter quantities of liquid can be transported between any two wells or inputs, e.g., to automatically and precisely generate an array of screening conditions. The wells and array of electrodes can be used to conduct a variety of droplet operations.

In some embodiments, wells can be physically defined by a polymer gasket material and linked together by a droplet transporter network defined by the pattern of electrodes on the chip surface. The standard pitch of the discrete electrode elements in the network establishes a unit droplet volume for the entire system. An open architecture in which reservoirs are defined by placement of reservoir electrodes is also possible.

In one embodiment, the chip dimensions conform to standard Society for Biomolecular Screening microplate (multiwell plate) dimensions, such as the dimensions set forth in "ANSI/SBS 1-2004: Microplates—Footprint Dimensions," as updated on Jan. 9, 2004; "ANSI/SBS 2-2004: Microplates—Height Dimensions," as updated on Jan. 9, 2004; "ANSI/SBS 3-2004: Microplates—Bottom Outside Flange Dimensions," as updated on Jan. 9, 2004; and "ANSI/SBS 4-2004: Microplates—Well Positions," as updated on Jan. 9, 2004. The entire disclosure of each of these documents is incorporated herein by reference for its teaching concerning microplate standards. For example, the design can be provided in standard 96 or 384-well or 1536-well format, as well as other custom formats. Use of standard well layout and spacing permits the chips of the invention to be compatible with conventional microplate equipment, such as pipette dispensers and read-out equipment. Standardized embodiments will enable integration of the chips of the invention into existing microplate systems and workflows.

Certain designs may combine microplate standards on a single device. For example, one portion of the chip may conform to 96-well format for loading of samples, while another portion conforms to 384 or 1536-format for arraying of reactions. Other designs may divide the chip into modules designed to perform different functions where some modules conform to multiwell plate spacing for loading, storing or detection of reagents or reactions while other modules may have structures designed to perform specific operations or procedures.

The chips of the invention are highly flexible and can accommodate specialized, non-standard conformations. Further, the number of wells on the chips of the invention can be much larger than provided for in existing microplate specifications. For example, chips of the invention can incorporate greater than 1,000, 5,000, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 200,000, 300,000, 400,000, 500,000, 600,000, 700,000, 800,000, 900,000, or even 1,000,000 sub-nanoliter reactions on a single plate.

Specifications for one embodiment of a 96 well plate are as follows in Table 9.

TABLE 9

Example specifications for 96 wells on a 128 mm × 86 mm plate (chip) size.

| Specification | Value |
| --- | --- |
| Well pitch | 9 mm |
| Array size | 12 × 8 (96 wells) |
| Transport electrode width | 0.75 mm |
| Unit droplet diameter | 0.75 mm |
| Unit droplet volume | 80 nL |
| Well volume | 800 nL (10 unit droplet volumes) |
| Plate spacing | 0.15 mm |
| Input ports | 10 |
| Input port volume | 8 µL (100 unit droplet volumes) |
| Overall chip size | 128 mm × 86 mm |

Figure 11:
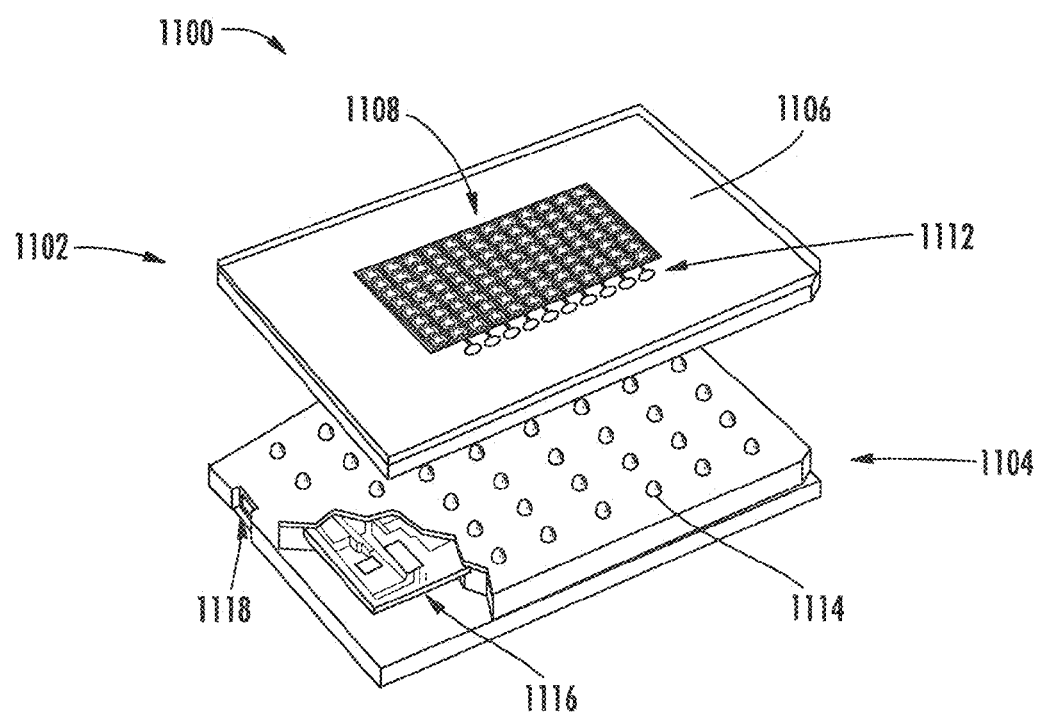
FIG. 11 is a perspective view of a PCB-based microactuator in accordance with an embodiment of the present invention.

A relatively low-density (96-1536 wells) PCB-based platform provides a basic and inexpensive assay automation tool. For example, referring to FIG. 11, in one embodiment, the invention provides a microactuator 1100 comprising a PCB-based chip 1102 that will plug into a base 1104 that conforms to the size and shape of a standard multiwell plate. The PCB chip 1102 can have a top plate 1106, a 96-well array 1108, and a fluid input module 1112. The base 1104 can have electrical contacts 1114 and a controller circuit board 1116. All of the electronics required to operate the chip 1102 can be integrated into the base 1104, e.g., with the electrical contacts 1114 distributed on the top-side of the base 1104 to make contact with the backside of the chip 1102. The entire instrument can be powered and controlled from a standard USB port 1118 or even operated as a stand-alone instrument. Power can be provided by batteries located within the plate so that the stand-alone plate provides completely automated fluid handling in the same form factor as a standard plate. This embodiment of an automated multiwell platform can perform many of the functions of a robotic system at a tiny fraction of the cost, and will be particularly useful in low and moderate throughput environments, including much of academic research, where the expense of robotic automation may be difficult to justify. Fluid handling capability is completely integrated within the unit which has standard plate dimensions and is compatible with conventional plate readers and handling equipment.

Larger chips with extremely high levels of throughput and cost savings will be useful in a variety of settings, such as drug discovery applications. In one embodiment, the invention is useful for high-throughput biological assays. For example, the chip can be programmed to execute on-chip dilutions and cell-handling protocols. Scaling of droplet volumes on a fully populated 128 mm×86 mm plate (chip) size at different well pitches can be seen in Table 10.

TABLE 10

Scaling of droplet volumes at different well pitches.

| Well Pitch (mm) | Rows | Cols | Total wells | Well volume (nL) | Unit drop diameter (μm) | Plate spacing (μm) | Unit drop volume (nL) | Min. feature (μm) |
|---|---|---|---|---|---|---|---|---|
| 9.00 | 12 | 8 | 96 | 6750 | 1500 | 300 | 675 | 75.0 |
| 4.50 | 24 | 16 | 384 | 844 | 750 | 150 | 84.4 | 37.5 |
| 2.25 | 48 | 32 | 1536 | 105 | 375 | 75.0 | 10.5 | 18.8 |
| 1.13 | 96 | 64 | 6,144 | 13.2 | 188 | 37.5 | 1.32 | 9.38 |
| 0.563 | 192 | 128 | 24,576 | 1.65 | 93.8 | 18.8 | 0.165 | 4.69 |
| 0.281 | 384 | 256 | 98,304 | 0.206 | 46.9 | 9.38 | 0.0206 | 2.34 |
| 0.141 | 768 | 512 | 393,216 | 0.0257 | 23.4 | 4.69 | 0.00257 | 1.17 |
| 0.070 | 1536 | 1024 | 1,572,864 | 0.00322 | 11.7 | 2.34 | 0.000322 | 0.586 |

Mixing or dilution ratios can be established programmably by controlling the number and distribution of constituent droplets delivered to each well. Furthermore, liquid which has been mixed within a well may be subsequently dispensed from that well in the form of unit-sized droplets for transport to another well, for example, to perform serial dilution assays.

7.4.2 Fluid Input

The invention includes a fluidic input module for loading and storage of samples and reagents. In one embodiment, a basic input module allows samples to be loaded using a pipettor or other device and automatically subdivides and distributes input fluid as discrete droplets to the multiwell array. When present, the input module serves as the interface between conventional fluid handling technology and the microfluidic chip architecture.

The fluid input module generally can include one or more sample loading reservoirs integrated with the multiwell array. The loading reservoirs may include a liquid reservoir connected to the network. The loading reservoirs are interfaced to the outside of the chip and will typically have much larger capacities than individual processing wells where the liquid is completely loaded or they may have smaller capacities but serve as an interconnection between the chip and the outside world where the liquid is continually fed. As a general rule, the target capacity of the loading reservoirs can be a multiple of the number of wells times the unit volume in cases where the liquid is completely loaded.

Thus, at least one unit droplet of each sample or reagent can be distributed to each well on the plate. Frequently used reagents such as dilution buffers can be loaded in multiple ports for greater parallelism or continually fed in through at least one dedicated loading port.

A general discussion of input reservoirs used in connection with the droplet microactuator of the present invention can be found hereinbelow with reference to Section 7.8.6.1.

7.4.3 Screening Capabilities

The invention provides a high-throughput interface for screening of large diverse libraries. Clearly, if thousands of compounds must be loaded at the chip's fluidic interface using conventional robotics, then the advantage of this platform is severely diminished. As such, while in some embodiments this limited approach was used for loading of small numbers of reagents for on-chip titration, in other embodiments a means was employed for rapidly populating the wells with a large number of different compounds. Various alternative embodiments may, for example, include 1) an interface in which droplets of compound are separated by plugs of oil in a long pre-loaded capillary (e.g., glass capillary) which when connected to the chip allows droplets of compound to be captured and routed on the chip as they are pumped out of the capillary, 2) an approach in which compounds are pre-stamped onto the chip and allowed to dry using a high-speed reagent stamping or printing process, or 3) a direct plate to chip interface in which the contents of conventional 1536 or 384 or 96 well plates can be transported to the chip in parallel by pressurizing the liquid to pass through openings at the bottom of the wells which are aligned to an array of chip inputs.

In some embodiments, the invention provides electronics and detectors integrated directly on the chip substrate to enable higher throughput and rapid readout of results. The use of glass or silicon substrates permit integration of microelectronic circuits and the array of droplet control electrodes on a single substrate. Integration of the drive electronics onto the chip would vastly increase the available number of electronic control signals permitting greater throughput and protocol optimization. The LCD screen found on a typical PDA such as a PalmPilot™ is roughly the same size as a multi-well plate and contains a 480×320 array of 153,600 independently controllable electrodes demonstrating that chip-level integration of electronics can be both feasible and relatively inexpensive. Integration of electronics onto the substrate provides the additional advantage that optical or electrochemical sensors could be integrated with the chip as well.

7.5 Droplet-Based Multiwell Plate Examples

The following non-limiting examples are provided only for the purpose of illustrating various aspects of this aspect of the invention and should not be construed as limiting the scope of the invention.

7.5.1 Scalable Chip Architecture for Droplet Distribution 7.5.1.1 Well Design

Individual wells can be defined on the chip using the same photopatternable polymer material (e.g., dry film soldermask) that defines the input reservoirs and provides the standoff between the two plates in the fully-assembled device. Each well can be designed with at least a single major opening to permit communication between the interior of the well and the distribution network for dispensing of droplets into and out of the well. Several minor openings may also be included to allow air bubbles to escape during filling of the device with oil.

The following parameters can be varied to optimize the performance (dispensed droplet volume variation, liquid capacity, ease of filling with oil, and resistance to shake-up during handling) of each well: major opening width and length, interior shape and size, location and size of minor openings, size and shape of electrodes, and chamber height.

The consistency of dispensed droplet volumes and liquid capacity of the wells have important consequences with respect to the capability of performing multi-step dilutions or mixing within the chambers. For example, if the volume of the dispensed droplet is found to depend on the volume of liquid remaining in the well, this issue can be corrected at the program compiler level by accounting for this variation.

7.5.1.2 Transporter Network Design

The droplet distribution network linking the individual chambers is another component of the multiwell array subsystem of the proposed platform. While the layout of the network is straightforward owing to the regularity imposed by the array, electrical connectivity and control of the electrodes presents a serious optimization challenge. Thus, for example, in an embodiment in which 10 transport electrodes are associated with each cell, up to 1,000 independent electrical control signals are required. In practice, no more than a few hundred signals can be inexpensively managed. One solution to this problem is to provide multiplexing of electrode control signals. That is, multiple electrodes are connected to a single signal and activated or deactivated together. For example, a transport line of arbitrary length can be implemented as a line of electrodes where every electrode is connected to one of three signals which are operated out of phase to transport all droplets on the line in unison. In this manner, many droplets can be arbitrarily manipulated in parallel, but the design and operation of the device is considerably more complex owing to lack of independent control of each electrode.

The fabricated multiwell platform can be arranged to provide optimal droplet routing. Due to the limited number of electronic control signals, droplets are preferably not routed independently of each other. In addition, fluidic constraints and overlapping droplet routes will dictate careful droplet scheduling. Computationally tractable algorithms can be used for the simultaneous coordination of a potentially large number of droplets. Limited row-column addressing schemes, where only entire rows and columns of droplets can be addressed, can be employed. The insertion of "wait cycles" at appropriate points during sample delivery, mixing, and dilution can also be employed.

7.5.2 Fluidic Input Module

The fluidic input module can include a smaller array of relatively large (~10 µL) reservoirs which can be pipette-loaded through access holes in the chip. The reservoirs store sample or reagent and dispense unit-sized droplets on demand for transport to particular well locations. The design of the input module is made challenging both by the need to physically interface with the outside world and by the need to precisely dispense the unit-sized droplets from a large, arbitrary volume.

Dispensing of unit droplets from the fluidic input is considerably more challenging than dispensing from the wells because the volume of the liquid reservoir compared to the dispensed droplet is considerably larger and more variable. Dispensing of droplets becomes inherently more challenging at larger ratios due to the larger difference in curvature between the initial and final droplets. As described by the Young-Laplace equation, this curvature difference creates a pressure gradient inside the liquid which opposes further deformation of the surface. Thus more energy is required to dispense droplets at large ratios (e.g., 100:1) than at smaller ones (e.g., 10:1). Furthermore, larger droplets of liquid are more susceptible to gravitational, buoyant and inertial effects because surface-tension is less dominant at this scale, leading to less reliable and repeatable manipulation of droplets by surface-tension-based effects.

In one embodiment, this problem is addressed using a multi-stage input comprised of a larger outer reservoir directly connected to a loading hole and outside world and a smaller inner reservoir connecting the outer reservoir with the multi-well array. The smaller inner reservoir is periodically reloaded from the larger reservoir and dispenses droplets directly onto the transport network. Dispensing of liquid from the larger to smaller reservoir need not be very precise, while the relative stability of the smaller reservoir volume ensures reproducibility of the unit droplet volume.

For example, one embodiment includes a fluid input module with fixed outer reservoir volume of 10 µL (100 unit droplets of 100 nL each) and inner reservoirs of various volumes ranging from 5 µL (50 unit droplets of 100 nL each) to 1.0 µL (10 unit droplets of 100 nL each). The entire 10 µL volume can be dispensed, reloading the smaller reservoir as many times as required, and the volume of each unit-droplet can be measured. The performance of each design in terms of volume reproducibility and throughput (including reload cycle time) can then be determined.

7.6 Droplet-Microactuator Stamping Platform Overview

Figure 12:
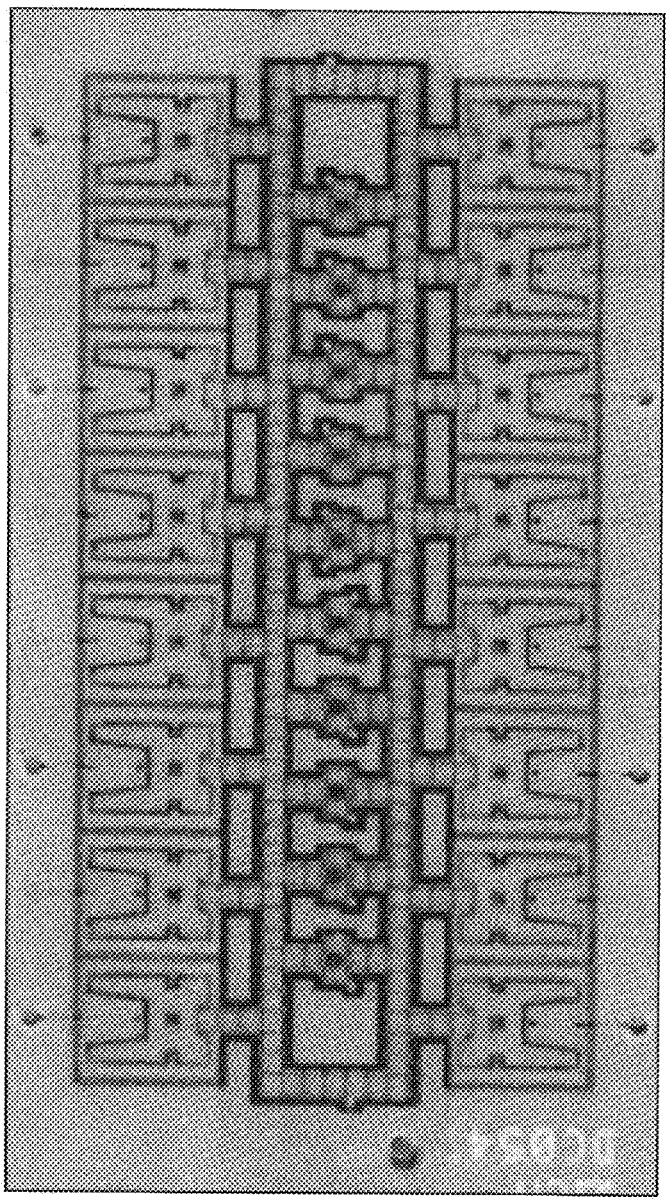
FIGS. 12 and 13 are illustrations showing electrowetting chips in accordance with an embodiment of the present invention.
Figure 13:
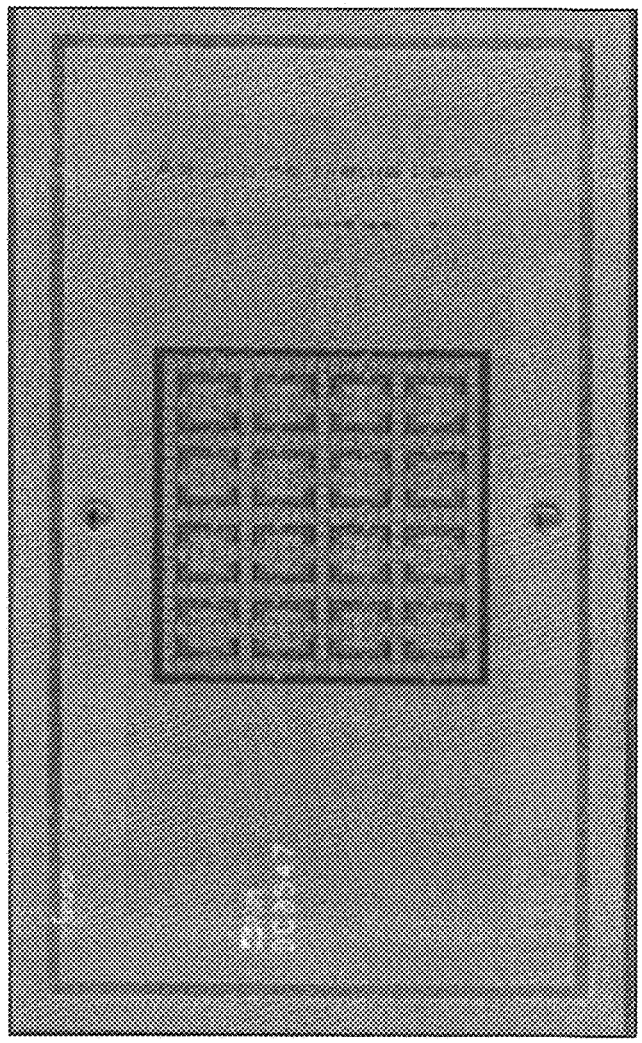

One further aspect of the present invention provides a droplet microactuator stamping platform. The platform provides, among other things, a system for droplet microactuator manipulation (e.g., dispensing, transport, mixing) of all fluids necessary for preparing samples for stamping operations. In particular, the invention provides mixing of MALDI matrix on-chip with samples and stamping onto a MALDI plate. FIGS. 12 and 13 illustrate two embodiments of droplet microactuator designs of the invention suitable for use as stamping platforms, wherein FIG. 12 is an electrowetting chip similar to that used in experiments described herein and FIG. 13 is an electrowetting chip on a 384 well footprint with 16 wells.

The invention includes openings for transporting droplets out of the chip to be stamped on a substrate. For example in one embodiment, the openings transport the droplets onto a plate. Typically, the surface of the plate will be substantially hydrophobic and will include hydrophilic spots where the samples will be deposited, e.g., for MALDI analysis samples will be deposited on these spots and will be interrogated by laser.

One key aspect of the invention is the ability to transport on a droplet microactuator the reagents and samples encountered in a typical MALDI-MS experiment. It was surprisingly found that droplets including proteins at concentrations relevant to MALDI-MS can be dispensed from on-chip reservoirs and transported on the droplet microactuator. Further, it was discovered that MALDI matrix containing acetonitrile can be dispensed, transported and manipulated on the droplet microactuator. Moreover, it was discovered that filler fluids used in electrowetting are compatible with MALDI-MS.

Certain embodiments of the droplet microactuator of the invention are capable of dispensing and transporting sample droplets that include proteins. A technique was surprisingly discovered which permits droplets with high concentrations of protein to be manipulated. In one embodiment, the protein solution has a concentration which exceeds about 1 mg/mL, about 10 mg/mL, about 50 mg/mL, or about 100 mg/mL.

Various embodiments of the droplet microactuator are also capable of manipulating reagent droplets comprising MALDI matrix. In a preferred embodiment, the droplet microactuator can dispense and transport reagent droplets comprising acetonitrile. The acetonitrile is typically provided in an amount which is sufficient to keep miscibility of the acetonitrile in the filler fluid at a level which is not unduly detrimental to the effectiveness of the stamping device. In one embodiment, the MALDI matrix comprises from about 40% to about 75% acetonitrile. In another embodiment, MALDI matrix comprises from about 50% to about 70% acetonitrile. In certain embodiments, the MALDI matrix may also include TFA. For example, in one embodiment, the MALDI matrix includes from about 0.05% to about 1% TFA. Thus, for example, in a preferred embodiment, the MALDI matrix includes from about 50% to about 70% acetonitrile and from about 0.05% to about 1% TFA.

Figure 14:
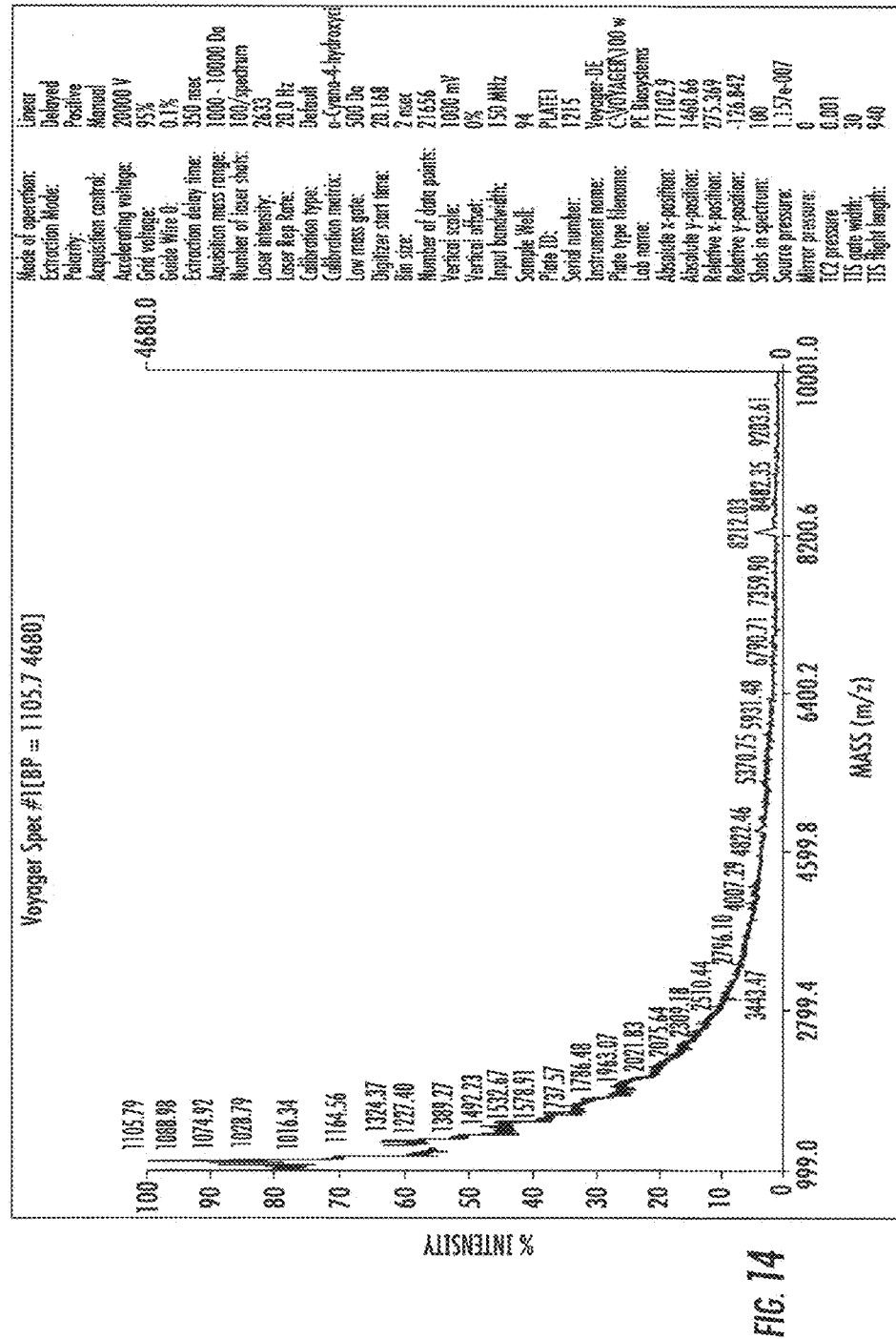
FIG. 14 is graph of the MALDI-TOF MS spectrum of oils depicting the % intensity as a function of mass.

The droplet microactuator typically includes a filler fluid, discussed in more detail hereinbelow with reference to Section 7.8.4. The filler fluid surrounds the droplets being transported. Low viscosity oils are preferred, preferably silicone oil. The MALDI-MS of silicone oil was evaluated and it was surprisingly found that the oil is highly compatible with MALDI-MS, producing no discernable peaks. FIG. 14 illustrates the MALDI-TOF MS spectrum of oil used in examples defined herein.

The system of the present invention is generally programmed and configured to mix sample droplets with MALDI matrix droplets on-chip to yield MALDI-ready droplets and to direct the MALDI-ready droplets to a port where some portion or the entire droplet can exit the droplet microactuator to be deposited on a MALDI substrate. In operation, droplets of sample and MALDI matrix are dispensed from on-chip reservoirs, mixed and spotted onto a substrate through an opening in the top plate (see aperture 1518 in FIG. 15). Passive stamping sometimes results in dead volume in the opening. In one embodiment, this problem is resolved by adding a small quantity of oil through one of the oil loading ports which provides enough pressure to force the liquid out of the opening completely.

In one embodiment, the sample and the MALDI matrix are merged at a stamping hole. Mixing is significantly faster using this approach due to the larger surface area available for diffusion in the hole.

Preferably, cross-contamination is reduced to a level at which it does not significantly impact analysis of deposited samples. In some embodiments, cross-contamination is reduced by reducing the acetonitrile concentration in the sample by dilution. Cross-contamination may also be reduced by minimizing the overlapping paths between different samples.

7.6.1 Droplet Manipulation

Figure 15:
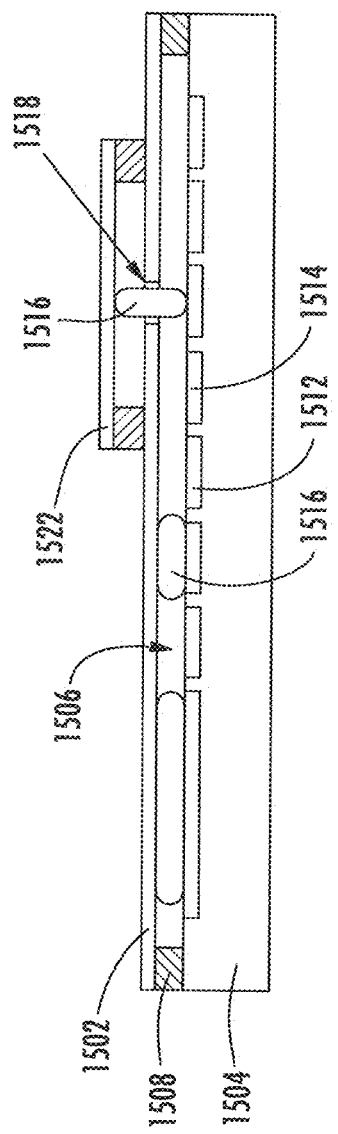
FIG. 15 is an illustration of a droplet microactuator stamping platform in accordance with an embodiment of the present invention.

The stamping platform of the invention makes use of a droplet microactuator chip which is useful for effecting droplet operations, such as dispensing, splitting, transporting, merging, mixing, agitating, and the like. Preferably, droplet manipulation is accomplished using electric field mediated actuation, as described hereinbelow with reference to Section 7.8. As illustrated in FIG. 15, the basic droplet microactuator 1500 includes two parallel plates, top plate 1502 and bottom plate 1504, separated by a gap 1506 formed such as through the use of spacers 1508. One or both of the plates 1502, 1504 includes one or more paths or networks of substantially planar control electrodes 1512 and corresponding reference electrodes 1514 for performing droplet manipulations. Droplets 1516 are interposed in the space 1506 between the plates 1502, 1504 on these paths or networks. Space 1506 surrounding the droplets is typically filled with a filler fluid as described hereinabove. Top plate 1502 may include a stamping aperture 1518 for the passing of a droplet 1516 through to a stamping plate 1522. The droplet microactuator 1500 works with a wide variety of liquid droplets, though conductive liquids are preferred.

Droplet transport for stamping occurs along the path or network of control electrodes. The path or network requires interconnections to electrically connect electrodes to contact pads for connection to external circuitry and may also include interconnections for connecting certain electrodes together. The droplet microactuator operates by direct manipulation of discrete droplets, e.g., using electrical fields. By applying different voltages to adjacent control electrodes, a local and electrically controllable energy gradient can be established. A droplet adjacent to an energized electrode will move to align itself with the energized electrode, i.e., the droplet will be transported to the position of that electrode. A series of successive transfers will transport droplets along the path or network of control electrodes. In addition to transport, other operations including merging, splitting, mixing and dispensing of droplets can be accomplished in the same manner by varying the patterns of voltage activation.

Further description of architecture and operations involving a droplet microactuator of the present invention can be found hereinbelow with reference to Section 7.8.

7.7 Droplet-Microactuator Stamping Platform Examples

The ensuing examples are illustrative of various embodiments of the invention, and should not be interpreted as limiting the scope of the invention. The examples provide, among other things, a demonstration of the feasibility of the droplet microactuator stamping platform described herein, including validation of on-chip manipulation (dispensing, transport, mixing) of all fluids of interest for the proposed application on a coplanar platform, and mixing of MALDI matrix on-chip with samples and stamping onto a MALDI plate.

7.7.1 Material and Methods

Figure 16:
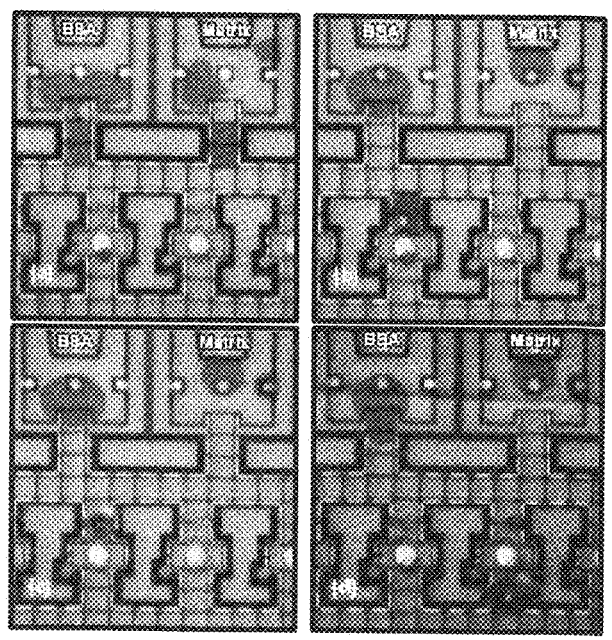
FIG. 16 is an illustration of time lapsed images of a stamping experiment in accordance with an embodiment of the present invention.

Protein samples were provided by LEAP or were obtained from SIGMA. MALDI-TOF MS was done by Global Peptide Services, Colorado. FIG. 12 shows a chip used in the experiments. FIG. 16 shows time lapsed images of a stamping experiment accomplished using the chip of FIG. 12. FIG. 13 shows another chip which was fabricated on a 384-well pitch with 16 wells.

7.7.2 Material Compatibility Studies

The compatibility of the various materials encountered in a typical MALDI-MS experiment was established by demonstrating the following.

1) Dispensing and transport of a representative set of protein droplets at concentrations relevant to MALDI-MS from on-chip reservoirs.

2) Dispensing and transport of MALDI matrix which contains acetonitrile.

3) Compatibility of filler fluids used in electrowetting with MALDI-MS 7.7.2.1 Protein Compatibility Table 11 lists proteins that were tested on the system along with the highest tested concentrations. Note that some of these concentrations are the highest "tested" and up to 10 s of mgs/mL of protein has been successfully dispensed and transported on the chips. This is three orders of magnitude higher than what is typically seen in MALDI-MS applications.

TABLE 11

Protein compatibility chart

| Protein | Highest concentration tested |
|---|---|
| BSA | 90 fmol/uL (6 ug/mL) |
| Bovine insulin | 100 pmol/uL (573 ug/mL) |
| Lysozyme | 75 mg/mL |

TABLE 11-continued

Protein compatibility chart

| Protein | Highest concentration tested |
|---|---|
| Glucose isomerase | 10 mg/mL |
| Proteinase K | 10 mg/mL |

The BSA sample was in 25% ACN (provided by LEAP Tech) and the bovine insulin (from SIGMA) was in 1% TFA. In addition to the above proteins, the manipulation of sample matrices containing high concentration of proteins such as whole blood, plasma and serum have been shown.

7.7.2.2 Solvent/MALDI Matrix Compatibility

The most commonly used solvent to prepare a MALDI matrix is 50-70% acetonitrile with 0.05-1% TFA. Though 100% acetonitrile is partially miscible (3-5%) in the oils typically used for electrowetting, a mixture of acetonitrile and water (up to 70% ACN) was not measurably miscible in oil. Droplets were successfully manipulated containing up to 70% acetonitrile on the system. MALDI matrix droplets containing 50% ACN and 0.05% TFA was also successfully dispensed and manipulated on the chip.

7.7.2.3 Filler Fluid Compatibility

In order to prevent fouling of the surfaces, the use of low viscosity oils is preferred as the filler media surrounding the droplets. The MALDI-MS of the silicone oil commonly used was evaluated and no discernable peaks >3000 Da were found. FIG. 14 shows the mass spectra of oil. The small peak which is visible at 8212 Da is from the MALDI matrix.

7.7.3 System Scaling and Integration

System integration and scaling was demonstrated as follows:

1) Mixing of protein droplets with MALDI matrix droplets on-chip.
2) Passive stamping through an opening or an "open" system onto a top plate which is hydrophobic all over the surface except for the hydrophilic spots where the MALDI samples will be interrogated by laser.
3) Evaluating the effect of cross contamination between the droplets either mediated through oil or the surfaces.
4) Determining the effect of aspect ratios on stamping.
5) Investigating use of droplets digitized and deposited directly from the well plate obviating the need for a top plate. Determine operational limitations of this approach.

7.7.3.1 Stamping of Single Sample

FIG. 15 illustrates the setup used to perform the MALDI stamping experiment. BSA (90 nM in 25% ACN) was used as the model protein for the stamping experiments. Droplets of sample and MALDI matrix were formed from on-chip reservoirs, mixed and passively spotted onto a glass plate through an opening in the top plate. The droplets were approximately 100 nL each. Passive stamping sometimes resulted in dead volume being left over in the opening. This problem was resolved by adding a small quantity of oil through one of the oil loading ports which provides enough pressure to force the liquid out of the hole completely.

In a variation of the stamping experiment described above, the sample and the MALDI matrix were merged at the stamping hole. Mixing is expected to be significantly faster using this approach due to the larger surface areas available for diffusion in the hole.

7.7.3.2 Stamping of Multiple Samples

The previous experiment was scaled up to demonstrate the passive stamping of four different BSA droplets. The mixing with the matrix was done at the stamping hole in this experiment.

7.7.3.3 Cross-Contamination Studies

Figure 17:
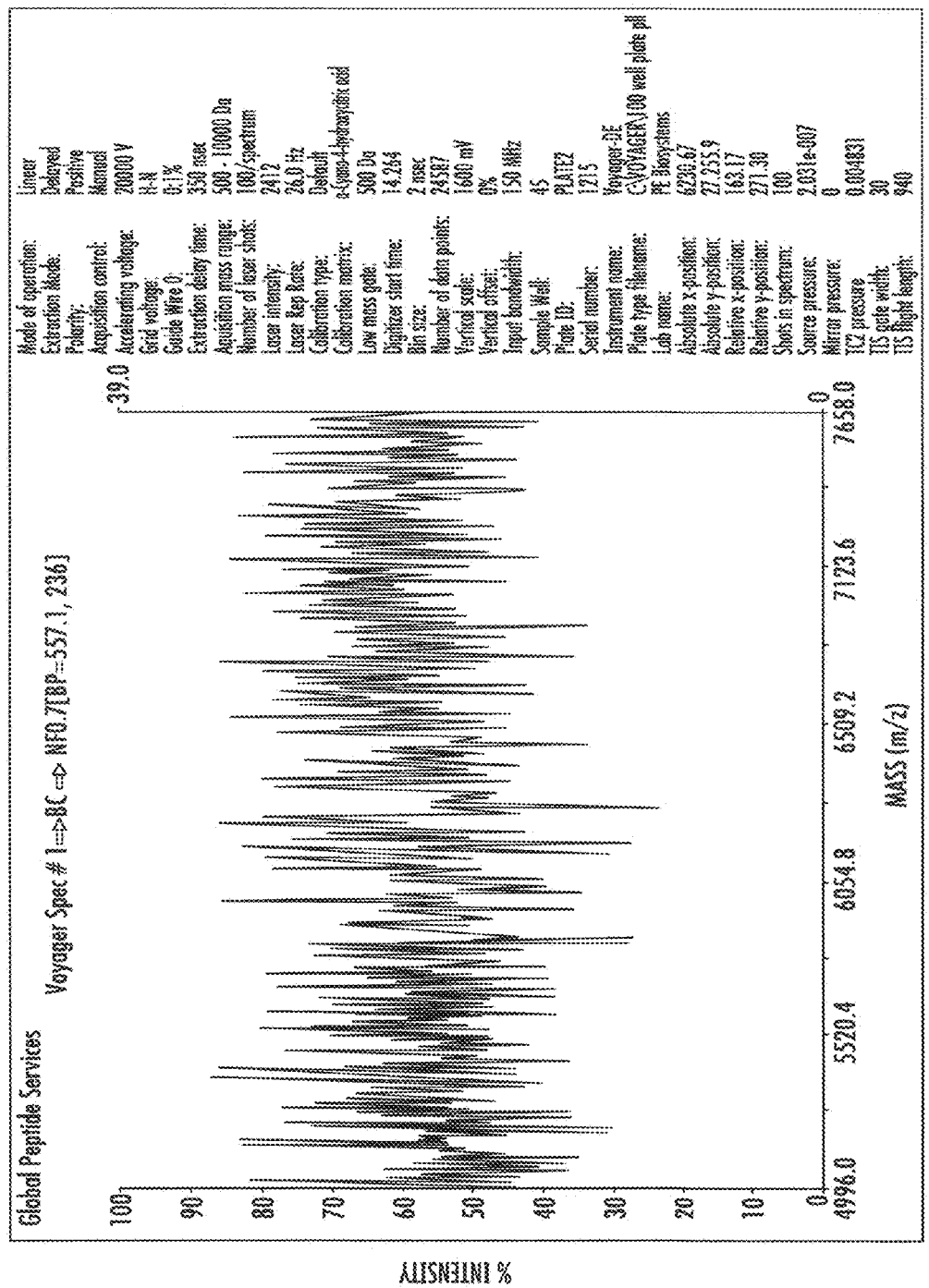
FIGS. 17 and 18 are graphs of the MALDI-MS for a blank droplet after cross-contamination experiments and depicting the % intensity as a function of mass.

Cross-contamination studies were performed to evaluate the carryover of protein samples from one droplet to another. In the first experiment, several droplets (total volume ~500 nL) of 100 pmol/uL insulin (total insulin manipulated=50 pmol) in 1% TFA were moved across 6 electrodes several times and collected through the stamping hole. The total time the insulin droplets resided on the 6 electrodes was approximately 5 minutes. A water droplet was also moved on the same path as the protein droplet for approximately 5 minutes and collected through a different stamping hole. 5 uL of matrix was added to both the samples and MALDI-TOF MS was done by spotting the entire sample. FIG. 17 illustrates MALDI-MS for a blank droplet after cross-contamination experiments without acetonitrile in the system. The figure shows the spectrum and no peaks are visible at the molecular weight of insulin. The lowest detectable concentration obtained by doing MS analysis on a dilution curve was 2.5 fmol of insulin. As such, the cross-contamination from a 50 pmol sample is below 2.5 fmoles (carryover of 0.005%) and is not detectable by the instrument used.

Figure 18:
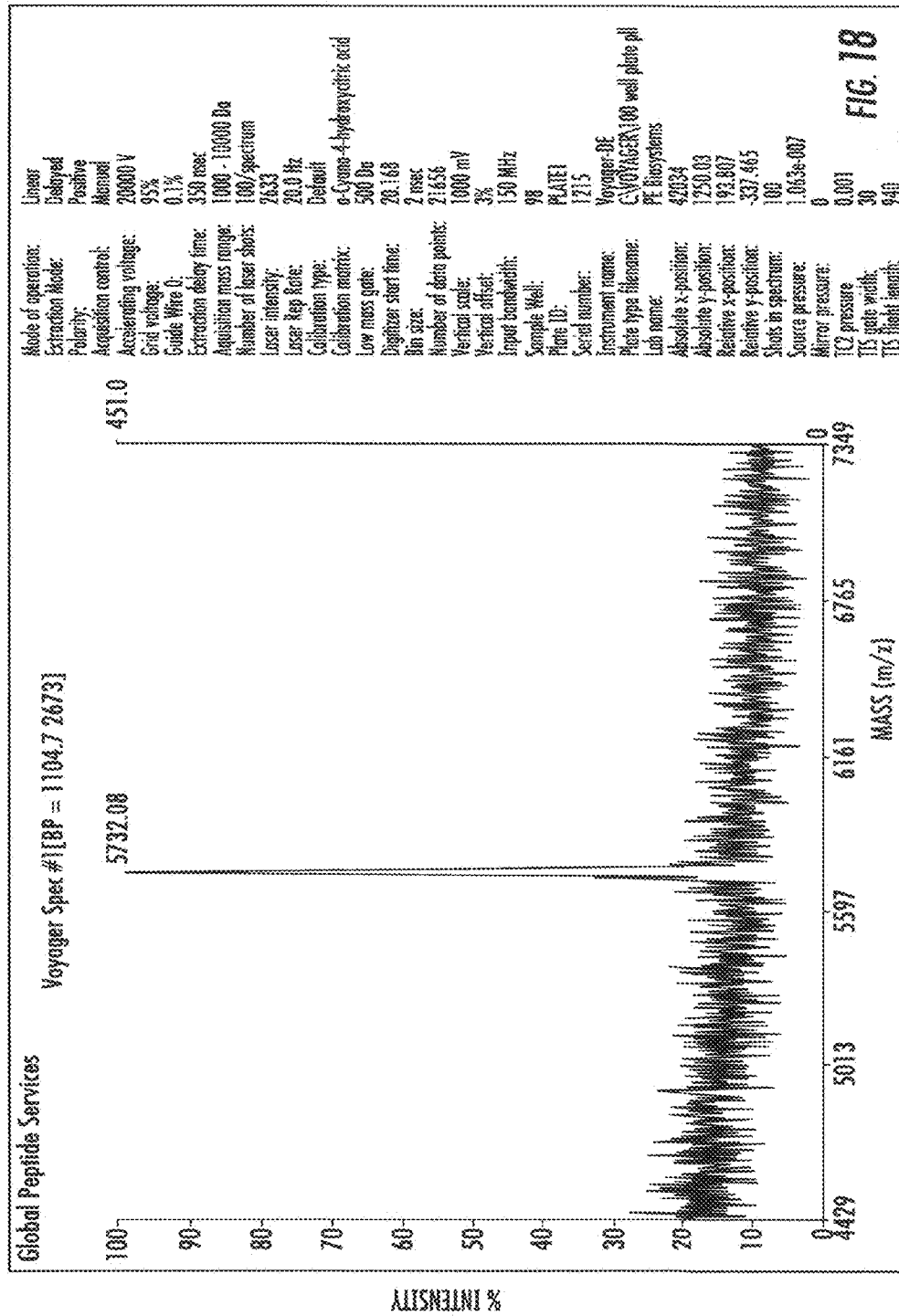

In the second experiment the protein sample and a blank sample were both premixed with the MALDI matrix to see if the presence of acetonitrile increased the possibility of contamination. Four 100 nL droplets of 100 pmol/uL insulin (40 pmol) with matrix were transported across 12 electrodes serially and discarded to waste. Four 100 nL droplets of the blank droplet (with matrix) was moved along the same path and collected through a stamping hole. The collected droplet was stamped as is without any additional matrix added to it. FIG. 18 illustrates MALDI-MS for a blank droplet after cross-contamination experiments without acetonitrile in the system according to this experiment. The figure shows the zoomed mass spectrum of the blank droplets and a peak is visible at the molecular weight of insulin. This indicates that there is some cross-contamination. To estimate the levels of cross-contamination a log dilution series of insulin between 2.5 fmoles and 250 pmoles was also analyzed using MALDI-MS. The intensity of the peak (baseline corrected) for the different samples analyzed is shown in Table 12.

TABLE 12

Mass-spec peak intensity for different samples

| Sample | Peak intensity (baseline corrected) |
|---|---|
| 250 pmol | 1743 |
| 25 pmol | 4339 |
| 2.5 pmol | 5816 |
| 250 fmol | 333 |
| 25 fmol | 114 |
| 2.5 fmol | no peak |
| Blank | 383 |

From the table, it can be inferred that the cross-contamination from a 40 pmol sample is around 250 fmol which amounts carryover of 0.625%. A similar carryover was seen when both the sample and the blank were collected through the same hole.

This cross-contamination can be attributed to the presence of acetonitrile in the samples (from the matrix) since no contamination was observed using an aqueous sample of proteins. Without wishing to be bound by a particular theory, it is suspected that microdroplets are ejected during manipulation. It is believed that by changing the geometry of the electrodes, the ejection of microdroplets can be reduced or eliminated. Cross-contamination can also be minimized by reducing the acetonitrile concentration in the sample by dilution, and by minimizing the overlapping paths between different samples.

7.7.4 Stamping Platform Conclusions

Among other things, the work described herein demonstrates the feasibility of the stamping platform of the invention. A droplet microactuator of the invention can dispense and transport protein samples with high protein content, MALDI-specific solvents, and MALDI matrix. An oil matrix can be used to prevent proteins from sticking to electrodes. There are limitations on the percentage of acetonitrile solvent in the sample liquids used but these limits do not substantially impair the utility of the device. Mixing of the MALDI matrix with sample materials on chip can be accomplished as expected. Stamping through a hole in the top plate is a feasible embodiment of the invention. Less than 1% carryover appears to occur when very low protein concentration solution droplets follow the same path as high protein concentration solution droplets.

7.8 Droplet Microactuator Architecture and Operation

The various aspects of the present invention discussed hereinabove generally include a droplet microactuator controlled by a processor. For example, the processor may, among other things, be programmed to control droplet manipulations on a droplet microactuator. A wide variety of droplet microactuator configurations is possible. Examples of components which may be configured into a droplet microactuator of the invention include various filler fluids which may be loaded on the droplet microactuator; fluid loading mechanisms for introducing filler fluid, sample and/or reagents onto the droplet microactuator; various reservoirs, such as input reservoirs and/or processing reservoirs; droplet dispensing mechanisms; means for controlling temperature of the droplet microactuator, filler fluid, and/or a droplet on a droplet microactuator; and magnetic field generating components for manipulating magnetically responsive beads on a droplet microactuator. This section discusses these and other aspects of the droplet microactuator and their use in the systems of the invention.

7.8.1 Droplet Microactuator

The various aspects discussed hereinabove can make use of a droplet microactuator, sometimes referred to herein as a chip. The droplet microactuator can include a substrate with one or more electrodes arranged for conducting one or more droplet operations. In some embodiments, the droplet microactuator can include one or more arrays, paths or networks of such electrodes. A variety of electrical properties may be employed to effect droplet operations. Examples include electrowetting and electrophoresis.

In one embodiment, the droplet microactuator includes two or more electrodes associated with a substrate, and includes a means for permitting activation/deactivation of the electrodes. For example, the electrodes may be electronically coupled to and controlled by a set of manual switches and/or a controller. The droplet microactuator is thus capable of effecting droplet operations, such as dispensing, splitting, transporting, merging, mixing, agitating, and the like. Droplet manipulation is, in one embodiment, accomplished using electric field mediated actuation. Electrodes will be electronically coupled to a means for controlling electrical connections to the droplet microactuator.

The basic droplet microactuator includes a substrate including a path or array of electrodes. In some embodiments, the droplet microactuator includes two parallel substrates separated by a gap and an array of electrodes on one or both substrates. One or both of the substrates may be a plate. One or both substrates may be fabricated using PCB, glass, and or semiconductor materials as the substrate. Where the substrate is PCB, the following materials are examples of suitable materials: Mitsui BN-300; Arlon 11N; Nelco N4000-6 and N5000-30/32; Isola FR406, especially IS620; fluoropolymer family (suitable for fluorescence detection since it has low background fluorescence); and the polyimide family. Various materials are also suitable for use as the dielectric component of the substrate. Examples include: vapor deposited dielectric, such as parylene C (especially on Glass), and parylene N; Teflon AF; Cytop; and soldermasks, such as liquid photoimageable soldermasks (e.g., on PCB) like Taiyo PSR4000 series, Taiyo PSR AUS series (good thermal characteristics for applications involving thermal control), and Probimer 8165 (good thermal characteristics for applications involving thermal control); dry film soldermask, such as those in the Dupont Vacrel family; and film dielectrics, such as polyimide film (Kapton), polyethylene, and fluoropolymers like FEP, PTFE. Some or all of the substrate may also include a hydrophobic coating. Suitable examples include Teflon AF; Cytop; coatings in the Fluoropel family; silane coatings; fluorosilane coatings; and 3M Novec electronic coatings.

Where the droplet microactuator includes two plates, droplets may be interposed in the space between the plates. Space surrounding the droplets typically includes a filler fluid. The droplet microactuator can conduct droplet operations using a wide variety of fluid droplets, though conductive fluids are preferred. Filler fluids are discussed in more detail hereinbelow with reference to Section 7.8.4.

Surfaces of the droplet microactuator are typically coated with a hydrophobic coating. For applications involving thermal cycling, a hydrophobic coating should be selected that is resistant to thermal stress during prolonged thermocycling operation. Examples of suitable thermal resistant materials include soldermasks such as Probimer® 8165 which has been developed for use in the automotive industry and has excellent thermal shock resistance, and PCB board materials such as Mitsui BN-300 which is resistant to high temperature and warpage.

Droplet transport occurs along a path or network of control electrodes. The array or path includes electrical connections for electrically coupling electrodes to external circuitry. The array or path may also include electrical connections for electrically coupling certain electrodes together. The electrodes can be controlled via the external circuitry by a processor. Droplet operations may be effected by supplying voltage to the electrodes. While the preferred voltage varies depending on the thickness of the dielectric, for a dielectric constant in the range of 2-100 and thickness in the range of 1 nm to 10 mm, the preferred energy per unit area limits are in the range of about 300 microjoule/sq meter to about 300000 microjoule/sq meter. The preferred activation voltage is in the range of about 1 mV to about 50 kV, or about 1V to about 10 kV, or about 5V to about 1000V, or about 10V to about 300V.

Typically, the electrodes are fired via a voltage relay. The droplet microactuator operates by direct manipulation of discrete droplets, e.g., using electrical fields. For example, a droplet adjacent to an energized electrode with surrounding electrodes grounded will transport to align itself with the energized electrode, i.e., the droplet will be transported to the position of that electrode. A series of successive transfers will transport droplets along the path or network of control electrodes. In addition to transport, other operations including merging, splitting, mixing and dispensing of droplets can be accomplished in the same manner by varying the patterns of voltage activation.

It should be noted that electrodes can be activated in a variety of ways. For example, an electrode can be activated by applying a DC potential. Similarly, an electrode can be activated by applying an AC potential, so that the activated electrode has an AC potential and an unactivated electrode has a ground or other reference potential. In another aspect, the potential may be applied by repeatedly activating an electrode and then inverting it. An AC mode can be effected by using software to rapidly switch between polarities of the outputs.

In some embodiments the invention employs droplet operation structures and techniques described in U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on Jan. 30, 2006; U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000, both to Shenderov et al.; U.S. Patent Publication No. 20060254933, entitled "Device for transporting liquid and system for analyzing" published on Nov. 16, 2006 to Adachi et al.; International Patent Application No. PCT/US 06/47486, entitled "Droplet-Based Biochemistry," filed on Dec. 11, 2006; and International Patent Application No. PCT/US 06/47481, entitled "Droplet-Based Pyrosequencing," filed on Dec. 11, 2006, the disclosures of which are incorporated herein by reference for their teachings concerning structures and techniques for conducting droplet operations.

Droplet operations can be rapid, typically involving average linear velocities ranging from about 0.01 cm/s to about 100 cm/s, or from about 0.1 cm/s to about 10 cm/s, more preferably from about 0.5 cm/s to about 1.5 cm/s. Moreover, droplets may typically be manipulated at a frequency of manipulation ranging from about 1 Hz to about 100 KHz, preferably from about 10 Hz to about 10 KHz, more preferably from about 25 Hz to about 100 Hz. In addition to being rapid, droplet manipulations using the droplet microactuator are also highly precise, and multiple droplets can be independently and simultaneously manipulated on a single droplet microactuator.

Discrete droplet operations obviate the necessity for continuous-flow architecture and all the various disadvantages that accompany such an architecture. For example, near 100% utilization of sample and reagent is possible, since no fluid is wasted in priming channels or filling reservoirs. Further, as noted above, droplet movement can be extremely rapid. The droplet microactuator may in some cases be supplemented by continuous flow components and such combination approaches involving discrete droplet operations and continuous flow elements are within the scope of the invention. Continuous flow components may be controlled by the controller. Nevertheless, in certain other embodiments, various continuous flow elements are specifically avoided in the droplet microactuator of the invention and/or methods of the invention. For example, in certain embodiments, one or more of the following components is excluded from a droplet microactuator and/or methods of the invention: microchannels; fixed microchannels; networks of microchannels; pumps; external pumps; valves; high-voltage supplies; centrifugal force elements; moving parts.

Electric field mediated actuation also obviates the need for other droplet operations and all the various disadvantages that accompany such techniques. It will be appreciated that the droplet microactuator may nevertheless be complemented or supplemented with other droplet manipulation techniques, such as electrical (e.g., electrostatic actuation, dielectrophoresis), magnetic, thermal (e.g., thermal Marangoni effects, thermocapillary), mechanical (e.g., surface acoustic waves, micropumping, peristaltic), optical (e.g., opto-electrowetting, optical tweezers), and chemical means (e.g., chemical gradients). When these techniques are employed, associated hardware may also be electronically coupled to and controlled by the controller. However, in other embodiments, one or more of these droplet operation techniques is specifically excluded from a droplet microactuator of the invention.

The droplet microactuator can be manufactured in a highly compact form and can be driven using a very small apparatus. For example, droplet microactuator and apparatus may together be as small as several cubic inches in size. The droplet microactuator requires only small amounts of electrical power and can, for example, readily be operated using batteries. The droplet microactuator can perform droplet operations using extremely small droplets. Droplets are typically in the range of from about 1 fL to about 1 mL, more preferably from about 100 pL to about 1 µL, still more preferably from about 10 nL to about 1 µL.

The use of discrete droplets for on-chip processing instead of continuous flows provides several important advantages. Since sample fluid need not be expended for priming of channels or pumps virtually all of the sample fluid can be used for analysis and very small volumes of sample (e.g., less than about 100 µL or less than about 50 µL or less than about 25 µL) can be analyzed. The same advantages apply to the use of reagents where reducing the volume of reagents consumed has the advantage of reducing the cost of the analysis. The use of discrete small-volume droplets also permits a large number of reactions to performed in a small footprint (e.g. greater than 10 per $cm^2$ or greater than 100 per $cm^2$ or greater 1,000 per $cm^2$ or greater than 10,000 per $cm^2$).

Various components of the invention may be included as components of the droplet microactuator. In fact, an entire system of the invention may be provided as an integrated droplet microactuator. In some embodiments, the droplet microactuator includes various sensors and means for electronically coupling the sensors to external circuitry. In other embodiments, the droplet microactuator includes heaters and/or magnetic field generating elements and means for coupling such elements to external circuitry. Further, a droplet microactuator including any one or more of the reagents described herein in a reservoir or in droplet form is also an aspect of the invention.

Optical windows can be patterned in the electrodes to enhance the capability of performing optical detection on the chip. Where the electrode is formed in an opaque material on a transparent substrate, a window in the electrode can be created permit light to pass through the substrate. Alternatively, when the electrode material is transparent, a mask can be created to eliminate stray light. Additionally, the opening can be patterned as a diffraction grating. Adaptive optical windows can be created as well, using a second electrowetting layer. For example, opaque oil (e.g. oil dyed black) can be used with a transparent droplet to create a temporary and movable optical window.

7.8.2 Droplet Microactuator Fabrication

Droplet microactuators can be made using standard microfabrication techniques commonly used to create conductive interconnect structures on microdroplet microactuators and/or using printed-circuit board (PCB) manufacturing technology. Suitable PCB techniques include those described in U.S. patent application Ser. No. 11/343,284, entitled "Apparatuses and Methods for Manipulating Droplets on a Printed Circuit Board," filed on Jan. 30, 2006, the entire disclosure of which is incorporated herein by reference. These techniques permit the droplet microactuator to be manufactured in bulk at very low cost. Low cost manufacture enables economical production of droplet microactuators, even for use as one-use disposables. Thus, the invention provides a method in which droplet microactuators are supplied to users as components of disposable cartridges for use in systems of the invention.

Designs can also be implemented on glass or silicon using conventional microlithography techniques with the capability of producing much smaller features than are typical in a PCB process. Even, for example, for a 1,572,864-reservoir droplet microactuator with 70 μm reservoir spacing and 3 fL reservoir volume, the minimum required lithographic feature size is ~0.5 μm which is well within the capabilities of conventional microlithographic techniques currently used in the semiconductor industry.

Because the chip can be loaded directly using manual or robotic pipette dispensers and can be analyzed using standard plate reading equipment, it will easily integrate into existing laboratory work flows. This is a significant advantage over other microfluidic approaches which may require adaptation of the assays to continuous-flow format or specialized equipment for sample handling and read-out.

7.8.3 Cartridge

In some embodiments, the invention includes a cartridge for coupling to the droplet microactuator. It will be appreciated that a cartridge, while not necessary to the operation of the invention, may be convenient in some circumstances. When present, the cartridge may include a means for electrically coupling the path or network of the droplet microactuator to a processor, e.g., a processor of a droplet microactuator system of the invention. In this embodiment, the electrical connection is: electrodes—cartridge—processor, where there may be additional elements between the three. In another embodiment, the cartridge may include means for physically coupling to the droplet microactuator. In this embodiment, the electrical connection may be: electrodes—processor—cartridge. Alternatively, the cartridge may lack electrical components altogether.

When present, the cartridge may include reservoirs for one or more reagents, e.g., pre-loaded reagents. The droplet microactuator may be configured so that a fluid path may be established between the cartridge reservoirs and the interior of the droplet microactuator for flowing reagents, sample and/or filler fluid from the cartridge onto the droplet microactuator. For example, preloaded cartridge reservoirs may be dispensed into the droplet microactuator prior to, during, or after coupling of the cartridge to the analyzer. The cartridge may be sealed, self-contained and/or disposable. It may be supplied with or without a droplet microactuator. Such cartridges can be used to ensure repeatable assay conditions, permit safe handling and disposal of infectious or hazardous material, and/or reduce cross-contamination between runs. The cartridge may, for example, include a machined plastic part. It may be affixed to and provided in combination with the droplet microactuator.

The cartridge materials are selected to provide storage of reagents without degradation or contamination of the reagents. Moreover, they should be selected to provide reliable operation at elevated temperature and to ensure compatibility with the real-time chemistry. They may, for example, include molded plastic components. In some embodiments, sealed, disposable test cartridges enhance operator safety and facilitate safe disposal.

Various components of the droplet microactuator system may be included on the cartridge. For example, the top-plate, which encloses the interior space of the droplet microactuator, may be provided as a component of the cartridge. Various sensors may also be included as components of the cartridge.

7.8.4 Filler Fluid

The droplet microactuator of the invention includes one or more free (i.e., fluid-fluid) interfaces. Examples include a liquid-liquid or liquid-gas interface. Typically chemistry is performed in the primary (droplet) phase, and the secondary phase serves as a filler fluid separating the droplets from each other. The secondary phase can, for example, be a liquid, gel, and/or a gas. Where the secondary phase includes a liquid, the liquid is sufficiently immiscible with the primary liquid phase to permit the droplet microactuator to conduct one of more droplet operations.

It should also be noted that the droplet microactuator may include more than two phases. For example, in one embodiment the droplet microactuator operates based on an aqueous-oil-air three-phase system. In a related environment, the droplet microactuator may operate based on an aqueous-first oil-second oil three-phase system, such as a system including an aqueous droplet surrounded by silicon oil, which is in turn surrounded by a fluorosilicon oil. Generally, three-phase systems will include three components which are mutually immiscible or substantially immiscible.

In another embodiment, oil or another immiscible liquid may be used as a droplet encapsulant for electrowetting. For example, a droplet can be encapsulated in a shell of oil by moving the droplet through an air/oil interface. Each droplet would then have its own local bath of oil with the space between encapsulated droplets filled with either air or a third immiscible liquid. Among other advantages, this approach is useful for minimizing the transfer of material between droplets in the system by partitioning into the oil phase while retaining the advantageous properties of the oil with respect to evaporation and fouling of the surface. This approach may also be used to facilitate electrowetting of non-electrowettable liquids which are immiscible with electrowettable liquids. In a specific embodiment of this concept the immiscible liquid can be chosen to be crosslinkable (by UV, heat, moisture or chemically) to create capsules of liquids with solid shells, for drug delivery synthesis applications.

Further, in some applications it may be desirable or necessary to perform certain operations in an immiscible liquid, such as oil, and others in air. The invention includes hybrid systems in which droplet manipulation is performed both in air and in an immiscible liquid filler fluid such as oil. For example, samples may be processed under oil and then transported into an air-medium portion for evaporation for subsequent analysis, for example, by MS. Conversely, a sample could be collected in air and then processed with droplets under oil. Thus, the droplet microactuator may include a transport path for moving droplets from a droplet microactuator surface in a space filled with filler fluid to a droplet microactuator open to the atmosphere or including a gaseous filler fluid.

The filler fluid may be any fluid in which the droplet microactuator can, under the right conditions, conduct one or more droplet operations. It should be noted that certain filler fluids may be solids or highly viscous fluids under certain conditions, e.g., during transport, while they are transformed into fluids for operation, e.g., by heating. The filler fluid may be a liquid or gas during operation of the droplet microactuator.

Examples of suitable liquid filler fluids include, without limitation, silicone oils; fluorosilicone oils; hydrocarbons, including for example, alkanes, such as decane, undecane, dodecane, tridecane, tetradecane, pentadecane, hexadecane; aliphatic and aromatic alkanes such as dodecane, hexadecane, and cyclohexane, hydrocarbon oils, mineral oils, paraffin oils; halogenated oils, such as fluorocarbons and perfluorocarbons (e.g. 3M Fluorinert liquids); mixtures of any of the foregoing oils in the same class; mixtures of any of the foregoing oils in different classes. Examples of suitable gas filler fluids include, without limitation, air, argon, nitrogen, carbon dioxide, oxygen, humidified air, any inert gases. In one embodiment, the primary phase is an aqueous solution, and the secondary phase is air or an oil which is relatively immiscible with water. In another embodiment, the filler fluid includes a gas that fills the space between the plates surrounding the droplets. A preferred filler fluid is low-viscosity oil, such as silicone oil. Other suitable fluids are described in U.S. patent application Ser. No. 11/639,594, entitled "Filler Fluids for Droplet Operations" filed on Dec. 15, 2006, the entire disclosure of which is incorporated herein by reference. The fluid may be selected to prevent any significant evaporation of the droplets.

The phases of the fluids used in the protocols of the invention may be selected to facilitate protocols of the invention without undue formation of bubbles, loss of reagent to the filler fluid, and/or adherence of reagent to the droplet microactuator surface.

In certain embodiments of the invention the filler fluid may be selected to reduce or prevent evaporation of sample, reagent, or other droplets utilized in the protocols of the invention. The filler fluid may be selected to prevent sample, reagent, or other droplets utilized in the protocols of the invention from evaporating and becoming too small for further effective manipulation. Similarly, the filler fluid can be selected to prevent evaporation of sample, reagent, or other droplets utilized in the protocols of the invention from detrimentally concentrating species within the droplets in a manner which results in an unduly adverse affect on the intended use of the droplet. Moreover, the filler fluid may be selected to reduce or prevent transport of material from sample, reagent, or other droplets utilized in the protocols of the invention across the phase boundary to maintain droplet volume and/or ensure reliable microfluidic operation and/or assay results. Miscibility between phases can sometimes result in shrinking (or swelling) of the droplet phase. To prevent or reduce this problem, one or more phases of the system may be saturated with the equilibrium concentration of another phase to reduce shrinking or swelling. Thus, for example, the filler fluid may be saturated with the equilibrium concentration of the solvent for sample, reagent, or other droplets utilized in the protocols of the invention, and/or one or more of the sample, reagent, and/or other droplets utilized in the protocols of the invention may be saturated with the equilibrium concentration of the filler fluid.

In some embodiments, a liquid filler fluid is selected to minimize contact between the droplet and droplet microactuator surfaces. That is, a film of liquid may exist between the droplet and surface which prevents material within the droplet from coming into contact with and adhering to the coated surface. This approach helps to prevent fouling of the surface and related interference with droplet transport. For example, it has been observed that high concentrations of certain proteins in water droplets readily stick to certain hydrophobic surfaces spoiling the hydrophobic nature of these surfaces; whereas, the same droplets can be moved across the same surfaces without appreciable adhesion of proteins if bathed in an oil which minimizes contact between the two surfaces. This approach may also help to avoid cross-contamination between droplets caused by deposition of material from one droplet which is then picked up by a second droplet. In a similar embodiment, a film between the droplet and droplet microactuator surface can be used to lubricate the droplet by preventing friction-like physical interactions between the droplet and surface during droplet operations.

In one embodiment, the invention provides a thin coating of a liquid filler fluid layer in an otherwise gas filled system. For example, the invention provides a microfluidic system including an open or enclosed system including a thin layer of filler fluid, such as oil, layered on a droplet microactuator surface, wherein the system is otherwise filled with a gas. The oil is of sufficient thickness to provide lubrication and contamination of droplet microactuator surfaces and contamination of droplets via droplet microactuator surfaces. Preferably the oil is selected to minimize transport of material between the droplet and oil phases. One advantage of this approach is reduction of carry-over in the droplet microactuator. The surface may in some embodiments be treated by coating it with the filler fluid while operating in air. This approach is also useful for loading operations as a means to retain the lubricating effect of oil while avoiding trapping of oil bubbles in the bulk filler fluid.

Treatment of a Teflon AF surface with silicone oil can provide some of the lubrication benefit of silicone oil filler fluid even when operating in air. This approach can be used to prime the droplet microactuator with a lubricating layer of oil, followed by replacement with air to allow samples to be loaded without introduction of bubbles, followed by re-introduction of oil to prevent evaporation of the samples. Thus the benefits of each kind of system are available depending on the type of microfluidic processing to be carried out.

In another embodiment, the filler fluid can be completely exchanged at different steps within a protocol. For example, a gas filler fluid can be introduced during sample loading to prevent trapping of air bubbles and then a liquid filler fluid can be pumped in to prevent evaporation of the liquid. Different types of filler fluid can be pumped into or out of the system depending on the particular assay steps to be performed.

In yet another embodiment, multiple filler fluids can be used within a single system. For example, a droplet microactuator can be selected to have separate gas filled and liquid filled regions. Operations or certain types of droplets can be segregated between the different filler fluid regions.

The filler fluid may be selected based on its refractive index to either match the droplet to prevent refraction of light passing through or near the droplet. Alternatively the filler fluid may be selected with a refractive index that differs from the droplet to provide contrast for certain types of optical measurements or optical manipulations. A filler fluid may be chosen to have a lower index of refraction than the primary liquid so that light can be transmitted though the primary liquid by total internal reflection. The primary phase can include highly elongated droplets which can serve as "light pipes" to convey light between two locations, e.g. to facilitate optical analyses.

The filler fluid may be selected based on its color to facilitate direct or indirect visualization of the droplet, e.g., by providing contrast between the sample, reagent, and/or other droplets used in the protocols of the invention and the filler fluid. This approach can enhance visualization of the different phases, for example to distinguish droplets from filler fluid or from air bubbles. In optical applications, the differential absorbance of the two phases can be used to modulate the color of light passing through the system. As another example, in applications where fluorescence measurements are made within droplets it may desirable for the oil to include molecules, such as dyes, that absorb the emitted wavelength of light to minimize cross-talk between reactions occurring in adjacent droplets.

The filler fluid may be selected to have particular thermal properties that can either thermally insulate the droplets or conduct heat away from the droplets. For example, in the amplification protocols of the invention, a thermally conductive or low heat capacity filler fluid may be desirable to permit rapid changes in temperature. For applications where a steady temperature is required, a thermally insulating or high heat capacity filler fluid can be used to provide temperature stability.

The filler fluid may be selected to undergo a phase change upon presentation of an appropriate stimulus. For example, a wax-like filler fluid (e.g. paraffin wax or octadecane) can be used where the filler fluid is changed from solid to liquid form by application of heat. Lowering the temperature would return the filler fluid to a solid so that droplets would be contained within a solid matrix. Encapsulation of the liquid phase within a solid may facilitate storage and handling of the sample, reagent, and/or other droplets utilized in the protocols of the invention and/or allow for safe and convenient disposal of the materials following use of the droplet microactuator. The filler fluid can be stored as a solid on the droplet microactuator, in a cartridge-based reservoir, or elsewhere, and heated to permit the fluid to flow into and fill the droplet microactuator. Or the immiscible filler fluid can be selected to be crosslinkable (by UV, heat, moisture or chemically) to create capsules of liquids within a solid shell.

The filler fluid may be selected to have particular gas permeability or saturation properties. In certain applications a reaction occurring inside the droplet may consume oxygen or other gas which may need to be replenished by gas contained within or transported through the filler fluid. For example, some fluorinated oils have useful gas permeability properties for such applications. Alternatively, the filler fluid may be selected to exclude certain gases from the droplet, for example to maintain anaerobic conditions within the droplet. The filler fluid may be selected to have a certain degree of miscibility or partitioning into the droplet phase. Usually, complete or substantially complete lack of miscibility between the droplet and filler fluid is desired, but some applications may benefit from some limited degree of miscibility between the phases or partitioning of particular molecules between the phases, e.g., liquid-liquid extraction applications. In certain applications where dissolved gases in the filler fluid may be problematic, a means for degassing the filler fluid prior to or during use may need to be provided. For example, filler fluid may be degas sed by incubation under vacuum, heating, sparging or by centrifugation.

The filler fluid may be selected to have a particular surface or interfacial tension with the droplet phase or with the droplet microactuator surfaces. Surfactants can be added to the filler fluid to stabilize liquid films that may be present between the droplet and solid phases. Examples of suitable surfactants include nonionic low HLB (hydrophile-lipophile balanced) surfactant. The HLB is preferably less than about 10 or less than about 5. Suitable examples include: Triton X-15 (HLB=4.9); Span 85 (HLB 1.8); Span 65 (2.1); Span 83 (3.7); Span 80 (4.3); Span 60 (4.7); and fluorinated surfactants.

Surfactants are preferably selected and provided in an amount which (1) results in more droplet operations on the droplet microactuator as compared to corresponding droplet microactuator without the surfactant; or (2) makes one or more droplet operations possible on the droplet microactuator as compared to corresponding droplet microactuator without the surfactant; or (3) makes one or more droplet operations more reliable on the droplet microactuator as compared to corresponding droplet microactuator without the surfactant. In a related example, surfactants are preferably selected and provided in an amount which makes one or more droplet operations possible or more reliable for droplets including one or more specific reagents or mixtures on the droplet microactuator as compared to droplet operations for the same droplets including one or more specific reagents or mixtures on a corresponding droplet microactuator without the surfactant. In another related example, surfactants are preferably selected and provided in an amount which makes one or more droplet operations possible or more reliable for one or more droplets including amphiphilic molecules on the droplet microactuator as compared to droplet operations for the same droplets including amphiphilic molecules on a corresponding droplet microactuator without the surfactant.

In a preferred embodiment, the surfactant is added to the filler fluid in an amount which ranges from about 0.001 to about 10% w/w, or about 0.001 to about 1% w/w, or about 0.001 to about 0.1% w/w. For example, in one embodiment the filler fluid is 2 cSt silicone oil and the surfactant is Triton X-15 in an amount which ranges from about 0.001 to about 10% w/w, or about 0.001 to about 1% w/w, or about 0.001 to about 0.1% w/w. The solid-liquid interfacial tension may be adjusted to control the wetting of the filler fluid on the droplet microactuator surfaces, for example, to control the formation, thickness or behavior of thin films of the filler fluid between the droplet and droplet microactuator surfaces or to control the wetting behavior of the fluid when filling or emptying it from the droplet microactuator.

By doping filler fluid with surfactant, it was discovered that it is possible to increase the concentrations of compatible protein solutions by more than 3 orders of magnitude, from mg/L to mg/mL. The inventors were able to reliably dispense and transport 25 nL droplets of 75 mg/mL lysozyme solution using the new filler fluid. For example, the filler fluid may be silicone oil doped with a surfactant, such as Triton X-15. Preferably the surfactant is a lipophilic surfactant. In one embodiment, 0.1% (w/w) Triton X-15, a lipophilic surfactant, was added to the oil so that high concentrations protein droplets could be formed or dispensed from on-chip reservoirs. Droplet transport for all compatible fluids is fast (typically about 3-10 cm/sec) and reliable (>25,000 operations). In one embodiment, the filler fluid includes a surfactant dopant in an amount which results in an increase in the concentration of a protein that can be reliably dispensed on the droplet microactuator.

The filler fluid may be selected to have a particular viscosity or volatility. For example, a low viscosity liquid (e.g. 0.65 cSt. Silicone oil) facilitates transport of droplets while a low volatility filler fluid (e.g., 2, 5 or 10 cSt. Silicone oil) may be desirable to prevent loss of filler fluid by evaporation. In some applications, evaporation of the filler fluid can be desired, so a low volatility filter fluid may be selected. The filler fluid may be selected to have a particular viscosity dependence on temperature, since the viscosity of the filler fluid affects the fluid dynamics and the temperature on the droplet microactuator may vary.

The filler fluid may be selected to have particular electrical properties. For example, certain applications including electrowetting favor the use of a filler fluid that is non-conductive (e.g., silicone oil). Or the dielectric permittivity can be selected to control the coupling of electrical energy into the system from external electrodes. In certain applications a non-conductive filler fluid can be employed as an electrical insulator or dielectric in which the droplet floats just above the electrodes without physically contacting them. For example, in an electrowetting system a layer of filler fluid (e.g., silicone oil) between the droplet and electrode can be used to provide electrostatic control of the droplet. Filler fluids may be deionized to reduce conductivity.

The filler fluid may be selected to have a particular density relative to the droplet phase. A difference in density between the two phases can be used to control or exploit buoyancy forces acting upon the droplets. Examples of two-phase systems useful in this aspect of the invention include water/silicone oil, water/flourinert, and water/fluorosilicone oil. When one phase is buoyant, then that effect can be exploited in a vertical configuration as a means to transport one phase through the other. For example, a waste or collection well can exist at the top or bottom of the droplet microactuator where droplets are delivered to that reservoir by simply releasing them at an appropriate point and allowing them to float or sink to the target destination. Such an approach may be suitable for use in removing reactant from a droplet microactuator, e.g. removing fluid containing amplified nucleic acid for use in other processes. Density differences can also be used as a means to control or engineer contact between the droplets and droplet microactuator surfaces. For example, a droplet not normally contacting a top-plate can be released to sink or float to that surface to contact it. Density differences and buoyancy effects can also be exploited for sensing applications in which the movement of droplets is detected and related to a change in position, orientation or acceleration.

The filler fluid is selected for material compatibility with the droplet microactuator surfaces. For example, certain filler fluids can etch, dissolve, contaminate, absorb into or otherwise be incompatible with certain droplet microactuator materials. For example, fluorinated hydrocarbons, such as Fluorinert, may be incompatible with Teflon AF or Cytop surfaces because of their tendency to dissolve these materials, while silicone oils may be incompatible with PDMS surfaces due to the tendency of these materials to dissolve each other.

The invention may include means for controlling the introduction or circulation of the filler fluid within the droplet microactuator, cartridge and/or system. In one mode of operation the filler fluid is injected once during the initialization of droplet microactuator operation. The filler fluid may be provided from an external source using a syringe, dropper, pipettor, capillary, tube or other means. Alternatively, the filler fluid may be provided from a reservoir internal to the droplet microactuator assembly or cartridge. As an example, the fluid can be contained within a sealed pouch which is punctured or compressed to transfer the liquid into the droplet microactuator.

In another mode of operation a means can be provided for multiple introductions or recirculation of one or more filler fluids within the droplet microactuator. A secondary fluid-handling system can be provided to inject and to remove fluid from within the droplet microactuator. Pressure, gravity or other means such as the use of thermal gradients can be used to transport the filler fluid into or out of the droplet microactuator. Such a system can, for example, be used for the following purposes:

(1) To replenish filler fluid lost to evaporation or leakage over time. A slow steady flow or periodic injection of filler fluid can be employed to make up for any loss of filler fluid volume.
(2) To provide "clean" filler fluid either continually or periodically to reduce contamination between droplets. The filler fluid can be cleaned either by completely replacing it or by circulating it through a filter or bed of absorbent material selected to remove contaminants.
(3) To provide a means for transporting droplets to waste. For example, at the end of an assay, droplets can be released and allowed to flow with the filler fluid to the outlet providing a means to "flush" the droplet microactuator. Flushing the droplet microactuator can be performed to reset the status of the droplet microactuator in preparation to perform additional assays.
(4) To exchange the filler fluid when different fluids may be desired for certain steps, for example to replace oil with air to allow drying of droplets, or to replace one oil with a different oil.
(5) To provide a means of controlling the temperature of the droplets by heating or cooling the fluid as it is circulated through the droplet microactuator. The temperature of the filler fluid entering and leaving the droplet microactuator can be directly measured and the temperature and flow rate of the filler fluid can be adjusted to provide optimal temperature control inside the droplet microactuator.

Local regions of filler fluid or even individual units of filler fluid for each droplet can be used. For example aqueous droplets can be encapsulated in an individual shell of fluid, such as oil, which moves along with that droplet. Each such droplet would then have its own local fluid bath with the space between encapsulated droplets filled with third immiscible liquid such as air or fluorosilicone oil. This approach can be used to minimize the transfer of material between droplets in the system by partitioning into the oil phase while retaining the advantageous properties of the oil with respect to evaporation and fouling of the surface. The shells of oil can be created by simply moving the droplet through an oil interface, pinching off a unit of oil as the droplet creates a bulge along the interface.

Hybrid systems can be implemented in which different regions of the droplet microactuator are filled with different fluids. For example, samples can be processed under oil and then transported into an air portion to be evaporated for subsequent analysis by MS. Conversely, a sample can be collected in air and then processed under oil.

Magnetically responsive beads can be used to move material between oil and water phases on a droplet microactuator. Generally, water-soluble compounds or materials tend to remain within the droplets, unable to cross the oil-water meniscus in significant quantities, and oil-soluble compounds or materials remain in the lipophilic filler fluid. When the material is attached to magnetically responsive beads, a magnetic field may be used to move the beads and attached material across the oil-water boundary. The beads need to be selected such that they have sufficient affinity for oil and water so that they can readily cross the meniscus. This operation is useful for drying or concentrating materials and can also be used to facilitate washing and/or dilution. For example, material bound to a magnetically responsive bead can be removed from one droplet and transferred by way of the filler fluid to another droplet.

Filler fluid can be circulated through the droplet microactuator to reduce contamination during and/or between runs. Filler fluid can be continually or periodically flowed through the droplet microactuator, so that fresh filler fluid is constantly supplied to the droplet microactuator. In addition to removing contaminates contaminated oil, this technique could be used at the end of a run to clear droplets from the array by removing the voltage so that droplets are released and flow with the oil to an exterior of the droplet microactuator and/or into a waste reservoir.

7.8.5 Droplet Microactuator Loading

The droplet microactuator as contemplated herein generally includes one or more input ports for the introduction of one or more filler fluids, reagents and/or samples (e.g., reagents and/or samples for conducting protocols and/or assays as described elsewhere herein) into the droplet microactuator. In some embodiments, samples or reagents are loaded via the input ports using conventional robotics. In one alternative embodiment, droplets of sample or reagent are separated by plugs of oil in a long pre-loaded capillary (e.g., a glass capillary) which when connected to the droplet microactuator allows droplets of sample or reagent to be captured and routed on the droplet microactuator as they are pumped out of the capillary into the input port. Another loading technique involves pre-stamping reagents onto the droplet microactuator and allowing them to dry, e.g., using a high-speed reagent stamping or printing process. Yet another approach involves the use of a direct plate-to-droplet microactuator interface in which the contents of plates, e.g., 1536 or 384 or 96 well plates, are transported onto the droplet microactuator in parallel by using pressure to force the contents through input ports aligned with wells. Loading hardware may in some embodiments be electronically coupled to and controlled by the controller.

The droplet microactuator can be associated with or coupled with a fluidic input module for loading and storage of sample and/or reagent. For example, a basic input module allows samples to be loaded using a pipettor or other device. The system may be programmed to subdivide and dispense input fluid as discrete droplets which can be transported on the control electrodes networks or pathways.

7.8.6 Reservoirs

The droplet microactuator as contemplated herein may include various reservoirs (sometimes referred to herein as "wells"), such as input reservoirs and/or processing reservoirs.

7.8.6.1 Input Reservoirs

In some embodiments, the droplet microactuator includes one or more input reservoirs (also referred to as "loading wells") in fluid communication with one or more input ports, typically in direct fluid communication with the input ports. The input reservoir(s) serve as reservoirs for storage of bulk source material (e.g. reagents or samples) for dispensing droplets (e.g. reagent droplets or sample droplets). Thus, the input reservoir(s) may, for example, serve as sample wells or reagent wells.

The input reservoirs generally include one or more well reservoirs defining an interior space and an opening. The interior space defined by the well walls is at least partially isolated by the well walls from the remainder of the interior of the droplet microactuator. The reservoir may be adjacent (in any direction, e.g., vertically or laterally) to a port suitable for introduction of fluid from an exterior of the droplet microactuator into the input reservoir. One or more openings in the reservoir walls may be provided to enable fluid communication with the interior volume of the droplet microactuator for dispensing of droplets into this interior volume. The opening(s) may permit fluid to flow or be transported into the interior volume of the droplet microactuator onto the path or network of electrodes. Input reservoirs may also include one or more vents for permitting displacement of filler fluid from the input reservoir as fluid is introduced into or removed from the well via the port or the opening.

The input reservoirs may further include one or more planar control electrodes in a top or bottom plate adjacent to or within the space defined by the well walls. The planar electrodes can be electronically coupled to and controlled by the controller. In a preferred embodiment, the planar electrode has two or more branches or rays, such that activation of the control electrode during droplet dispensing in the presence of a fluid exerts a "pull" on the fluid in a direction which is generally opposite to the direction of droplet dispensing. In some cases, the shape of the electrode results in a multi-vector pull having a mean vector which has a direction generally opposite to the direction of the droplet being dispensed.

Well walls may, for example, be formed by protrusions from the top or bottom plates, and/or may be formed by deposition of a wall-forming material on a surface of the top or bottom plate. For example, well walls may be formed from a soldermask material or polymeric gasket material deposited and patterned on the surface. In some embodiments a source of continuous or semi-continuous sample or reagent flow is coupled in fluid communication with one or more of the input ports.

It should be noted that while droplet dispensing may be conducted from defined reservoirs, in some embodiments, droplet dispensing is conducted without the use of physically defined reservoirs. Dispensing may proceed from source droplet which is confined during droplet dispensing, e.g., by electrowetting forces or by hydrophilic surfaces.

7.8.6.2 Processing Reservoirs

The droplet microactuator may also include one or more processing wells, areas, or reservoirs. These reservoirs serve as a location for executing various droplet processing steps, such as mixing, heating, incubating, cooling, diluting, titrating, and the like. The droplet microactuator includes one or more paths or networks of control electrodes sufficient to transport droplets from the one or more input ports to the one or more processing reservoirs. In some cases the processing reservoirs are simply components or sections of these paths or networks. In other embodiments, the processing reservoirs are defined processing reservoirs. Such reservoirs may, for example, be structured generally in the same manner as the input reservoirs described above. However, the processing reservoirs are typically not in direct fluid communication with the input ports, i.e., droplet transport along the one or more paths or networks of control electrodes is required add reagent or sample to the processing reservoir(s). In some cases, the processing reservoirs include a path or network of reservoirs therein to permit droplet operations within the processing reservoirs. Other configurations of the reservoirs or wells of various aspects of the present invention are discussed hereinabove with reference to Section 7.4.1.

Mixing or dilution ratios can be established programmably by controlling the number and distribution of constituent droplets delivered to each reservoir. Furthermore, liquid which has been mixed within a reservoir may be subsequently dispensed from that reservoir in the form of unit-sized droplets for transport to another reservoir, for example, to perform serial dilution assays.

7.8.7 Thermal Control

The droplet microactuator of the invention may include a means for controlling the temperature of the droplet microactuator or a region of the droplet microactuator. Among other things, thermal control is useful for various protocols requiring heating or cooling steps. Examples include amplification protocols requiring thermal cycling and various assays that require incubation steps.

7.8.7.1 Thermal Control Designs

In general, thermal control may be provided in three ways: (1) thermal control of the entire droplet microactuator; (2) thermal control of a region of a droplet microactuator using a heater that is in contact with or in proximity to the controlled region; and (3) thermal control of a region of the droplet microactuator using a heater that is integrated into the droplet microactuator (e.g., in the substrate comprising the path or array of electrodes and/or in a top plate of the droplet microactuator, when present). Combinations of the foregoing approaches are also possible.

In an integrated heater approach, temperature zones can be created and controlled using thermal control systems directly integrated into the droplet microactuator. Integration of thermal control through thin-film heating elements fabricated directly on the droplet microactuator is also useful to maximize the speed, throughput and quality of amplification reactions on the droplet microactuator. Due to their small thermal mass, droplets can be thermally cycled extremely rapidly. Thermal control is enhanced by locating the heating elements proximate to the droplets and reducing the parasitic thermal losses between the heater and the droplet. Heating elements can be integrated into the top plate and/or bottom plate of the droplet microactuator.

Integrating heating elements onto the droplet microactuator also enables the use of multiple distinct thermal zones within the droplet microactuator. This permits multiple steps in an analysis, such as sample preparation and thermal cycling, requiring different temperatures to be performed simultaneously on different portions of the droplet microactuator. Droplets can be physically transported or "shuttled" between zones of different fixed temperatures to perform the thermal cycling aspects of the amplification reaction. This approach can produce even faster reactions, since heating and cooling of the entire thermal zones is no longer rate-limiting. Instead, heating and cooling rates are determined by the time required to transport the droplets between the zones and the time required for the droplet temperature to equilibrate to the temperature of the zone once it arrives within the zone, both of which are expected to be very fast. A further advantage is that reaction steps can be "queued" rather than "batched" to permit greater operational flexibility. For example, discrete samples can be continuously fed into the droplet microactuator rather being delivered at a single point in time.

Droplets may be thermally cycled in batch mode using a single heater or in flow-through mode by circulating the droplets through distinct temperatures zones created by the heating elements. The essential difference between batch and flow-through modes is that in batch mode thermal control is effected by varying the temperature of the heater while in flow-through mode, thermal cycling is effected by transporting the droplets among distinct constant temperature zones. In the "batch" method a single integrated thin-film heater on the droplet microactuator was used to thermally cycle static droplets located within the heater zone. In the "flow-through" method, two distinct fixed temperature zones were created on the droplet microactuator and thermal cycling was performed by shuttling the droplets between the two zones.

In the "batch" case, the thermal mass of the heater itself as well as thermal losses may be minimized through the use of thin-film heaters placed directly adjacent to the droplets. Because the thermal masses, including the droplet itself, are so small, rapid temperature changes can be effected. Passive cooling (in filler fluid) is also rapid because the total energy input into the system is extremely small compared to the total thermal mass.

For "flow-through" heating, a larger thermal mass is desirable because it helps to stabilize the temperature while a slower ramp rate is tolerable because the heater temperature is not varied once it reaches its set point. A flow-through system can, for example, be implemented using block heaters external to the droplet microactuator which were more accurate and easier to control than thin-film heaters although, in principle either type of heater could be used to implement either method.

In another embodiment, temperature is controlled by flowing or recirculating heated filler fluid through the chip and around the droplets.

The droplet microactuator layout is scalable, such that a droplet microactuator may include a few as one heating zone up to tens, hundreds or more heating zones.

7.8.7.2 Heater Types

Heaters may be formed using thin conductive films. Examples of suitable thin films include Pt heater wires and transparent indium-tin-oxide (ITO). ITO provides better visualization of the droplets for real-time observation. A remotely placed conventional thermocouple (TC) for temperature regulation can also be used. In one embodiment, tiny metal (e.g., copper) vias in the PCB substrate are used to create tight thermal junctions between the liquid and the remote TC. Further, sample temperature can be determined by monitoring the copper via using a surface mount thermistor or an infrared sensor. One advantage of using a thermistor is that they are small enough (2×2 mm) to be soldered directly on the droplet microactuator, while an advantage of using IR is that it is non-contact method which would simplify the interfacing. Because the thermal conductivity of copper is at least 700 times greater than the FR-4 substrate (350-390 W/m·K versus 0.3-0.5 W/m·K) the temperature of a Cu via will accurately represent the temperature inside the liquid. Heaters may be integrated on the bottom and/or top (when present) plate of the droplet microactuator and on the bottom and/or top surface of either plate, or integrated within the structure of either plate.

In one flow-through embodiment, reduced thermal gradients can be provided by using heaters to create a continuous temperature gradient across the droplet microactuator (e.g., from 100 to 50° C.). The use of a continuous gradient will eliminate the need to overcome the steep temperature gradients found along the edge of the heater blocks. A controlled temperature gradient would also significantly enhance the functionality of the device by allowing protocols with arbitrary numbers of temperature points to be implemented. Furthermore, each reaction can be performed with a custom thermal protocol while only the temperatures of the two or more blocks would need to be thermally regulated. The droplets will be transported to and held at the appropriate location between the heaters to achieve a target temperature. The fluorescence of the droplets can be imaged using a fluorescence sensor as they are transported over a detection spot. The temperature of the upper and lower target temperatures can be varied by changing the location of the droplets.

In some embodiments, heaters located above the droplets may obscure the droplets thus interfering with real-time optical measurements. In such cases, the droplets can be transported out from underneath the heaters to a location which is preferred for optical detection (i.e. a detection spot). Droplets may be periodically transported out from underneath the heaters to a detection spot on the droplet microactuator detection purposes, e.g. detection by fluorescence quantitation. Droplets may be routed into proximity with a sensor while cycling them from one temperature zone to another.

7.8.8 Detection

The droplet microactuator systems as contemplated herein may include on-chip and/or off-chip mechanisms for analyzing droplets. For example, the droplet microactuator may include one or more detection methods such as amperometry, potentiometry, conductometry, absorbance, chemiluminescence, and fluorescence. The droplet manipulation module and the detection module may in some embodiments be decoupled by building them on separate substrates. Alternatively, the droplet microactuator may incorporate detection components. Thus, for example, the droplet microactuator may include one or more of the following, on-chip or off-chip: amperometry module arranged to measure current flowing through a droplet; potentiometry module including a measuring and a reference electrode arranged to measure equilibrium electrode potential of a droplet; conductometry module arranged to measure conductivity of a droplet; absorbance module arranged to measure energy or light absorbance of a droplet; chemiluminescence module designed to measure light emission by chemical species in a droplet; fluorescence module designed to excite and measure fluorescence of the species in a droplet. Off-chip detection modules may, for example, be provided in a cartridge that comprises the chip and/or in an analyzer into which the cartridge or chip may be inserted.

Preferred detection methods are absorbance, electrochemical, fluorescence, and chemiluminescence. In one embodiment, two or more of these methods are accomplished on a single droplet microactuator. In another embodiment, the droplet microactuator includes one detection module, but the system is programmed to conduct more than one test using the module. In this embodiment, processed sample droplets requiring testing are sequentially moved into position for testing. Thus, multiple samples are multiplexed over a detection spot where a single detector is used.

Preferred assays for inclusion on the droplet microactuator include colorimetric assays (e.g., for proteins), chemiluminescence assays (e.g., for enzymes), enzymatic and electrochemical assays (e.g., for metabolites, electrolytes, and gases), and conductometric assays (e.g., for hematocrit on plasma and whole blood). In one embodiment, a single droplet microactuator includes modules for 2, 3, 4, 5 or more different kinds of assays. In another embodiment, a single droplet microactuator cartridge includes on-chip and/or off-chip modules for 2, 3, 4, 5 or more different kinds of assays. In yet another embodiment, a single droplet microactuator system includes on-chip, off-chip, on-cartridge and/or off-cartridge modules for 2, 3, 4, 5 or more different kinds of assays.

7.8.9 Droplet Operations

The droplet microactuator may conduct various droplet operations with respect to a droplet. Examples include: loading a droplet into the droplet microactuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet microactuator; other droplet operations described herein; and/or any combination of the foregoing.

Droplet dispensing refers to the process of aliquoting a larger volume of fluid into smaller droplets. Dispensing is usefully employed at the fluidic interface, the input reservoirs, and at processing reservoirs. Droplets may be formed by energizing electrodes adjacent to the fluid reservoir causing a "finger" of fluid to be extended from the reservoir. When the fluid front reaches the terminal electrode, the intermediate electrodes are de-energized causing the fluid to retract into the reservoir while leaving a newly-formed droplet on the terminal electrode. As previously noted, one or more electrodes in the reservoir may also be energized to assist in separating the droplet being dispensed from the bulk fluid. Because the droplet conforms to the shape of the electrode, which is fixed, excellent accuracy and precision are obtained. Droplet dispensing is controlled by the controller. In some embodiments the invention employs droplet dispensing structures and/or techniques described in U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000, both to Shenderov et al., the disclosures of which are incorporated herein by reference.

In some embodiments, droplet operations are mediated by electrowetting techniques. In other embodiments, droplet operations are mediated by electrophoresis techniques.

In still other embodiments, droplet operations are mediated by electrowetting techniques and by electrophoresis techniques.

In one embodiment, separations may be performed using a combination of electrowetting and electrophoresis. Electrowetting microactuation can be used to create a channel to perform electrophoresis; to deliver a sample to the channel or capture a sample fraction from channel following an electrophoretic separation. For example, for forming a channel, electrowetting can be used to deform (stretch) a droplet of separation medium in a long thin shape followed. In some cases, the channel may be polymerized, e.g., using UV polymerization. In other cases, the channel may be formed by using droplet operations to add droplets into a physically confined microchannel. In a related embodiment, the effective length of an electrophoresis channel can be increased by capturing the fraction of interest in a droplet at the output and then returning it to the input in a cyclical fashion. Using the same principle, a series of progressively finer separation can be performed. Separations may also be accomplished using multiple different separation mediums at the same time.

Droplet splitting or dividing of droplets generally involves separating a droplet into two or more sub-droplets. In some cases, the resulting droplets are relatively equal in size.

Transporting involves moving a droplet from one location to another in any direction. Droplets may be transported on a plane or in three dimensions. It will be appreciated that a variety of droplet operations, such as dispensing and/or splitting may include a transporting element, in which on droplet is transported away from another droplet.

Merging involves combining two or more droplets into a single droplet. In some cases, droplets of relatively equal size are merged into each other. In other cases, a droplet may be merged into a larger droplet, e.g., combining droplet with a larger volume present in a reservoir.

Mixing a droplet involves various droplet manipulations, such as transporting or agitating, that result in a more homogenous distribution of components within the droplet. In one mixing embodiment, a droplet positioned over an electrowetting electrode is rapidly and cyclically deformed in place by activating and deactivating the electrode, inducing fluid currents within the droplet which facilitate mixing. Frequency-dependent effects such as mechanical resonances may be used to tune the quality and speed of mixing. Compared to techniques which require transport of droplets on a surface for mixing this approach minimizes the area required for mixing. This mixing scheme can be employed without the presence of a top plate. Due to space-saving advantage, this scheme could provide for simplified mixing in reaction wells since only one electrode is needed.

Reagents or samples from reservoirs may be dispensed as discrete droplets for transport to other locations on the droplet microactuator.

The invention includes droplet operations using droplets comprising beads. A variety of such operations are described elsewhere herein. In one embodiment, beads are used to conduct droplet operations on reagents that are prone to interfere with droplet operations. For example, certain proteins may be prone to bind to surfaces of a droplet microactuator and/or to partition into the filler fluid. Immobilizing such compounds on hydrophilic beads can be used to facilitate droplet operations using the compounds. The compounds can be bound to the beads, and the beads can contained with a droplet which is subjected to droplet operations.

In one particular dispensing operation, coagulation is used to separate serum from whole blood. Whole blood is loaded onto the chip and combined with a droplet comprising a coagulating agent. Following coagulation, droplets are dispensed from the sample. Because cells and platelets are trapped in place, the liquid dispensed from the sample will contain only serum.

7.9 System

The various aspects of the present invention may also include systems which include the droplet microactuator coupled to a processor which may be programmed to control the droplet microactuator. Various input means, such as keyboards, switches and touch screens, and various output means, such as display screens, output ports, and wireless transmitting devices, may also be included in electronic communication with the processor. The droplet microactuator may be presented as a component of a cartridge for insertion in an analyzer. The cartridge may include one or more preloaded reagents, which are dispensed into the droplet microactuator prior to, during, or after insertion of the cartridge into the analyzer.

Systems can be programmed to execute a wide variety of protocols involving any number of droplet manipulations. Multiple droplets can be independently and simultaneously manipulated on a single droplet microactuator. The capacity to independently manipulate multiple droplets in parallel enables execution of complex protocols as a series of basic microfluidic instructions. Moreover, droplet microactuators are scalable, enabling systems that control tens, hundreds, thousands or more parallel droplet manipulations per droplet microactuator chip. For example, at any one moment, up to a maximum of every control electrode on the droplet microactuator may be engaged in a droplet operation.

The system can be programmed to enable users to input instructions for the execution of protocols. Existing protocols may be monitored and adjusted according to user requirements. Complex protocols can be implemented in which the outcome of one or more steps determines the selection of one or more subsequent steps. For example, a droplet in which a certain measured result is positive may be transported for further processing, while a droplet in which a result is negative may be discarded, or vice versa.

Flexibility of operations in the systems of the invention is much greater, for example, than the flexibility of robotic systems, which would require a massive assembly of robotics, a huge facility, and thousands of times the amount of reagents to achieve anything near the massively parallel operations that are enabled by the droplet microactuator. Nevertheless, in some embodiments, robotics may be useful for droplet microactuator or cartridge placement, reagent loading, placement of detectors for external measurements of on-chip phenomena, and the like.

7.10 Kit

A further aspect of the invention is a kit including reagents, sample collection devices, and/or a droplet microactuator or cartridge for conducting the methods of the invention.

LITERATURE CITED

The entire disclosure of each of the following references is incorporated herein by reference:

1. A. McPherson, "Crystallization of macromolecules—General principles" Methods in Enzymology A, 114, 112-120, 1985.
2. N. E. Chayen, "Recent advances in methodology for the crystallization of biological macromolecules," Journal of Crystal Growth, 198/199, 649-655, 1999.
3. N. E. Chayen, P. D. Shaw Stewart, D. L. Maeder, and D. M. Blow, "An automated system for micro-batch protein crystallization and screening," Journal of Applied Crystallography, 23, 297-302, 1990.
4. J. R. Luft, D. M. Rak, G. T. DeTitta, "Microbatch macromolecular crystallization in micropipettes," Journal of Crystal Growth, 196, 450-455, 1999.
5. R. C. Stevens, "High-throughput protein crystallization," Current Opinion in Structural Biology, 10, 558-563, 2000.
6. H. I. Krupka, B. Rupp, B. W. Segelke, T. P. Lekin, D. Wright, H. C. Wu, P. Todd, and A. Azarani, "The high-speed Hydra-Plus-One system for automated high-throughput protein crystallography," Acta Crystallographica, D58, 1523-1526, 2002.
7. M. Yamada, C. Sasaki, T. Isomura, and M. Seki, "Microfluidic reactor array for high-throughput screenings of protein crystallization conditions," Proc. of micro Total Analysis Systems 2003, 449-452, 2003.
8. M. Hirano, T. Torii, T. Higuchi, and H. Yamazaki, "A droplet-based protein crystallization device using electrostatic micromanipulation," Proc. of Micro Total Analysis Systems, pp. 148-150, 2004.
9. A. Sanjoh, T. Tsukihara, "Spatiotemporal protein crystal growth studies using microfluidic silicon devices," Journal of Crystal Growth, 196, 691-702, 1999.
10. E. E. G. Saridakis, P. D. Shaw Stewart, L. F. Lloyd, and D. M. Blow, "Phase Diagram and Dilution Experiments in the Crystallization of Carboxypeptidase G2," Acta Crystallographica, D50, 293-297, 1994.
11. V. Srinivasan, V. K. Pamula, P. Paik, and R. B. Fair, "Protein Stamping for MALDI Mass Spectrometry Using an Electrowetting-based Microfluidic Platform," Lab-on-a-Chip: Platforms, Devices, and Applications, Conf. 5591, SPIE Optics East, Philadelphia, Oct. 25-28, 2004.
12. Chayen, N. E., (2003) Journal of Structural and Functional Genomics 4: 115-120.
13. J. Jancarik and S.-H. Kim, "Sparse matrix sampling: a screening method for the crystallization of macromolecules," Journal of Applied Crystallography, 24, 409, 1991.
14. J. R. Luft, J. Wolfley, I. Jurisica, J. Glasgow, S. Fortier, and G. T. DeTitta, "Macromolecular crystallization in a high throughput laboratory—the search phase," Journal of Crystal Growth, 232, 591-595, 2001.
15. Cudney, R., et al., Screening and optimization strategies for macromolecular crystal growth., Acta Cryst. (1994) D50, 414-423.

16. P. S. Stewart from Douglas Instruments. Quoted in Recent Advances in Macromolecular Crystallization 2005/http://www.hamptonresearch.com/stuff/RAMC/RAMC2005Notes.aspx).
17. T. W. Schulte, S. Akinaga, T. Murakata, T. Agatsuma, S. Sugimoto, H. Nakano, Y. S. Lee, B. B. Simen, Y. Argon, S. Felts, D. O. Toft, L. M. Neckers and S. V. Sharma, "Interaction of Radicicol with Members of the Heat Shock Protein 90 Family of Molecular Chaperones," Molecular Endocrinology 13 (9): 1435-1448, 1999.
18. E. R. Bodenstaff, F. J. Hoedemaeker, M. E. Kuil, H. P. M. de Vrind, and J. P. Abrahams, "The prospects of nanocrystallography," Acta Crystallographica Section D, Biological Crystallography, D58, 1901-1906, 2002.
19. J. R. Minkel. 2004. Microfluidics Goes Mainstream. *Drug Discovery and Development. June* 2004.
20. B. Tulusi. 2004. Liquid Handling Systems Get Smaller, Smarter, Speedier. *Drug Discovery and Development. January* 2004.
21. D. R. Reyes, D. Iossifidis, P. A. Auroux, and A. Manz, "Micro Total Analysis Systems. 1. Introduction, Theory, and Technology," *Analytical Chemistry,* 74(12), 2623-2636, 2002.
22. D. Iossifidis, D. R. Reyes, P. A. Auroux, and A. Manz, Micro Total Analysis Systems. 2 Analytical Standard Operations and Applications," *Analytical Chemistry,* 74(12), 2637-2652, 2002.
23. R. B. Fair, M. G. Pollack, R. Woo, V. K. Pamula, R. Hong, T. Zhang, and J. Venkatraman, "A micro-watt metal-insulator-solution-transport (MIST) device for scalable digital bio-microfluidic systems," IEEE International Electron Devices Meeting. *Technical Digest,* 16.4.1-4, 2001.
24. H. Ren, V. Srinivasan, M. G. Pollack, and R. B. Fair, "Automated electrowetting-based droplet dispensing with good reproducibility," *Proc. Micro Total Analysis Systems* (µTAS), 993-996, 2003.
25. Vijay Srinivasan, Vamsee K. Pamula, Phil Paik, and Richard B. Fair, "Protein stamping for MALDI mass spectrometry using an electrowetting-based microfluidic platform," *Proc. SPIE Lab-on-a-chip platforms, devices, and applications,* Vol. 5591.
26. A. W. Adamson and A. P Gast, *Physical Chemistry of Surfaces,* Wiley-Interscience; 6 edition (Aug. 4, 1997).

9 CONCLUDING REMARKS

The foregoing detailed description of embodiments refers to the accompanying drawings, which illustrate specific embodiments of the invention. Other embodiments having different structures and operations do not depart from the scope of the present invention.

This specification is divided into sections for the convenience of the reader only. Headings should not be construed as limiting of the scope of the invention.

It will be understood that various details of the present invention may be changed without departing from the scope of the present invention. Furthermore, the foregoing description is for the purpose of illustration only, and not for the purpose of limitation, as the present invention is defined by the claims as set forth hereinafter.

We claim:

1. A method of dispensing at least one sample droplet from a parent droplet, the method comprising:
    (a) providing a droplet actuator comprising substrates arranged to form a gap, wherein:
        (i) the gap comprises:
            (1) the parent droplet comprising a protein in a concentration exceeding 10 mg/mL;
            (2) an oil filler fluid surrounding the parent droplet, the filler fluid comprising a, surfactant in an amount selected to enhance droplet operations; and
        (ii) one or more of the substrates comprise electrodes arranged for conducting droplet operations in the gap by electrowetting using the parent droplet; and
    (b) using the electrodes to conduct the droplet operations comprising dispensing at least one sample droplet from the parent droplet.
2. The method of claim 1 wherein the protein concentration exceeds 50 mg/mL.
3. The method of claim 1 wherein the protein concentration exceeds 100 mg/mL.
4. The method of claim 1 wherein the oil flier fluid comprises the surfactant in an amount which ranges from 0.001 to 10% w/w.
5. The method of claim 1 wherein the oil filler fluid comprises the surfactant in an amount which ranges from 0.001 to 1% w/w.
6. The method of claim 1 wherein the oil filler fluid comprises the surfactant in an amount which ranges from 0.001 to 0.1% w/w.
7. The method of claim 1 wherein the parent droplet has a volume which does not exceed 100 nL.
8. The method of claim 1 wherein the parent droplet has a volume which does not exceed 50 nL.
9. The method of claim 1 wherein the parent droplet has a volume which does not exceed 20 nL.
10. The method of claim 1 wherein the parent droplet has a volume which does not exceed 10 nL.
11. The method of claim 1 further comprising repeating the dispensing step to produce a set of sample droplets with <2% CV.
12. The method of claim 1 wherein an enhancement in droplet operations comprises a reduction in protein contamination of droplet microactuator surfaces.
13. The method of claim 1 wherein the surfactant enables the dispensing of the at least one sample droplet.
14. The method of claim 1 wherein the oil filler fluid comprising the surfactant increases compatible protein concentration by more than 3 orders of magnitude relative to oil filler fluid in the absence of the surfactant.
15. The method of claim 1 wherein the surfactant increases the concentration of protein that can be reliably dispensed on the droplet actuator.
16. The method of claim 1 wherein the oil filler fluid comprises silicone oil.
17. The method of claim 1 wherein the dispensing of the at least one sample droplet is effected from on-actuator sample reservoirs.
18. The method of claim 1 wherein the dispensing of the at least one sample droplet is effected using from 1 mV to 50 kV.
19. The method of claim 1 wherein the dispensing of the at least one sample droplet is effected using from 1V to 10 kV.
20. The method of claim 1 wherein the dispensing of the at least one sample droplet is effected using from 5V to 1000V.
21. The method of claim 1 wherein the dispensing of the at least one sample droplet is effected using from 10V to 300V.
22. The method of claim 1 wherein the dispensing of the at least one sample droplet is effected using AC.
23. The method of claim 1 wherein the dispensing of the at least one sample droplet is effected using DC.

* * * * *